United States Patent [19]

Ohira et al.

[11] Patent Number: 6,143,724

[45] Date of Patent: Nov. 7, 2000

[54] 2-FLUOROFUCOSYL-N-AROYLGLUCOSAMINE DERIVATIVES, INTERMEDIATES, THEREFOR, AND PROCESSES FOR PRODUCING THESE

[75] Inventors: Yutaka Ohira; Takao Iida, both of Tsukuba, Japan

[73] Assignee: Daikin Industries, Ltd., Osaka, Japan

[21] Appl. No.: 09/462,916

[22] PCT Filed: Jul. 16, 1998

[86] PCT No.: PCT/JP98/03224

§ 371 Date: Jan. 18, 2000

§ 102(e) Date: Jan. 18, 2000

[87] PCT Pub. No.: WO99/03870

PCT Pub. Date: Jan. 28, 1999

[30] Foreign Application Priority Data

Jul. 18, 1997 [JP] Japan .................................. 9-193668

[51] Int. Cl.[7] .................. A61K 31/70; A61K 31/715; C07H 15/00; C07H 3/06; C07H 1/00
[52] U.S. Cl. .................................. 514/25; 514/54; 514/62; 536/17.2; 536/124

[58] Field of Search .................................. 514/25, 54, 62; 536/17.2, 124

[56] References Cited

U.S. PATENT DOCUMENTS

| 5,604,207 | 2/1997 | DeFrees et al. | 514/25 |
| 5,811,404 | 9/1998 | DeFrees et al. | 514/25 |
| 5,854,218 | 12/1998 | DeFrees et al. | 514/25 |

*Primary Examiner*—Deborah C. Lambkin
*Attorney, Agent, or Firm*—Armstrong, Westerman, Hattori, McLeland & Naughton

[57] ABSTRACT

2-Fluorofucosyl-N-aroylglucosamine derivatives which are obtained by substitution of a hydroxyl group at the 3- or 4-position of N-aroylglucosamine with 2-fluorofucose, their intermediates and preparation methods thereof. The 2-fluorofucosyl-N-aroylglucosamine derivatives which are useful medicinal components for the treatment, improvement and prevention of inflammation and diseases accompanying inflammation, their intermediates and preparation methods thereof can be provided.

22 Claims, 1 Drawing Sheet

2-FLUOROFUCOSYL-N-AROYLGLUCOSAMINE DERIVATIVES, INTERMEDIATES, THEREFOR, AND PROCESSES FOR PRODUCING THESE

This application is a 371 of PCT/JP98/03224 filed Jul. 16, 1998.

FIELD OF THE INVENTION

The present invention relates to 2-fluorofucosyl-N-aroylglucosamine derivatives which are obtained by substituting the hydroxyl group at the 2-position with a fluorine atom in L-fucose of fucosyl-α-(1→3 or 1→4)-N-aroylglucosamine which are derivatives of Lewis X, Lewis a, sialyl Lewis X or sialyl Lewis a glycosides (or saccharides) known as the causal substances of inflammation or thrombus formation accompanied by inflammation, tissular disorder due to infiltration of inflammatory cells, asthma, rheumatism, autoimmune disease, or cancer metastasis, and their intermediates, and preparation methods thereof (herein, the aroyl group is synonymous with the arylcarbonyl group). Such derivatives are useful as medicinal components for the purpose of treatment, improvement and prevention of the said diseases.

PRIOR ART

Sialyl Lewis X glycoside, which is a oligosaccharide including fucose, has been attracting attention in recent years as a molecule involved in a homing phenomena, where leucocytes interact with selecting, an adhesion-factor on vascular endothelial cells, and are expelled from the vascular system when inflammation occurs. Further, it has been understood that another ligand of selectin, sialyl Lewis a glycoside [structural formula (IV)] is significantly involved in the liver metastasis of colon cancer [refer to Katsumoto Ito, Progress of Medical Science; 179, 223 (1996)]. Some of the above homing phenomena are initiated by the interaction between the lectinic cell-adhesion molecule called selectin and sialyl Lewis X oligosaccharide. Therefore, neutrophil (a kind of leukocyte)-dependent and selectin-dependent acute inflammation is expected to be suppressed if sialyl Lewis X oligosaccharide can be utilized as a selectin inhibitor.

As an example, a group at Michigan University showed that acute inflammation of the lung induced experimentally in rats using cobra toxin was reduced by administering sialyl Lewis X glycoside [structural formula (III)] [M. S. Mulligan et al., Nature 364, 149 (1993)], and Hayashi et al. also reported the efficacy of sialyl Lewis X derivatives in a lung disease model [Shinichiro Tojo et al., Cell 29 (2), 17 (1997)]. Further, various sialyl Lewis X derivatives have been synthesized from the entirely novel point of view of developing drugs for the inhibition of cell-adhesion. Among them interrelations between their structures and activities have been investigated by Hasegawa and Kiso et al. and their core partial structures are reportedly (1) carboxylic acid in sialic acid, (II) fucose residue, and (III) hydroxyl groups at the 4- and 6-positions in galactose [A. Hasegawa et al., Carbohydrate Research; 257, 67 (1994)]. Furthermore, it is reported that the adhesion-inhibitory activity of the glycoside deoxidized at the 1-position of the reducing terminal [structural formula (V)] to P selectin, which is a member of the selectin family, is 20 times higher than the activity of the sialyl Lewis X glycoside shown in Structural Formula (III) [H. Kondo et al., Journal of Medicinal Chemistry 39, 1339 (1996)]. In addition, synthesis of the Lewis X derivatives [structural formula (VI)] by substituting a sialic acid moiety of sialyl Lewis X with an acidic functional group such as a sulfate residue, a phosphate residue, or a carboxylic acid, and investigation of the adhesion-inhibitory activity for selectins lead to the discovery of GSC-150 as a powerful selectin blocker [refer to H. Kondo et al., Journal of Medicinal Chemistry 39, 2055 (1996); U.S. Pat. No. 5,589,465; JP Opening No. 8-99989].

Structural formula (I):

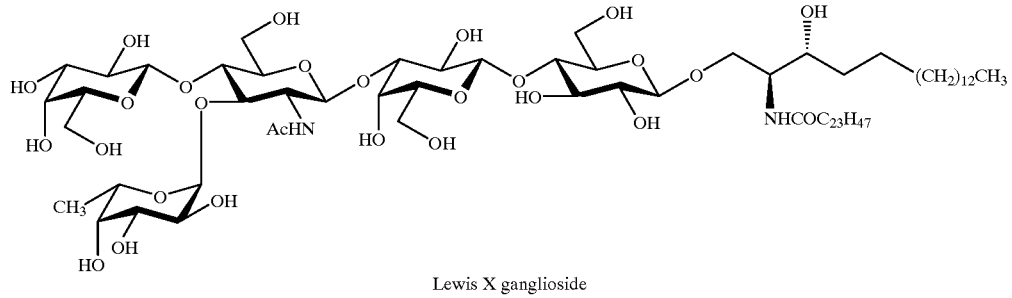

Lewis X ganglioside

Structural formula (II):

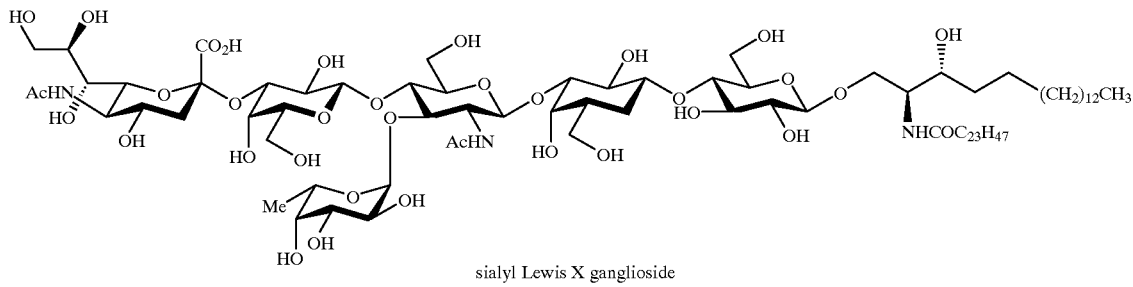

sialyl Lewis X ganglioside

Structural formula (III):

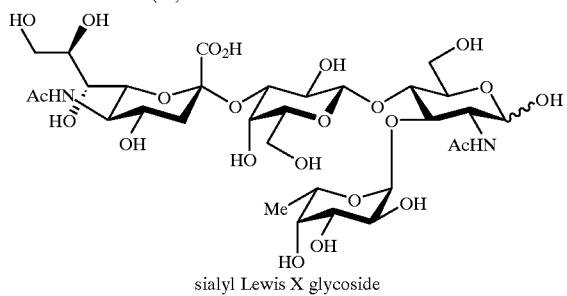

sialyl Lewis X glycoside

Structural formula (IV):

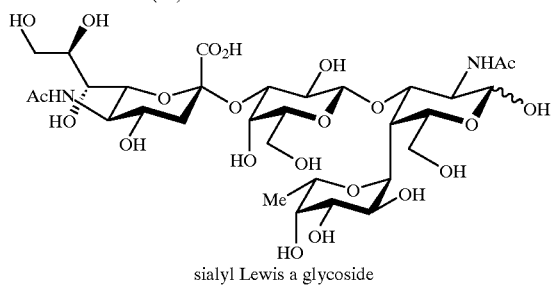

sialyl Lewis a glycoside

Structural formula (V):

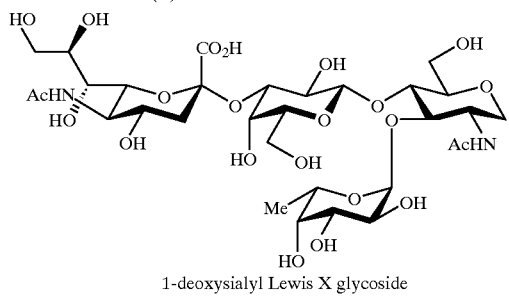

1-deoxysialyl Lewis X glycoside

Structural formula (VI):

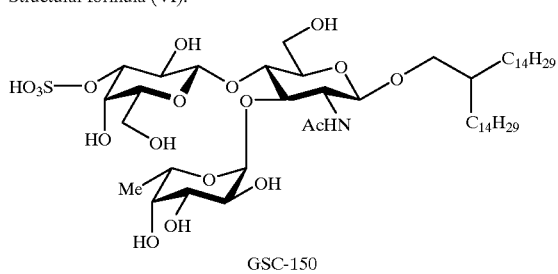

GSC-150

OBJECTS OF THE INVENTION

Lewis X or Lewis a derivatives are known as ligand moieties of P selectin or L selectin that act as cell-adhesion molecules. Although they are important compounds that function as cell recognition factors which specifically express these selecting, they are expected to easily lose their activity due to α-fucosidase existing in the human body, because they have an L-fucosyl-α-(1→3 or 1→4)-glucose skeleton [C. H. Wong et al., Journal of Organic Chemistry, 60, 3100 (1995)]. As a further example, the following items 1–3 have been investigated from the standpoint of selectin-adhesion-inhibitory activity or metabolic stability.

1. According to the previous application by the present inventors (JP Appl. 9-52902), sialyl Lewis X ganglioside was synthesized by substituting the hydroxyl group at the 2-position in fucose with a fluorine atom in anticipation of improved metabolic stability to α-fucosidase, and it was found to have a similar selectin-adhesion-inhibitory activity as natural type sialyl Lewis X ganglioside. The following are typical compounds.

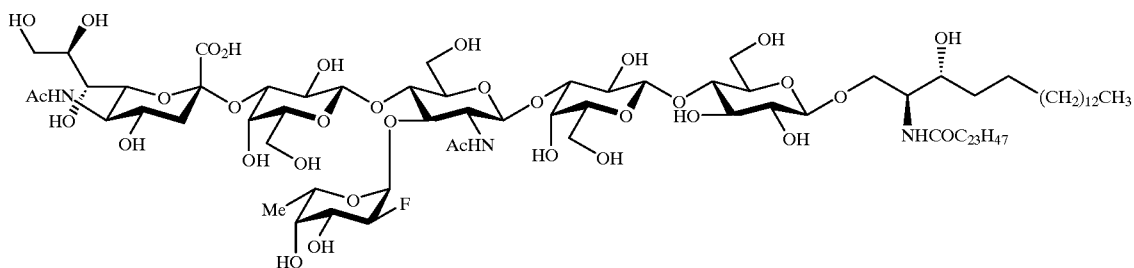

2. Hayashi et al. [M. Hayashi et al., Journal of Organic Chemistry; 61, 2938 (1996); WO 96/20204] report that selectin-adhesion-inhibitory activity is enhanced by conversion of an acetylamide moiety of sialyl Lewis X into naphthoylamide. The following are typical compounds.

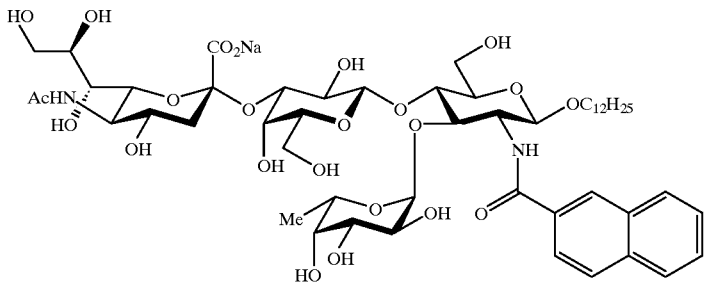

M. Hyashietal. Journal of Organic Chemistry; 61, 2938 (1996).

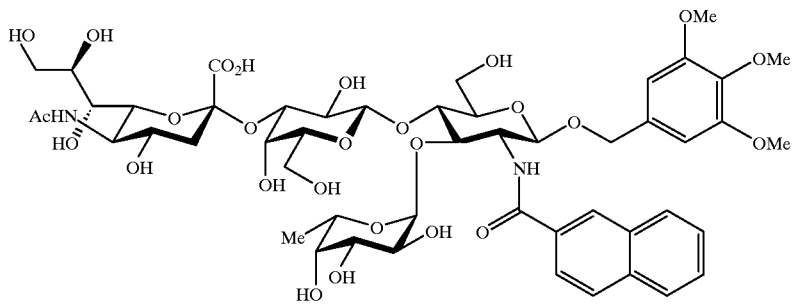

M. Hayashi et al. WO 96/20204.

3. S. A. DeFrees et al. report that selectin-adhesion-inhibitory activity is enhanced by conversion of an acetylamide of the N-acetylglucosamine moiety in sialyl Lewis X into aroylamide [S. A. DeFrees et al,. Journal of Medicinal Chemistry; 39, 1357 (1996), WO 94/26760, U.S. Pat. No. 5,604,207]. Further, they report that the adhesion-inhibitory activity was markedly enhanced by preparing sialyl Lewis X liposom where PEG-DSPE was integrated into the aroyl group [S. A. DeFrees et al., Journal of American Chemical Society; 118, 6101 (1996)]. Examples are given as follows.

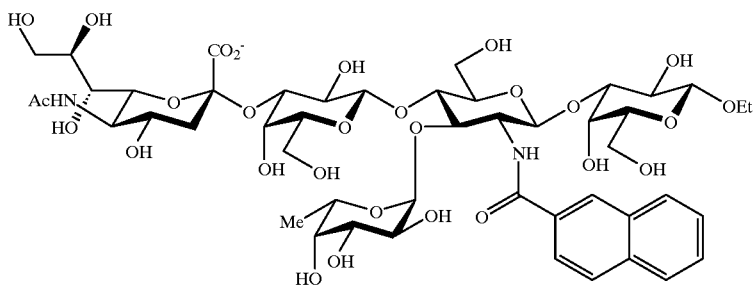

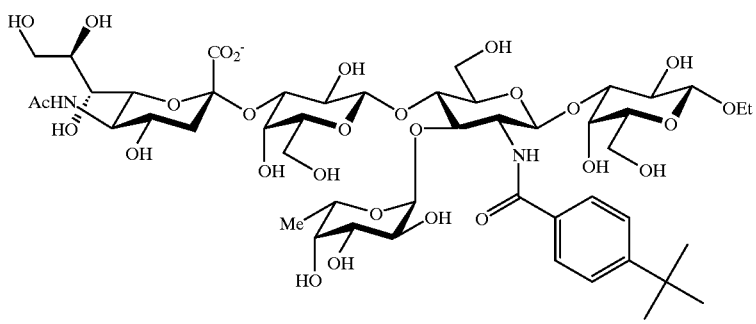

S. A. DeFrees et al,. Journal of Medicinal Chemistry; 39, 1357 (1996).
S. A. DeFrees et al., WO 94/26760, S. A. DeFrees et al., U.S. Pat. No. 5,604,207.

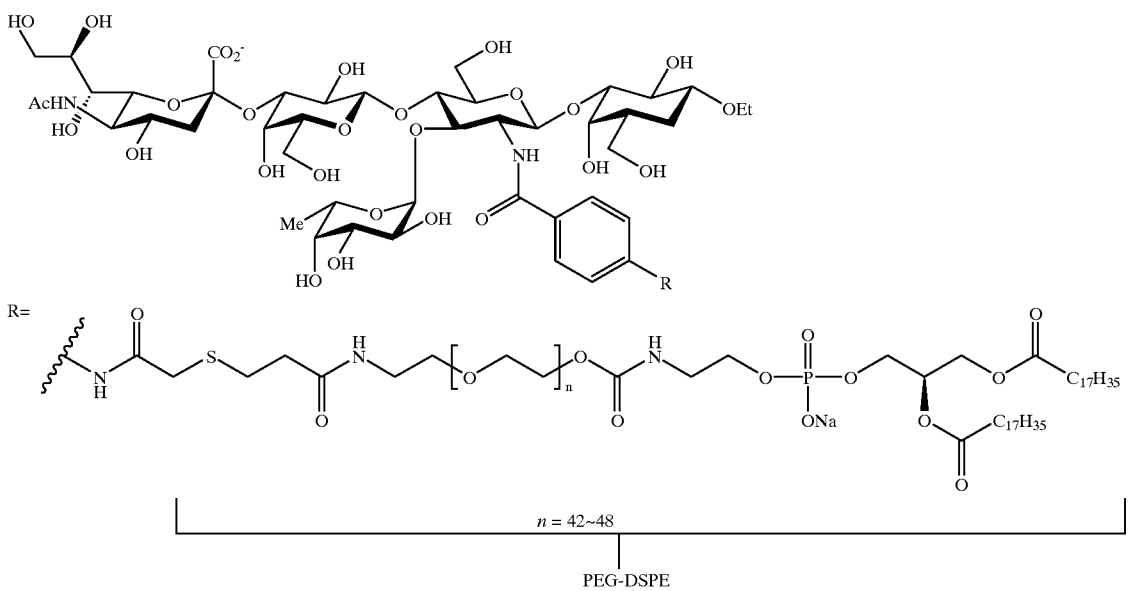

S. A. DeFrees et al., Journal of American Chemical Society; 118, 6101 (1996)

Thus, sialyl Lewis X derivatives are considered to be practical, and providing them is extremely meaningful. However, there is as yet no method for selectively α-2-fluorofucosylizing the 3- or 4-position in N-aroylgulucosamine derivatives. Moreover, these N-aroylglucosamine derivatives which are selectively α-2-fluorofucosylized at the 3- or 4-positions are considered to be more efficient in selectin-adhesion-inhibitory activity and metabolic stability. Therefore, the present inventors have tried to create N-aroylglucosamine derivatives (fucosylglucosamine analogs) in which the 3- or 4-positions are selectively α-2-fluorofucosylized as glycosides having more powerful selectin-adhesion-inhibitory activity and greater metabolic stability.

OBJECTS OF THE INVENTION

The objects of the present invention are to provide 2-fluorofucosyl-N-aroylglucosamine derivatives that have a superior inhibitory activity to selectin-adhesion and greater metabolic stability, their intermediates, and preparation methods thereof.

CONSTITUTION OF THE INVENTION

Considering the prior situation described above and after extensive studies, the present inventors have succeeded in synthesizing the Lewis X and Lewis (a) analogs which are obtained by substituting the hydroxyl group at the 3-position or 4-position in N-aroylglucosamines with 2-fluorofucose, which strongly inhibits the adhesion between selectins and neutrophils and which has greater metabolic stability.

Namely, the present invention relates to the 2-fluorofucosyl-N-aroylglucosamine derivatives (hereinafter, sometimes referred to as "the present inventive derivatives") represented by the following general formula (1).

General formula (1):

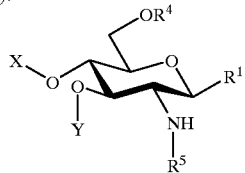

[wherein X and Y in the above general formula (1) are a group represented by the following general formula (A) or (B):

Y=general formula (B) when X=general formula (A); and
Y=general formula (A) when X=general formula (B)].

General formula (A):

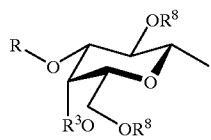

General formula (B):

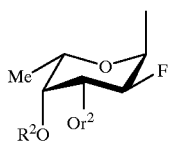

Herein, R in above general formula (A) is a hydrogen atom, protecting group of the hydroxyl group, phosphate residue, sulfate residue, or the sialyl group represented by the following general formula (a).

General formula (a):

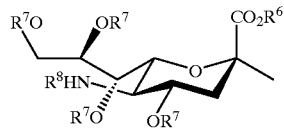

(wherein $R^6$ in the above general formula (a) shows a hydrogen atom, sodium atom or C1–10 alkyl group; $R^7$ shows a hydrogen atom, C1–10 alkanoyl group or C7–15 aroyl group; $R^8$ shows an acetyl group, hydroxyacetyl group, or C1–10 alkanoyloxyacetyl group). Further, in the above general formula (1), $R^1$ is a hydrogen atom, hydroxyl group, C1–10 alkanoyloxy group having no substituent or having one or more substituents, C7–15 aroyloxy group, arylthio group having no substituent or having one or more substituents, C1–18 alkoxy group, branched long chain alkoxy group, arylmethoxy group having no substituent or having one or more substituents, 2-trisilylethoxy group having C1–4 alkyl group or phenyl group, or a group represented by the following general formula (b) or (c).

General formula (b):

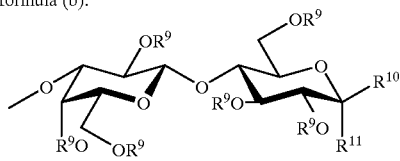

General formula (c):

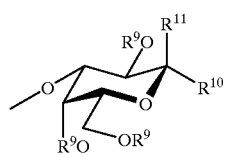

(wherein $R^9$ in the above general formulas (b) and (c) shows a hydrogen atom, C1–10 alkanoyl group, C7–15 aroyl group or phenylmethoxy group having no substituent or having substituents; $R^{10}$ shows a hydrogen atom, hydroxyl group, 2-trisilylethoxy group having C1–4 alkyl group or phenyl group, C1–30 alkoxy group, or a group represented by the following general formula (d); $R^{11}$ shows a hydrogen atom or —O—C(=NH)CCl$_3$.)

General formula (d):

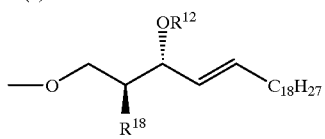

[wherein $R^{12}$ in the above general formula (d) shows a hydrogen atom or benzoyl group; $R^{13}$ shows an azide, amine or sphingosine represented by NHCO $R^{14}$ ($R^{14}$ is a C15–25 alkyl group); $R^{11}$ shows hydrogen atom or —O—C(=NH)CCl$_3$]. Further, in the above general formulas (1), (A) and (B), $R^2$, $R^3$ and $R^4$ are a hydrogen atom, C1–10 alkanoyl group, C7–15 aroyl group, or phenylmethyl group having no substituent or having substituents (wherein at least two of $R^2$, $R^3$ and $R^4$ may be the same as each other or they may be different) and $R^5$ shows an aroyl group having no substituent or having substituents. Furthermore, the present invention provides a preparation method for 2-fluorofucosyl-N-aroylglucosamine derivatives (hereinafter, sometimes referred to as "the preparation method of the present inventive derivatives") using the compounds represented by the following general formulas (A') and (B') and the aroylglucosamine derivatives represented by the following general formula (C') as the method for preparing the present inventive derivatives with good reproductivity.

General formula (A'):

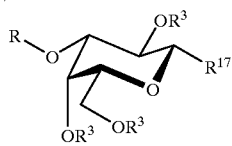

-continued

General formula (B'):

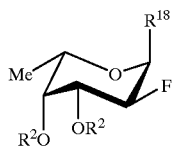

General formula (C'):

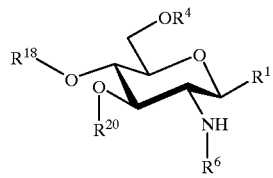

(wherein R, $R^1$, $R^2$, $R^3$, $R^4$ and $R^5$ in the above general formulas (A'), (B') and (C') are the same as described above; $R^{17}$, $R^{18}$, $R^{19}$ and $R^{20}$ are reactive groups, respectively; $R^{17}$ shows reactivity with $R^{19}$ or $R^{20}$; and $R^{16}$ shows reactivity with $R^{19}$ or $R^{20}$. Further, the present invention provides the intermediates tie of 2-fluorofucosyl-N-aroylglucosamine derivatives (hereinafter, sometimes referred to as "the first intermediate of the present invention") represented by the following general formula (4) as a useful synthetic intermediate of 2-fluorofucosyl-N-aroylglucosamine derivatives (namely, the Lewis X derivative, the present inventive derivatives) represented by the above general formula (1).

General formula (4):

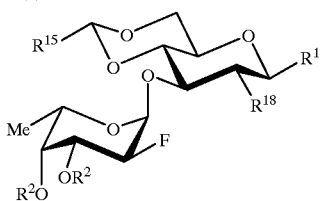

(wherein $R^1$ and $R^2$ in the above general formula (4) are the same as described above or in claim 1; $R^{15}$ shows a phenyl group having no substituent or having substituents; and $R^{16}$ shows an aroyl group having no substituent or having substituents). Further, the present invention provides the intermediates of 2-fluorofucosyl-N-aroylglucosamine derivatives (hereinafter, sometimes referred to as "the second intermediate of the present invention") represented by the following general formula (5) as a useful synthetic intermediate of 2-fluorofucosyl-N-aroylglucosamine derivatives (namely, the Lewis X derivative, the present inventive derivatives) represented by the above general formula (1).

General formula (5):

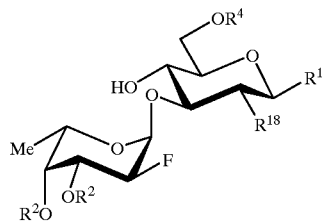

(wherein $R^1$, $R^2$ and $R^4$ in the above general formula (5) are the same as described above or in claim 1, and $R^{16}$ is the same as described above or in claim 15). Further, as the method for preparing the intermediates of 2-fluorofucosyl-N-aroylglucosamine derivatives (the first intermediate of the present invention) represented by the above general formula (4) with good reproductivity, the present invention provides a method for preparing the intermediate of 2-fluorofucosyl-N-aroylglucosamine derivatives (hereinafter, sometimes referred to as "the method for preparing the first intermediate of the present invention") by reacting the aroylglucosamine derivatives represented by the following general formula (i) with the compound represented by the above general formula (B').

General formula (i):

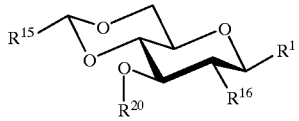

(wherein $R^1$, $R^{15}$ and $R^{16}$ in the above general formula (i) are the same as described above or in claim 15, and $R^{20}$ is the same as described above or in claim 8). Further, as the method for preparing the intermediates of 2-fluorofucosyl-N-aroylglucosamine derivatives (namely, the second intermediate of the present invention) represented by the above general formula (5) with good reproductivity, the present invention also provides a method for preparing the intermediate of the 2-fluorofucosyl-N-aroylglucosamine derivatives (hereinafter, sometimes referred to as "the method for preparing the second intermediate of the present invention") by cleaving a benzylidene ring of the intermediate of the 2-fluorofucosyl-N-aroylglucosamine derivatives represented by the above general formula (4). However, the concept represented by "the derivatives" includes the salts in the context of the present inventive derivatives, their intermediates (the first intermediate and the second intermediate of the present invention) and also these preparation methods (the method for preparing the present inventive derivatives and the method for preparing the first intermediates and the second intermediates of the present invention: hereinafter, sometimes referred to as merely "the present invention" as a general term).

EMBODIMENT OF THE PRESENT INVENTION

The derivatives of the present invention are particularly preferably the 2-fluorofucosyl-α-(1→3)-N-aroylglucosamine derivatives (or their salts) represented by the following general formula (2).

General formula (2):

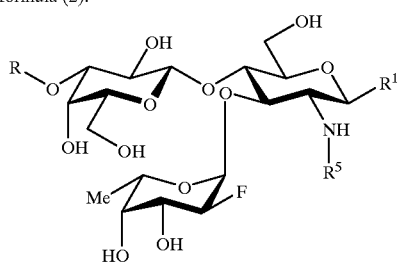

(wherein R in the above general formula (2) is a hydrogen atom, protecting group of the hydroxyl group, phosphate residue, sulfate residue or sialyl group represented by the following general formula (a').

General formula (a'):

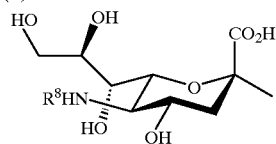

(wherein $R^8$ in the above general formula (a') shows an aliphatic acyl group). In addition, $R^1$ in the above general formula (2) is a hydrogen atom, hydroxyl group, C1–18 alkanoyloxy group having no substituent or having at least one of the following substituents, C7–15 aroyloxy group, C1–10 alkylthio group, arylthio group having no substituent or having the said one or more substituents, C1–18 alkoxy group, branched long chain alkoxy group, arylmethoxy group having no substituent or having the said one or more substituents, 2-trisilylethoxy group having C1–4 alkyl group or phenyl group or a group represented by the following general formula (b') or (c').

General formula (b'):

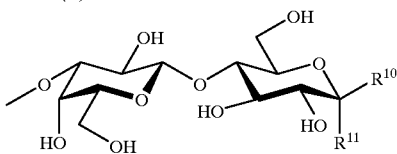

General formula (c'):

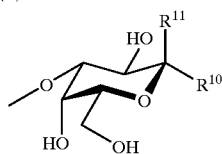

(wherein $R^{10}$ in the above general formulas (b') and (c') is a hydrogen atom, hydroxyl group, 2-trisilylethoxy group having C1–4 alkyl group or phenyl group, C1–30 alkoxy group, or sphingosine represented by the following general formula (d'); and $R^{11}$ is a hydrogen atom.

General formula (d'):

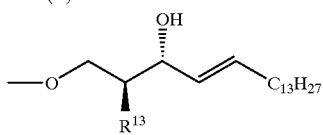

[(wherein $R^{13}$ in the above general formula (d') shows an azide, amine or NHCO $R^4$; and the said $R^{14}$ shows C15–25 alkyl group). Herein, in the event that the said $R^1$ has two or more said substituents in the above general formula (2), these substituents may be different from each other. These substituents are at least one group selected from the group comprising a halogen atom, trifluoromethyl group, hydroxyl group, C1–18 alkoxy group, aryloxy group, aryl group having a C1–10 alkyloxy group, amino group, aryl group having a C1–10 alkylamino group, monoamino group having a C1–18 alkyl group, diamino group having a C1–18 alkyl group, amino group having C1–18 alkyl group and C1–10 arylalkyl group, C1–18 alkanoylamino group, C7–15 aroylamino group, monocarbamoyl group having a C1–18 alkyl group, dicarbamoyl group having a C1–18 alkyl group, arylcarbamoyl group having a C1–10 alkyl group, carbamoyl group having a C1–18 alkyl group and a C1–10 arylalkyl group, arylcarbamoyl group, C1–18 alkanoyl group, C7–15 aroyl group, C1–18 alkylthio group, arylthio group, C1–18 alkylsulfonyl group, arylsulfonyl group, cyano group and nitro group.

Herein, the groups substituted one or two times on the alkyl chains or on the aryl rings of the above substituents are also included in the said substituents. In addition, $R^5$ is an aroyl group having no substituent or having substituents. Further, the derivatives of the present invention may be 2-fluorofucosyl-α-(1→3)-N-aroylglucosamie derivatives (or their salts) represented specifically by the following general formula (3).

General formula (3):

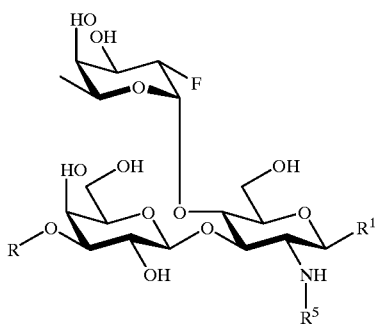

(wherein R and $R^5$ in the above general formula (3) are the same as described above, $R^1$ is a hydrogen atom, hydroxyl group, C1–10 alkanoyloxy group having no substituent or having at least one of the said substituents, C7–15 aroyl group, C1–10 alkylthio group, arylthio group having no substituent or having the said one or more substituents, C1–18 alkoxy group, branched long chain alkoxy group, arylmethoxy group having no substituent or having the said one or more substituents, or 2-trisilylethoxy group having C1–4 alkyl group or phenyl group or a group represented by the following general formula (b') or (c').

General formula (b'):

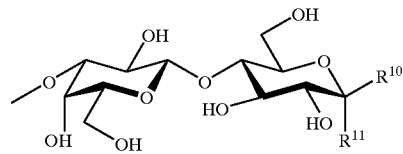

General formula (c'):

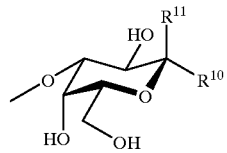

[wherein $R^{10}$ in the above general formulas (b') and (c') is a hydrogen atom, hydroxyl group, 2-trisilylethoxy group having a C1–4 alkyl group or a phenyl group, C1–30 alkoxy group or sphingosine represented by the following general formula (d'); and $R^{11}$ is a hydrogen atom.

General formula (d'):

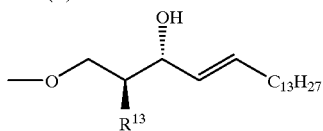

[(wherein $R^{13}$ in the above general formula (d') shows an azide, amine or NHCO $R^{14}$, and the said $R^{14}$ shows a C15–25 alkyl group). Herein, in the event that the said $R^1$ has the said two or more substituents in the above general formula (3), these substituents may be different from each other. Further, the said substituents are the same as described above and the groups substituted one or two times with the said substituents on the alkyl groups or on the aryl rings of the above substituents are also included in the said substituents. Further, as for the second intermediate of the present invention, the compound represented by the following general formula (5') is preferable.

General formula (5'):

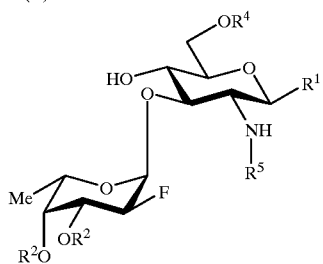

(wherein $R^2$ and $R^4$ in the said general formula. (5') may be the same or different from each other and show a hydrogen atom, C1–18 alkanoyl group, C7–15 aroyl group, or phenylmethyl group having no substituent or having substituents. In addition, $R^5$ shows the same as described above. Further, $R^1$ is a hydrogen atom, hydroxyl group, C1–18 alkanoyl group having no substituent or having at least one of the said substituents, C7–15 aroyl group, C1–10 alkylthio group, arylthio group having no substituent or having the said one or more substituents, C1–10 alkoxy group, branched long chain alkoxy group, arylmethoxy group having no substituent or having the said one or more substituents, 2-trisilylethoxy group having a C1–4 alkyl group or phenyl group or a group represented by the following general formula (b) or (c).

General formula (b):

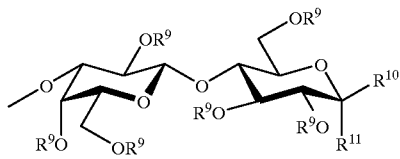

General formula (c):

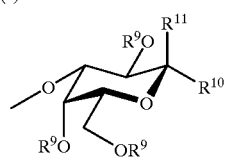

[wherein $R^9$ in the general formulas (b) and (c) shows a hydrogen atom, C1–18 alkanoyl group, C7–15 aroyl group, phenylmethoxy group having no substituent or having substituents; and $R^{10}$ is a hydrogen atom, hydroxyl group, 2-trisilylethoxy group having a C1–4 alkyl group or a phenyl group, C1–30 alkoxy group or sphingosine represented by the following general formula (d); and $R^{11}$ is a hydrogen atom.

General formula (d):

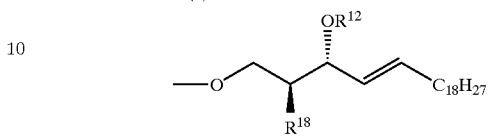

[(wherein $R^{12}$ in the above general formula (d) shows a hydrogen atom or benzoyl group; $R^{13}$ shows an azide, amine or NHCO $R^{14}$; and the said $R^{14}$ shows a C15–25 alkyl group). Herein, in the event that the said $R^1$ has the said two or more substituents in the above general formula (5'), these substituents may be different from each other. Herein, the said substituents are the same as described above. In addition, for the first intermediate of the present invention, the compound represented principally by the following general formula (4') is preferable.

General formula (4'):

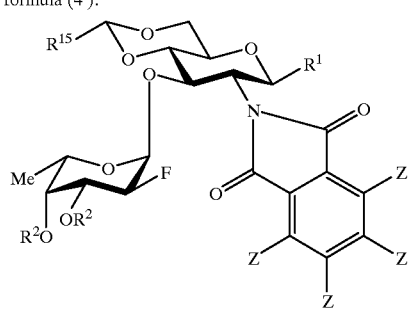

[wherein $R^{15}$ in the said general formula (4') shows a phenyl group having no substituent or having substituents, and Z shows a hydrogen atom or halogen atom (at least two may be the same or they may all be different.); in addition, $R^1$ and $R^2$ are the same as described above]. Herein, as for the first intermediate [said general formula (4)] and the second intermediate [said general formula (5)] of the present invention, the said $R^{16}$ may be one group selected from the group of a phthalimide ring group hereinafter, sometimes referred to as a "phthalimide group or phthalimide"), and a 2-naphthoylamide group and a 4-t-butylbenzoylamide group. Accordingly, the said $R^{16}$ of the compound represented by the said general formula (i) which is a precursor of the first intermediate of the present invention is preferably the same substituent as the aforementioned substituent. Further, the ring moieties of these groups may be hydrogen-reduced moieties. Next, the substituents of the present invention are illustrated as follows. The alkyl group having C1–18 in the said $R^1$ and substituents is a straight chained or a branched alkyl group, and is also a cycloalkyl group, (cycloalkyl) alkyl group or (cycloalkyl) cycloalkyl group and the like. Specifically, they are as follows: methyl group, ethyl group, propyl group, isopropyl group, butyl group, isobutyl group, 2-butyl group, t-butyl group, pentyl group, 3-pentyl group, isopentyl group, neopentyl group, hexyl group, heptyl group, 4-heptyl group, octyl group, nonyl group, 5-nonyl group, decyl group, undecyl group, 6-undecyl group, dodecyl group, tridecyl group, 7-tridecyl group, tetradecyl group, pentadecyl group, 8-pentadecyl group, hexadecyl group, heptadecyl group, 9-heptadecyl group, octadecyl group, cyclopropyl group, cyclobutyl group, cyclopentyl group, cyclohexyl group, cycloheptyl group, cyclooctyl group, cyclopentylmethyl group, cyclohexylmethyl group, (4-cyclohexyl) cyclohexyl group and the like.

Further, the aryl group having a C1–10 alkyl group in the said $R^1$ and substituents is a C1–10 phenylalkyl group; for example, a straight chained or a branched C1–10 alkyl group having a phenyl group at the terminal position. Specifically, they are a benzyl group, phenethyl group, phenylpropyl group, phenylbutyl group, phenylpentyl group, phenylhexyl group and the like. Further, the halogen atom in the said substituents and the said Z is for example a fluorine atom, chlorine atom, bromine atom or iodine atom. Further, the C1–18 alkoxy group in the said $R^1$ and the said substituents is a straight chain, a branching or cyclic alkoxy group: specifically a methoxy group, ethoxy group, propoxy group, isopropoxy group, butoxy group, pentyloxy group, cyclopentyloxy group, hexyloxy group, cyclohexyloxy group, heptyloxy group, octyloxy group, nonyloxy group, decyloxy group, undecyloxy group, dodecyloxy group, tridecyloxy group, tetradecyloxy group, pentadecyloxy group, hexadecyloxy group, heptadecyloxy group, octadecyloxy group, and the like.

In addition, the aryl in the said $R^1$ and the said substituents is formed by ring formation of any of a hydrocarbon, a hydrocarbon containing an oxygen atom, a hydrocarbon containing a sulfur atom, a hydrocarbon containing a nitrogen atom, or a hydrocarbon containing two nitrogen atoms. This ring means an aromatic ring which is a five-member monocyclic, a six-member monocyclic, a polycyclic fused ring fused from a six-member ring and a five-member ring, or a polycyclic fused ring fused from six-member rings. Namely, a monocyclic aromatic hydrocarbon group such as a phenyl group is: for example, a polycyclic fused aromatic hydrocarbon group such as a naphthyl group, anthracenyl group (anthryl group), or phenanthrenyl group; for example, aromatic heterocyclic groups such as a furyl group, thienyl group, pyridyl group, pyrazinyl group, benzofuranyl (benzo [b]furanyl) group, isobenzofuranyl (benzo [c] furanyl) group, benzothienyl (benzo[b]thienyl) group, isobezothienyl (benzo[c]thienyl) group, pyrimidinyl group, pyridadinyl group, quinolinyl group, isoquinolinyl group, quinoxalinyl group, naphthilidinyl group, phthalazinyl group or quinazolinyl group, which contain an oxygen atom, a sulfur atom or one or two nitrogen atoms. The position of the binding branch in forming such groups can be optionally selected from all possible positions. Further, a phenyl group is preferable for the aryl group in the said $R^1$. In addition, the C1–18 alkanoyl group in the said $R^1$, $R^2$, $R^4$, $R^9$ and the said substituents, or the C1–18 alkanoyl, means a straight chained or a branched alkylcarbonyl group or a cycloalkylcarbonyl group.

Specifically, they are a formyl group, acetyl group, propionyl group, butyryl group, isobutyryl group, valeryl group, isovaleryl group, pivaloyl group, pentanoyl group, isopentanoyl group, neopentanoyl group, hexanoyl group, heptanoyl group, octanoyl group, nonyl group, decanoyl group, undecanoyl group, dodecanoyl group, hexadecanoyl group, heptadecanoyl group, octadecanoyl group, cyclopentanecarbonyl group, cyclohexanecarbonyl group and the like. Further, the C1–18 alkanoylamino group in the said substituents is synonymous with an alkylcarboxamide group having C1–18, and the example is an amino group substituted with a straight chained or branched C1–18 alkanoyl or a cycloalkyl carbonyl. Specifically, they are an acetylamino group, propionylamino group, butylylamino group, valerylamino group, pentanoylamino group, cyclopentylcarboxamide group, cyclohexylcarboxamide group, heptanoylamino group, octanoylamino group, nonanoylamino group, decanoylamino group, undecanoylamino group, dodecanoylamino group, tridecanoylamino group, tetradecanoylamino group, pentadecanoylamino group, hexadecanoylamino group, heptadecanoylamino group, octadecanoylamino group and the like. Herein, the said substituents may be a monocarbamoyl group having a C1–18 alkyl group synonymous with a monoaminocarbonyl group having a C1–18 alkyl group, and the example is a carbonyl group substituted with a straight chain or branching alkylamino or cycloalkylamino. Specifically, they are a methylcarbamoyl group, ethylcarbamoyl group, propylcarbamoyl group, butylcarbamoyl group, pentylcarbamoyl group, cyclopentylcarbamoyl group, hexylcarbamoyl group, cyclohexylcarbamoyl group, heptylcarbamoyl group, octylcarbamoyl group, nonylcarbamoyl group, decylcarbamoyl group, undecylcarbamoyl group, dodecylcarbamoyl group, tridecylcarbamoyl group, tetradecylcarbamoyl group, pentadecylcarbamoyl group, hexadecylcarbamoyl group, heptadecylcarbamoyl group, octadecylcarbamoyl group, and the like.

Further, the dicarbamoyl group having a C1–18 alkyl group in the said substituents is synonymous with a diaminocarbonyl group having a C1–18 alkyl group, and the example is a dimethylcarbamoyl group, diethylcarbamoyl group and the like. Further, the groups substituted one or two times with the said substituents on the alkyl chains or on the aryl rings of the said substituents are also included in the said substituents. Namely, the groups specifically included in the said substituents are as follows: 2-(2-ethoxyethoxy)-3-oxapentyloxy group, 3,6-dioxaoctyloxy group, 3,6,9-trioxaundecyloxy group, 3,4,5-trimethoxybenzyloxy group, 2-benzyloxyethoxy group, 2-(3,4,5-trimethoxybenzyloxy) ethoxy group, 7-phenyl-3,6-dioxaheptyloxy group, 2-hydroxyethoxy group, 2-(2-hydroxyethoxy)-8-hydroxy-3,6-dioxaoctyloxy group, 1,1-hydroxy-3,6,9-trioxaundecyloxy group, and the like. The position substituted on the alkyl chains or on the aryl rings of the said substituents is possible on all the carbon atoms except on the carbon atoms directly bonding to the oxygen atoms of the reduced terminals in glycosides.

These substituents can substitute not only for one position on the alkyl chain or the aryl ring, but also for multiple position (especially 2–5). Further, in this case at least two of the kinds of substituents may be the same or they may all be different. In addition, the aroyl group having the substituents in the said $R^5$ means an aroyl group (arylcarbonyl group) which has on aromatic rings one or multiple substituents of one or multiple kinds of the following substituents. These substituents can be halogen atom, nitro group, trifluoromethyl group, a C1–18 alkyl group or a phenyl group including methyl group, ethyl group, propyl group, isopropyl group, butyl group, isobutyl group, t-butyl group, pentyl group, 3-pentyl group, isopentyl group, neopentyl group, hexyl group, heptyl group, 4-heptyl group, octyl group, nonyl group, 5-nonyl group, decyl group, undecyl group, 6-undecyl group, dodecyl group, tridecyl group, 7-tridecyl group, tetradecyl group, pentadecyl group, 8-pentadecyl group, hexadecyl group, heptadecyl group, 9-heptadecyl group, octadecyl group, cyclopropyl group, cyclobutyl group, cyclopentyl group, cyclohexyl group, cycloheptyl group, cyclooctyl group, cyclopentylmethyl group, cyclohexylmethyl group, (4-cyclohexyl) cyclohexyl group, and the like. Substituents can be a C1–18 alkoxy group exemplified as follows: a methoxy group, ethoxy group, propoxy group, butoxy group, pentyloxy group, cyclopentyloxy group, hexyloxy group, cyclohexyloxy group, heptyloxy group, octyloxy group, nonyloxy group, decyloxy group, undecyloxy group, dodecyloxy group, tridecyloxy group, tetradecyloxy group, pentadecyloxy group, hexadecyloxy group, heptadecyloxy group, octadecyloxy group, and the like.

Further, there can be a phenoxy group, benzyloxy group, benzyloxy group with substituents, amino group, benzylamino group, benzylamino group with substituents, C1–18 monoalkylamino group, each C1–18 dialkylamino group and alkylbenzylamino group with the C1–18 alkyl chain. The C1–18 alkanoylamino group (alkylcarboxamide group) can be exemplified as follows: an acetylamino group, propionylamino group, butylylamino group, valerylamino group, pentanoylamino group, cyclopentanecarboxamide group, hexanoylamino group, cyclohexanecarboxamide group, heptanoylamino group, octanoylamino group, nonanoylamino group, decanoylamino group, undecanoylamino group, dodecanoylamino group, tridecanoylamino group, tetradecanoylamino group, pentadecanoylamino group, hexadecanoylamino group, heptadecanoylamino group, octadecanoylamino group and the like. Further, there can be the C7–15 aroylamino group such as a benzoylamino group and a naphthoylamino group and the carboxyl group. The substituents may be C1–18 alkylcarbamoyl group (alkylaminocarbonyl group) in the alkyl chain are: for example, a methylcarbamoyl group, ethylcarbamoyl group, propylcarbamoyl group, butylcarbamoyl group, pentylcarbamoyl group, cyclopentylcarbamoyl group, hexylcarbamoyl group, cyclohexylcarbamoyl group, heptylcarbamoyl group, octylcarbamoyl group, nonylcarbamoyl group, decylcarbamoyl group, undecylcarbamoyl group, dodecylcarbamoyl group, tridecylcarbamoyl group, tetradecylcarbamoyl group, pentadecylcarbamoyl group, hexdecylcarbamoyl group, heptadecylcarbamoyl group, octadecylcarbamoyl group, and the like. Further, other substituents are an arylcarbamoyl group, a C1–18 alkylthio group, an arylthio group, a C1–18 alkylsulfonyl group, an arylsufonyl group, a cyano group, and the like. Further, the C1–10 alkyl group in the said $R^6$ is a straight chained or branched alkyl group and specifically a methyl group, ethyl group, propyl group, isopropyl group, butyl group, isobutyl group, t-butyl group, pentyl group, 3-pentyl group, isopentyl group, neopentyl group, hexyl group, and the like. Further, the C1–10 alkanoyl group or the C1–10 alkanoyl in the said $R^1$, $R^2$, $R^3$, $R^4$, $R^7$, $R^8$ and $R^9$ is a straight chained or branched C1–10 alkylcarbonyl, and the alkyl moiety may be substituted with one or multiple halogen atoms and the like. Specifically, these substituents are a formyl group, acetyl group, chloroacetyl group, dichloroacetyl group, propionyl group, butyryl group, isobutyryl group, valeryl group, isovaleryl group, pivaloyl group, pentanoyl group, isopentanoyl group, neopentanoyl group and the like; specifically an acetyl group, a chloroacetyl group, a trichloroacetyl group and the like are preferable. Further, the aroyl group or aroyl in the said $R^1$, $R^2$, $R^3$, $R^4$, $R^5$, $R^7$ and $R^9$ is synonymous with an arylcarbonyl group, and the aryl moiety may be an aryl group having substituents such as described in the aryl group relating to the said $R^1$ and the said substituents.

Further, the phenylmethyl group having the substituents in the said $R^2$, $R^3$ and $R^4$ means a benzyl group which has a halogen atom, a nitro group, an alkoxy group with 1–6 carbon atoms and the like on the phenyl ring, and specifically is a 4-fluorobenzyl group, 4-nitrobenzyl group, 4-methoxybenzyl group or the like. Specifically the 4-methoxybenzyl group is preferable. Further, the 2-trisilylethoxy group which has a C1–4 alkyl group or a phenyl group in the said $R^1$ and $R^{10}$ means a 2-silylethoxy group of which the same or different kinds of the C1–4 alkyl group or the phenyl group are substituted for all three on the silicon atom. Specifically, this is a 2-trimethylsilylethoxy group, 2-triethylsilylethoxy group, 2-(triisopropylsilyl)ethoxy group, 2-(t-butyldimethylsilyl)ethoxy group, 2-(triisopropylsilyl)ethoxy group, 2-triphenylsilylethoxy group, 2-(t-butyldiethylsilyl)ethoxy group, 2-(diphenylmethylsilyl)ethoxy group, 2-(t-butyldiphenylsilyl)ethoxy group and the like. Further, the said $R^{17}$ and $R^{18}$ in the said general formulas (A') and (B') are, for example: an acyloxy group and aroyloxy group such as OAc and OBz; an alkylthio group and arylthio group such as SMe, SEt and SPh; an alkylsulfoxide group and arylsulfoxide group such as S(O)Me, S(O)Et and S(O)Ph; a trichloroacetoimidate group represented by OC(=NH)CCl$_3$; a halogen atom represented by F, Br, Cl and I; a 4-pentenyloxy group represented by O—(CH$_2$)$_3$CH=CH$_2$; a phenylselenyl group represented by SePh; a dialkylphosphate group and diarylphosphate group such as O—P(O) (OMe)$_2$, O—P(O) (OEt)$_2$ and O—P(O) (OPh)$_2$; a dialkylphophite group and a diarylphosphite group such as O—P(OMe)$_2$, O—P(OEt)$_2$ and O—P(OPh)$_2$; a diphenylphophineimidate group such as represented by O—P(=NTs)(NPh$_2$)$_2$; a tetramethylphosphoroamidate group represented by O—P(O) (NMe$_2$)$_2$ and the like. Further, the said $R^{19}$ and $R^{20}$ are, for example, a hydrogen atom, trialkylsilane group and triarylsilane group such as SiMe$_3$, SiEt$_3$ and SiPh$_3$. Furthermore, the present inventive derivative [2-fluorofucosyl-α-(1→3 or 1→4)-N-aroylglucosamine derivative] may, for example, form salts which are sodium salts, lithium salts, potassium salts, magnesium salts and calcium salts and the like. The above general formulas relate specifically to 2-fluorofucosyl-α-(1→3 or 1→4)-N-aroylglucosamine derivatives represented, for example, by the following chemical structural formulas (α), (β), (γ) and (δ). Herein, "Ac" means an acetyl group in the following formulas. Moreover, these compounds have not been published in the literature yet and can provide derivatives which exhibit excellent inhibitory activity to selectin adhesion and metabolic stability.

Structural formula (α):

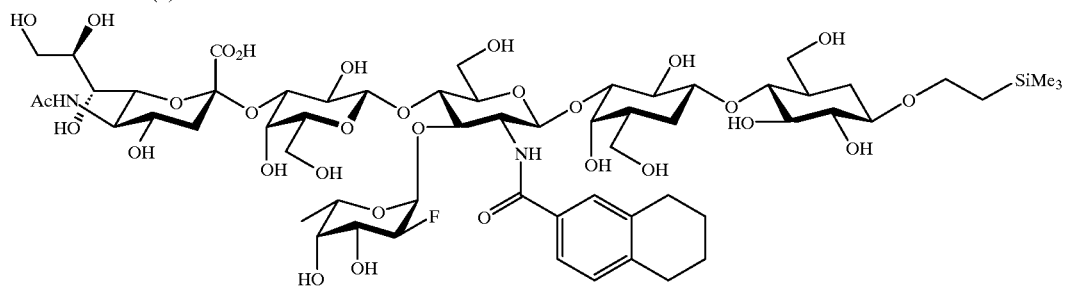

Structural formula (β):

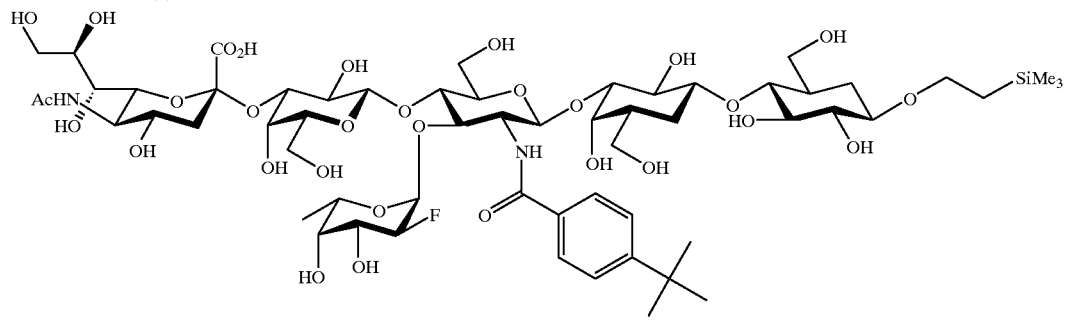

Structural formula (γ):

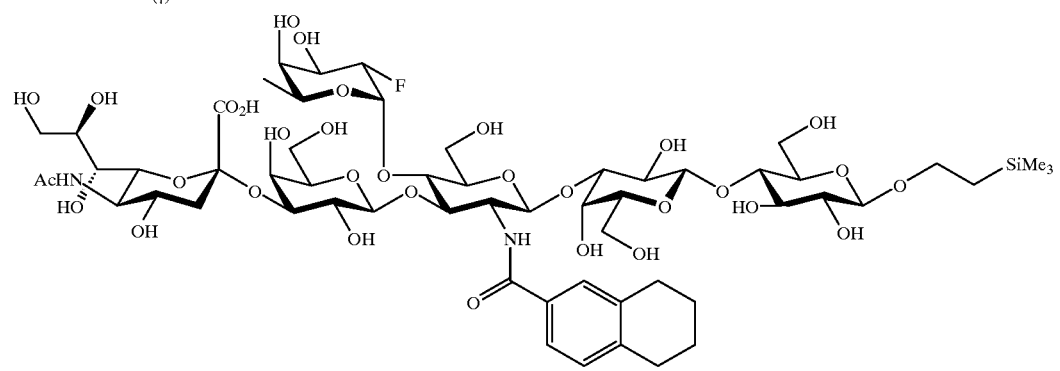

Structural formula (δ):

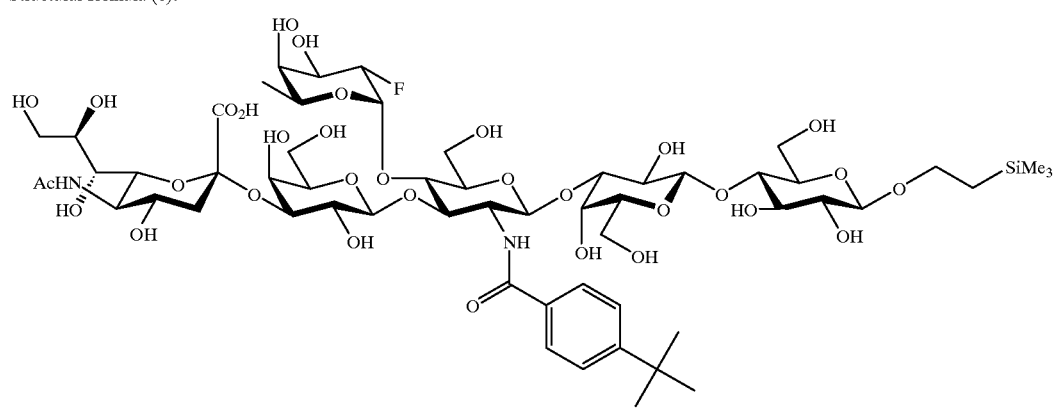

Next, the examples relating to the present inventive derivatives, their intermediates and these preparation methods are illustrated. The fundamental skeleton for the present inventive 2-fluorofucosyl-α-(1→3 or 1→4)-N-aroylglucosamine derivative as a fluorine-substituted Lewis X derivative comprises a galactose moiety, 2-fluorofucose moiety and N-aroylglucosamine moiety as understood from the said general formula (1) and the said structural formulas (α), (β), (γ) and (δ). Further, the preparation of the present inventive derivatives, for example, includes the methods wherein debenzylation is performed by catalytically hydrogenating the protected sialyl Lewis X derivative by the use of Pd—C/$H_2$, the resulting induction into the sialyl Lewis X derivative according to the present invention which has the aroylamide in the glucosamine moiety. Such methods have been first found by the inventors. To avoid this catalytic reduction, an enzymatic method for synthesizing the skeleton is known, for example, while according to the present invention, it is possible to obtain the sialyl Lewis X derivative containing an aroylglucosamine by a non-enzymatic method. First, the 2-fluorofucosyl-α-(1→3)-N-aroylglucosamine derivative represented by the said structural formulas (α) and (β) is illustrated. For this derivative, an example of a method for preparing a new fluorine-containing fucosylglucosamine lactoside derivative is as follows. First, the compound represented by the following structural formula (10) is synthesized followed by introduction into the compounds represented by the following structural formulas (11) and (12). Then, reaction with a sialyl-galactose moiety represented by the following structural formula (13) leads to the sialyl Lewis X glycoside [structural formula (14)]. Herein, "Bn" in the formulas means a benzyl group and "Bz" means a benzoyl group (hereinafter, referred to as the same).

Structural formula (10):

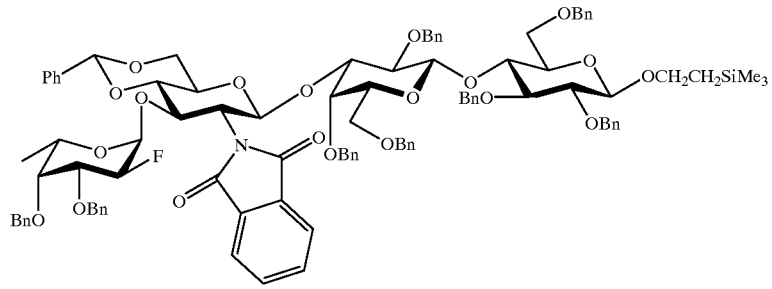

Structural formula (11):

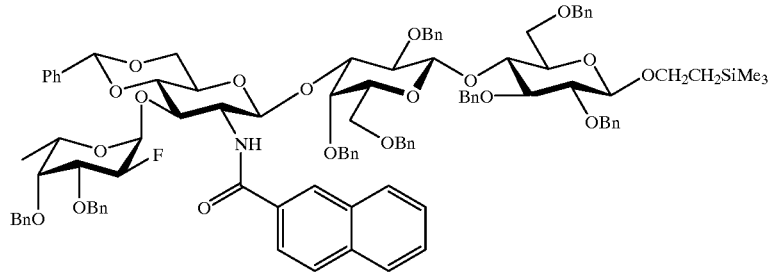

Structural formula (12):

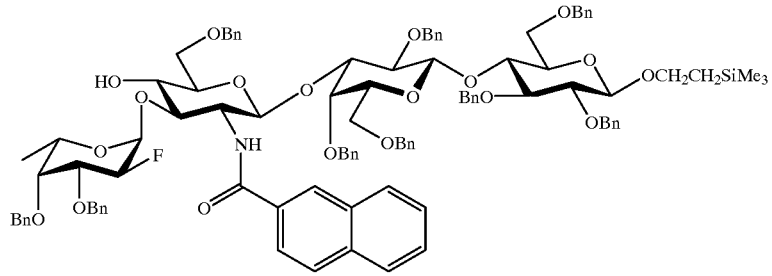

Structural formula (13):

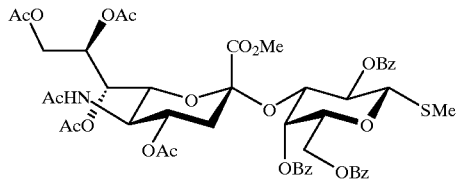

Structural formula (14):

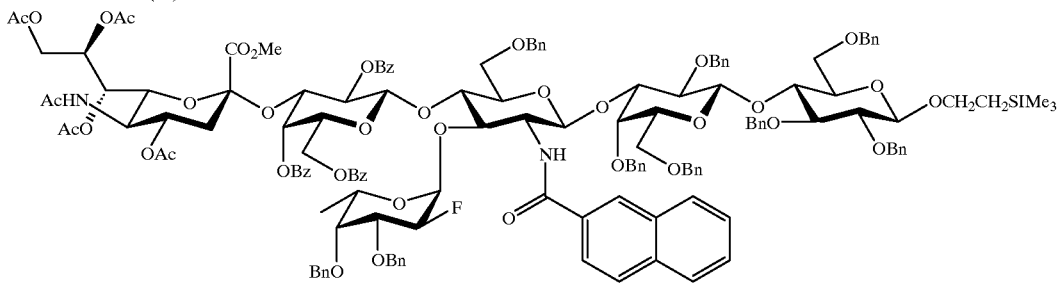

Catalytic reduction and acetylation of the compound shown in structural formula (14) can lead to the sialyl Lewis X glycoside derivative [structural formula (15)] in which the naphthalene moiety is reduced.

Structural formula (15):

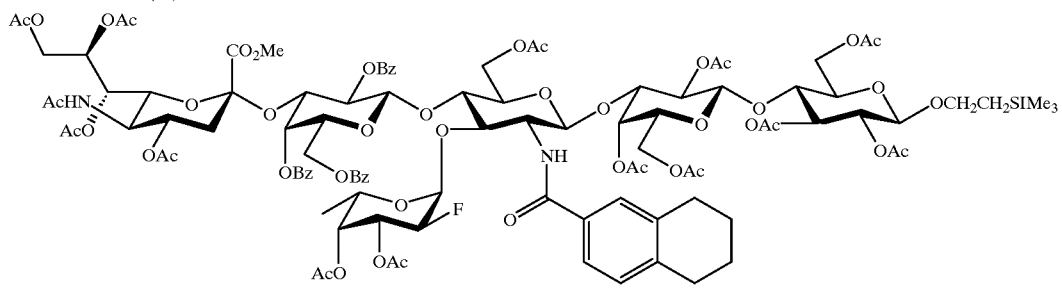

Continuously, deacetylation and alkaline hydrolysis can lead to the 2-fluorofucosyl-N-aroylgulucosamine derivative [structural formula (α)] can be obtained according to the present invention.

Structural formula (α):

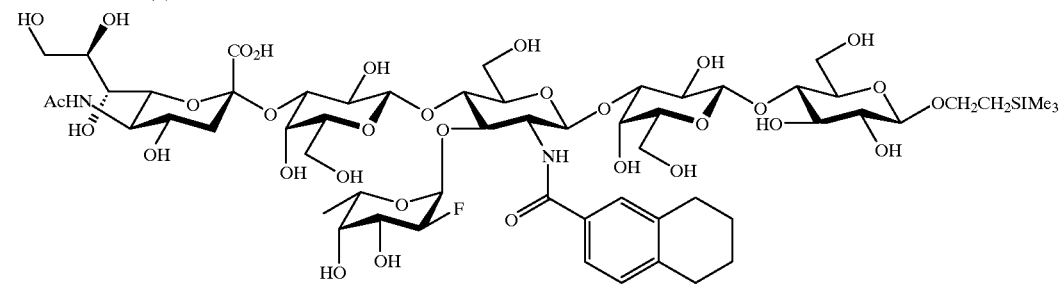

In addition, the sialyl Lewis X glycoside derivative [structural formula (15)] can lead to a sialyl Lewis X ganglioside derivative by introducing a lipid, or so-called ceramide, according to the method described in the Journal of Carbohydrate Chemistry; 10 (1991) 549–560. Moreover, the compound represented by structural formula (10) can lead to the compound represented by structural formulas (16) and (17), and after introducing the sialylgalactose [structural formula (13)], the sialyl Lewis X glycoside [structural formula (18)] can be obtained.

Structural formula (16):

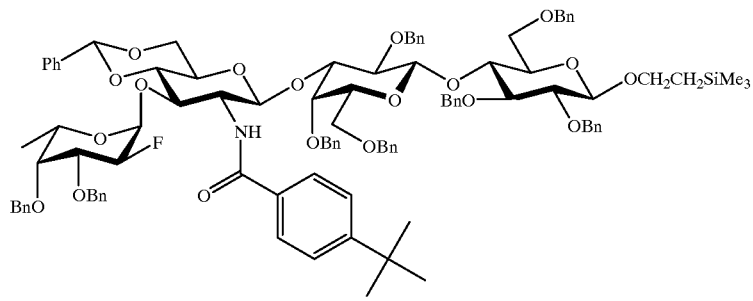

Structural formula (17):

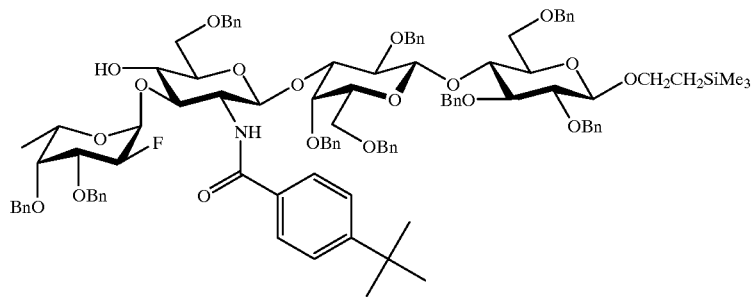

Structural formula (18):

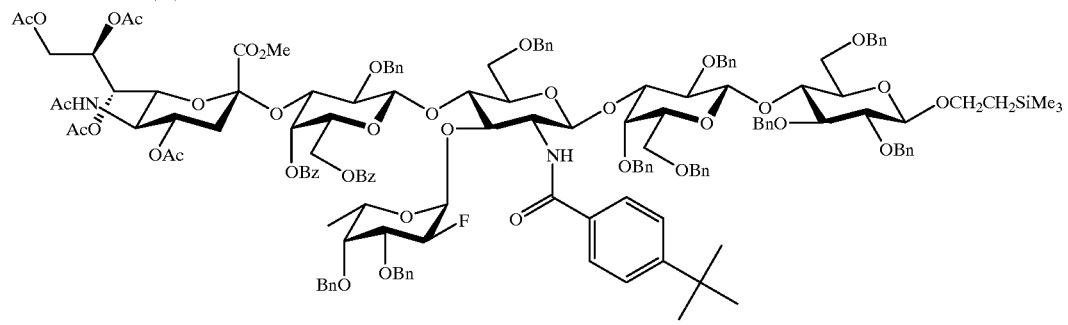

By conducting catalytic reduction, acetylation, deacetylation and alkaline hydrolysis of the compound represented by structural formula (18), the 2-fluorofucosyl-N-aroylglucosamine derivative [structural formula (β)] according to the present invention can be prepared.

shown in structural formula (α) is illustrated, referring to the following Reaction Schemes 1 and 2. In this reaction process, 2-(trimethylsikyl)ethyl O-(4,6-O-benzylidene-2-deoxy-2-phthalimid-β-D-glucopyranosyl)-(1→3)-O-(2,4,6-tri-O-benzyl-β-D-galactopyranosyl)-(1→4)-2,3,6-tri-O-

Structural formula (β):

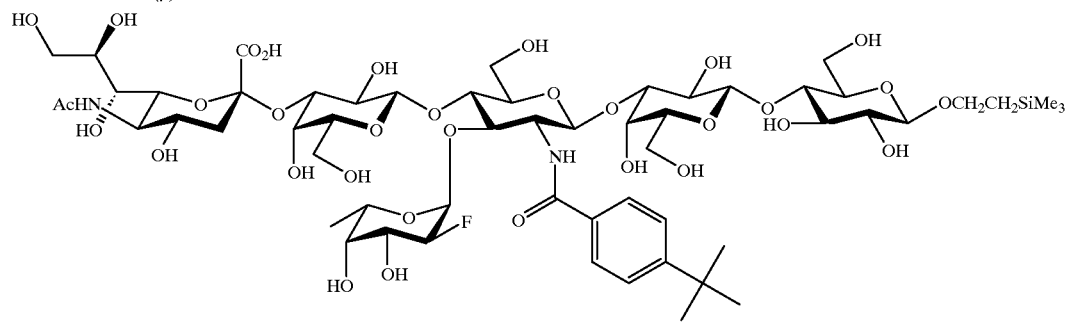

Next, the example of the preparation method for the 2-fluorofucosyl-N-aroylglucosamine derivative, [2-fluorofucosyl-α-(1→3)-N-aroylglucosamine derivative] benzyl-β-D-glucopyranoside [said structural formula (e)] can be used as a starting material. This compound can be synthesized according to the method described in Carbohydrate Research, 200 (1990) 269–285.

First, as shown in the following Reaction Scheme 1, by reacting methyl 3,4-di-O-benzyl-2-deoxy-2-fluoro-1-thio-L-fucopyranoside represented by the said structural formula (f) (for the preparation method: refer to JP Opening No. 9-052902) with the compound represented by the said structural formula (e) using dimethyl(methylthio)sulfonium triflate (DMTST) as a reaction promotor, the α-glycoside derivative [structural formula (10)] can be obtained [reaction process (a)]. Next, after dephthalimidation of this α-glycoside and subsequent 2-naphthoylation [structural formula (11)] [reaction process (b)], by performing a reductive cleavage of the benzylidene group [structural formula (12)] [reaction process (c)] and then introducing a sialylgalactose moiety [structural formula (13)] to (12) [reaction process (d)], the sialyl Lewis X hexose [structural formula (14): corresponding to general formula (1) of the present invention] can be obtained. However, the compound represented by the said (13) is the same as the compound represented by the said structural formula (g) (hereinafter, refer to the same).

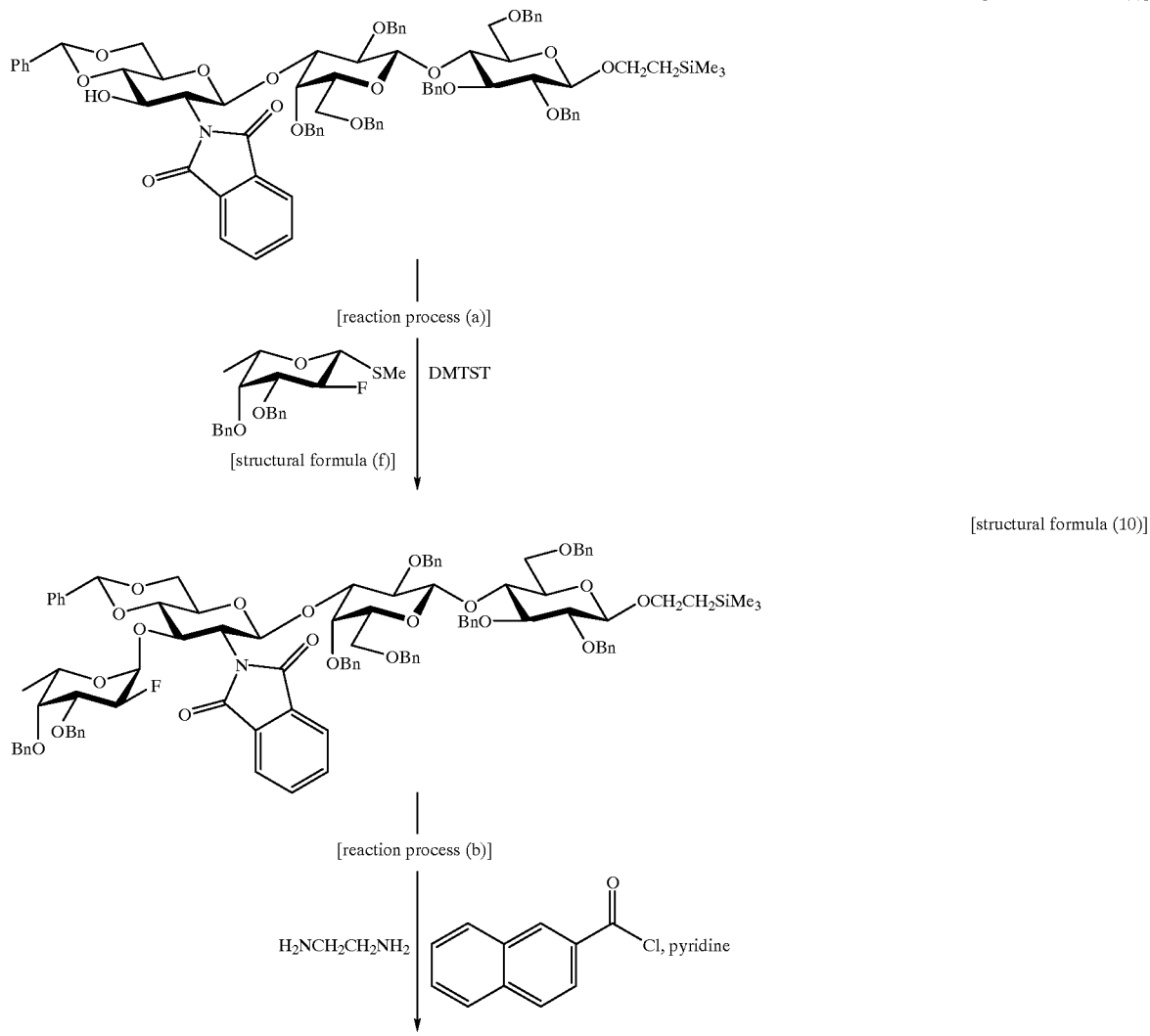

-continued
[structural formula (11)]
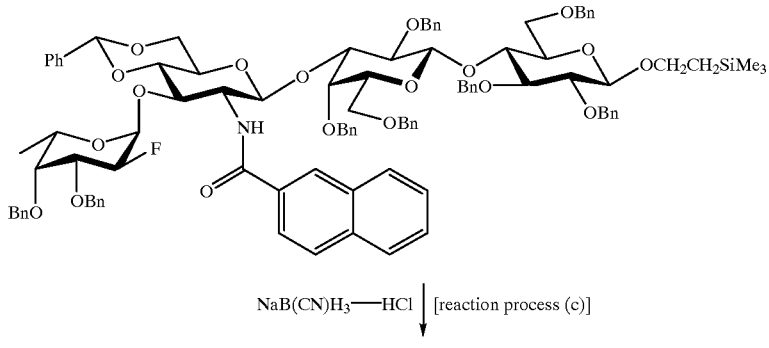
[structural formula (12)]
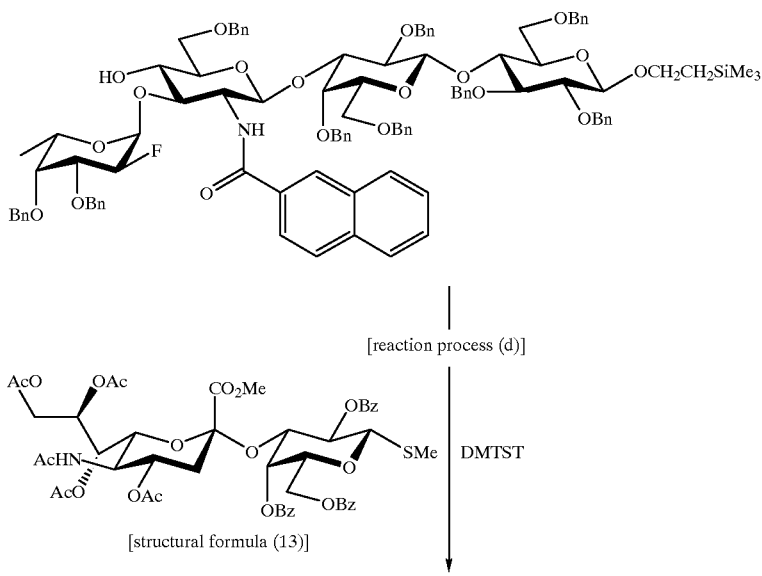
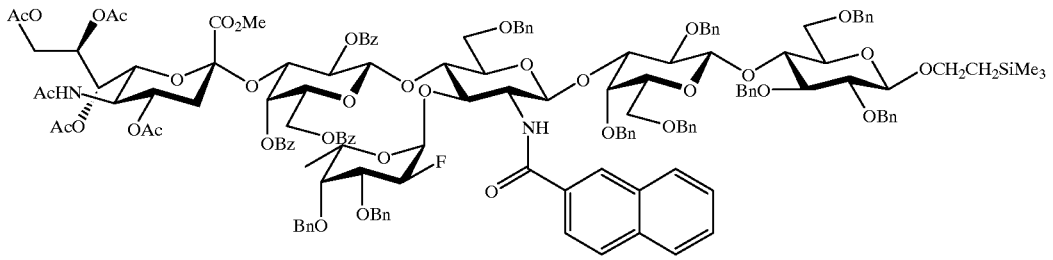
Further, as shown in the following Reaction Scheme 2, by catalytically reducing the compound represented by structural formula (14) [reaction process (e)] followed by acetylation, the derivative of which naphthalene moiety is reduced [structural formula (15)] can be obtained.

Finally, one of the present objective compounds, which is represented by structural formula (α), can, for example, be obtained by treating with sodium methoxide and sodium hydroxide [reaction process (f)].

glucopyranoside [structural formula (e)] with methyl 3,4-di-O-benzyl-2-deoxy-2-fluoro-1-thio-L-fucopyranoside [strucural formula (f)] in a reaction-inert solvent (e.g. benzene, toluene, methylene chloride or a mixture of these

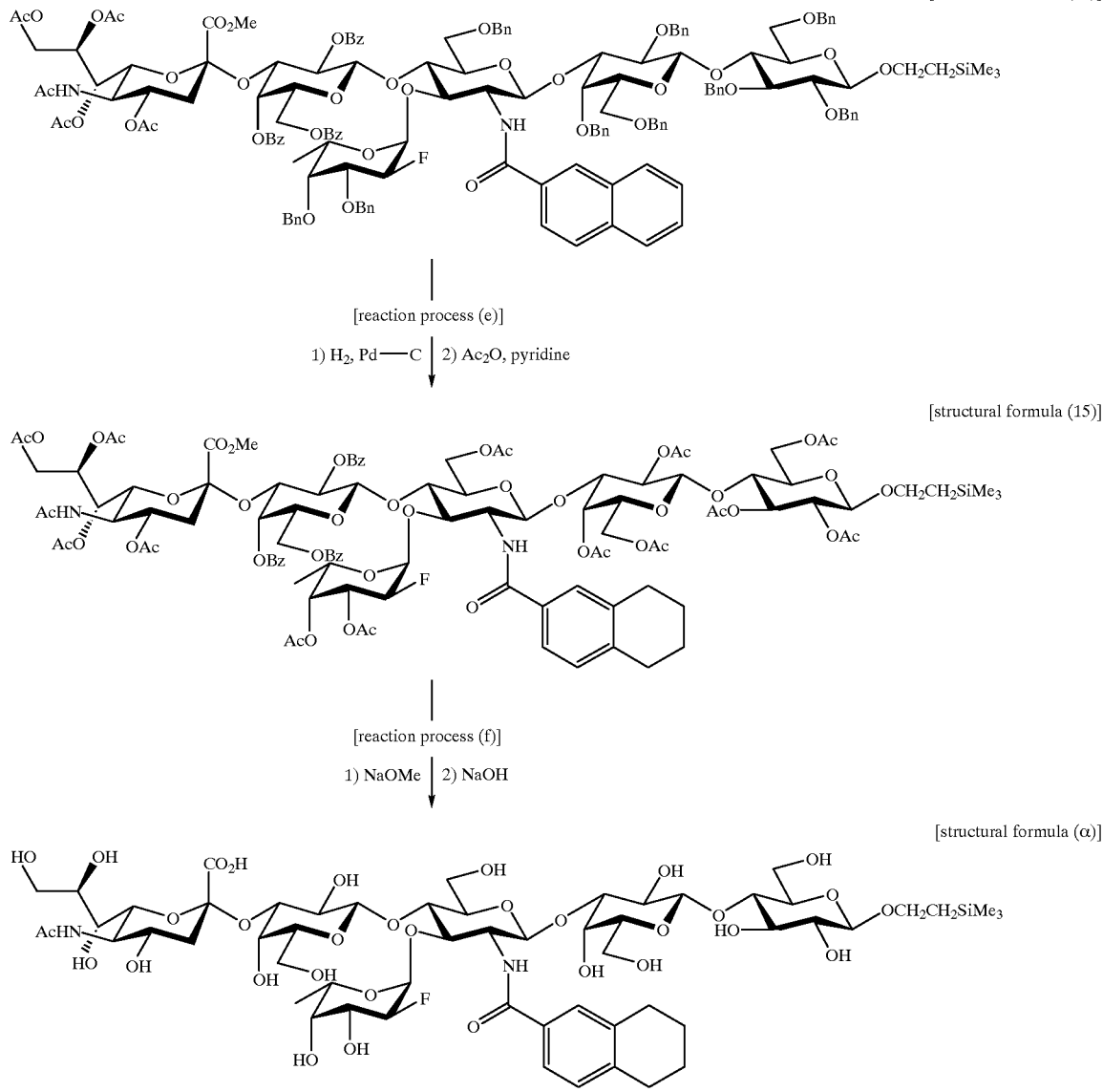

In the reaction described above, although reduction of the naphthalene ring takes place, by appropriately modifying the substituents $R^1$ and $R^4$ in general formula (1) and further changing the group represented by general formula (B), it is possible to obtain a compound naphthalene moiety of which is not reduced partially. For this reason, the said $R^1$ may be ethyl-2,4,6-tri-O-acetyl-β-D-galactoside-3-oxyl group; the said $R^4$ may be acetyl groups and the said $R^2$ may be Bn for the said general formula (B), for example. Next, the Reaction Schemes 1 and 2 are more specifically illustrated. First, in the reaction process (a), by treating 2-(trimethylsikyl) ethyl O-(4,6-O-benzylidene-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D- solvents) at 5° C.–10° C. for 2 hr in the presence of an appropriate glycosylation catalyst (e.g. N-iodosuccinimide/scandium trifluoromethanesulfonate, N-iodosuccinimide/tetrabutylammonium triflate, dimethyl(methylthio)sulfonium triflate (DMTST), N-iodosuccinimide/trifluoromethanesulfonic acid, silver trifluoromethanesulfonate/methylsulfenyl bromide and the like) and synthetic zeolite (molecular sieves) etc., the reaction can lead to the first intermediate of the present invention which is the compound represented by the following general formula (4'). Herein, the compound represented by this general formula (4') is corresponding to the compound represented by structural formula (10).

General scheme (4'):

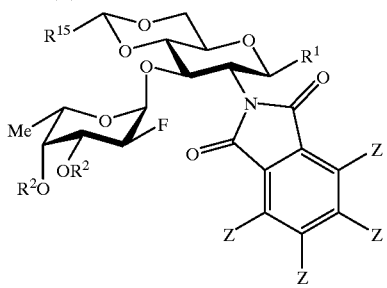

[wherein $R^{15}$ in the said general formula (4') shows a phenyl group having no substituent or having substituents, Z comprises at least two identical or all different groups selected from hydrogen atoms or halogen atoms, in addition, $R^1$ and $R^2$ are the same as described above]. Next, in the reaction process (b), removing the phthalimide of the glucosamine moiety by treating it in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents) in the presence of a deprotective agent for the phthalimide (e.g. hydrazine, ethylene diamine or their mixture) at 30° C.–100° C. for 6–24 hr, without or after purification, by reacting 2-naphthoyl chloride with the above product in the presence of a basic organic catalyst (e.g. dimethylaminopyridine, diethylaminopyridine, 1,8-diazabicyclo[5,4,0]-7-undecene, 1,5-diazabicyclo[4,3,0 ]-5-nonene or their mixture, etc.) used as an acylation condition in a basic organic solvent (e.g. trimethylamine, pyridine γ-lutidine, pyperidine, N-methylmorpholine, or a mixture of these solvents, etc.) at 5° C.–50° C., the above product can be converted to the resulting naphthoylated form which is the compound (one of the first intermediates of the present invention) represented by structural formula (11).

Further, in the reaction process (c), by cleaving the benzylidene moiety of the compound represented by the said structural formula (11) using a reductive cleaving reagent (e.g. sodium cyanoborohydride-hydrogen chloride, borane trimethylamine complex-aluminum chloride, borane dimethylamine complex-boron trifluoride ether complex and the like) in a reaction-inert solvent (e.g. diethyl ether, tetrahydrofuran, acetonitrile, propionitrile, benzene, toluene, methylene chloride, or a mixture of these solvents, etc.), the compound (one of the second intermediate of the present invention) represented by structural formula (12) can be obtained. Furthermore, in the reaction process (d), because all hydroxyl groups of the glucosamine moiety in the compound represented by structural formula (12) are protected with benzoyl groups and the like, except the hydroxyl group at the 4-position, by introducing sialylgalactose [structural formula (13)] in the presence of the said glycosylation accelerator, the resulting compound [which is included in the present inventive derivatives represented by general formula (1)] represented by structural formula (14) can be obtained. This sialylgalactose can be introduced by treating it in a reaction-inert solvent (e.g. benzene, toluene, methylene chloride, dichloroethane, diethyl ether, tetrahydrofuran, or a mixture of these solvents, etc.) at 5° C.–35° C. for 12–24 hr in the presence of an appropriate glycosylation accelerator (e.g. N-iodosuccinimide/scandium trifluoromethanesulfonate, N-iodosuccinimide/ tetrabutylammonium triflate, dimethyl(methylthio) sulfonium triflate (DMTST), N-iodosuccinimide/ trifluoromethanesulfonic acid, silver trifluoromethanesulfonate/methylsulfenyl bromide and the like) and synthetic zeolite (molecular sieves), etc.

Further, in the reaction process (e), by removing the benzyl group of the obtained sialyl Lewis X glycoside by reacting it in a reaction-inert solvent (e.g. methanol, ethanol, n-propanol, isopropanol, ethyl acetate, methyl acetate, acetic acid or a mixture of these solvents, etc.) in the presence of the catalysts for catalytic reduction (e.g. palladium—carbon, palladium hydroxide—carbon, palladium—barium sulfate, etc.) using a hydrogen donor (e.g. hydrogen gas, cyclohexene, cyclohexadiene, formic acid, ammonium formate salts, etc.) at 0° C.–50° C. for 10–120 hr, and by acetylating the generated free hydroxyl group in a basic organic solvent (e.g. pyridine, triethylamine, γ-lutidine, piperidine, N-methylmorpholine or a mixture of these solvents, etc.) using an acetylating agent (e.g. acetic anhydride, acetyl chloride, and the like) at 0° C.–60° C. for 2–40 hr, the compound represented by structural formula (15) can be obtained [which is included in the present inventive derivative represented by general formula (1)]. Further, in the reaction process (f), by reacting benzoyl group (Bz) and acetyl group (Ac) as protective groups of a hydroxyl group with an alkaline metal alkoxide or alkalineearthmetal alkoxide (e.g. sodium methoxide, sodium ethoxide, sodium t-butoxide, lithium methoxide, magnesium methoxide, calcium methoxide, and the like), or alkaline metal hydroxides and alkalineearthmetal hydroxides (e.g. sodium hydroxide, lithium hydroxide, potassium hydroxide, magnesium hydroxide, calcium hydroxide, and the like) in a protic solvent (e.g. water, methanol, ethanol, n-propanol, isopropanol, n-butanol, t-butanol or a mixture of these solvents, etc.) at 0° C.–40° C. for 2–48 hr, the compound represented by structural formula (α) as 2-fluorofucosyl-α-(1→3)-N-tetrahydronaphthylglucosamine derivative according to the present invention can be obtained.

Further, the example method to prepare the present inventive derivatives represented by the above structural formula (β) are illustrated referring to the following Reaction Schemes 3 and 4. In this reaction process, 2-(trimethylsikyl) ethyl O-(2-deoxy-3,4-di-O-benzyl-2-fluoro-α-fucopyranosyl)-(1→3)-O-(4,6O-benzylidene-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-glucopyranoside [structural formula (10)] can be used as starting material. First, as shown in the following Reaction Scheme 3, after dephthalimidation of the compound represented by structural formula (10), by 4-t-butylbenzoylation [structural formula (16)] [reaction process (g)] followed by reductive cleavage of the benzylidene group [structural formula (17)] [reaction process (h)], and introduction of sialylgalactose moiety [structural formula (13)] into (17) [reaction process (i)], sialyl Lewis X hexose [structural formula (18) corresponding to general formula (1) of the present invention] can be obtained.

Reaction Scheme 3
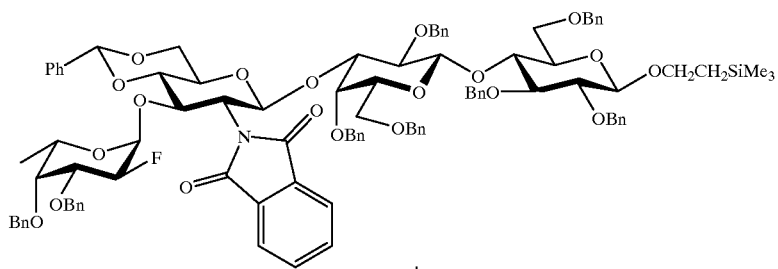
[structural formula (10)]
[reaction process (g)]
H₂NCH₂CH₂NH₂
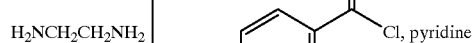
Cl, pyridine
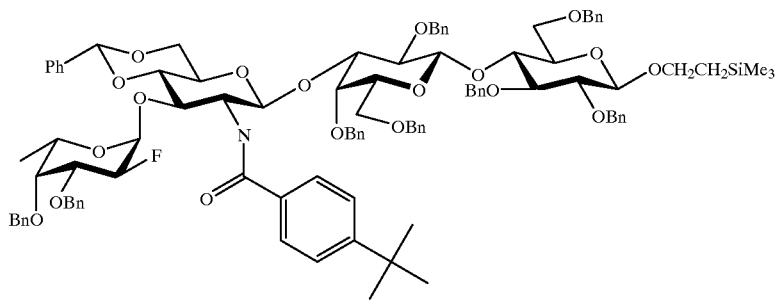
[structural formula (16)]
NaB(CN)H₃, HCl  [reaction process (h)]
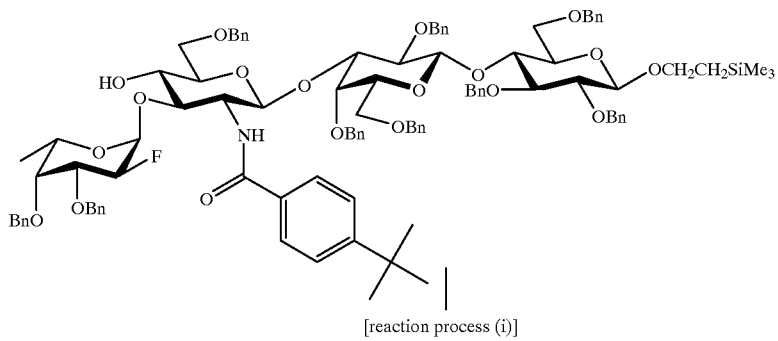
[structural formula (17)]
[reaction process (i)]
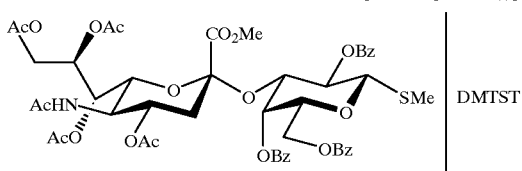
DMTST
[structural formula (13)]

-continued

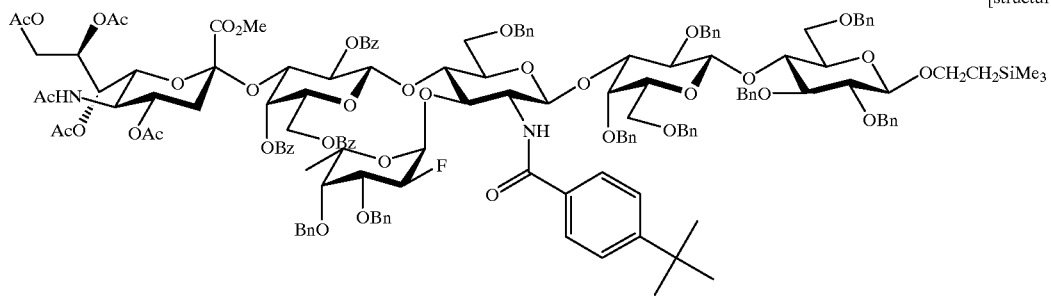

[structural formula (18)]

Further, as shown in the following Reaction Scheme 4, the derivative [structural formula (19)] can be obtained by catalytic reduction of the compound represented by structural formula (18) [reaction process (i)] followed by acetylation. Finally, one of the object compounds represented by structural formula (β) of the present invention can be obtained, for example, by treating with sodium methoxide, sodium hydroxide and the like [reaction process (k)].

Reaction Scheme 4

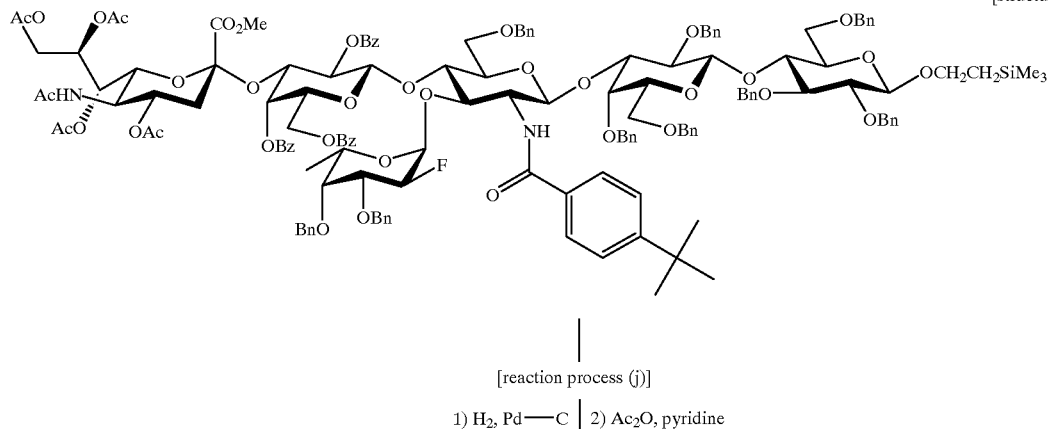

[structural formula (18)]

[reaction process (j)]
1) $H_2$, Pd—C  2) $Ac_2O$, pyridine

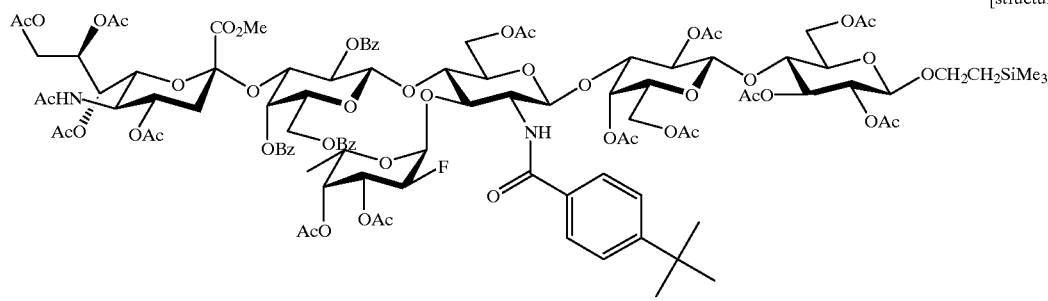

[structural formula (19)]

[reaction process (k)]
1) NaOMe  2) NaOH

-continued

[structural formula (β)]

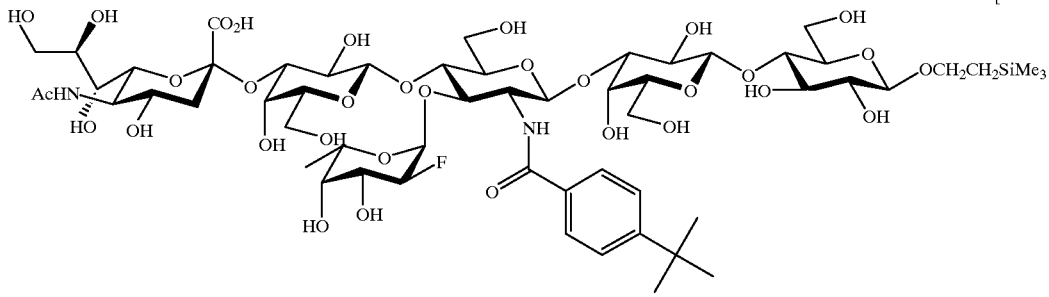

Next, the Reaction Schemes 3 and 4 are illustrated in detail. First, in the reaction process (g), removing the phthalimide of the glucosamine moiety by treating the compound represented by structural formula (10) in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents) in the presence of a deprotective agent for the phthalimide (e.g. hydrazine, ethylene diamine or their mixture) at 30° C.–100° C. for 6–24 hr, without or after purification, by reacting 4-t-butylbenzoyl chloride with the above product in the presence of a basic organic catalyst (e.g. dimethylaminopyridine, diethylaminopyridine, 1,8-diazabicyclo[5,4,0]-7-undecene, 1,5-diazabicyclo[4,3,0]-5-nonene or their mixture, etc.) used as an acylation condition in a basic organic solvent (e.g. trimethylamine, pyridine, γ-lutidine, pyperidine, N-methylmorpholine, or a mixture of these solvents, etc.) at 5° C.–50° C., the above product can be converted to the resulting 4-t-butylbenzoylated form which is the compound (one of the first intermediates of the present invention) represented by structural formula (16). Further, in the reaction process (h), by cleaving the benzylidene moiety of the compound represented by the said structural formula (16) using a reductive cleaving reagent (e.g. sodium cyanoborohydride-hydrogen chloride, borane trimethylamine complex-aluminum chloride, borane dimethylamine complex-boron trifluoride ether complex and the like) in a reaction-inert solvent (e.g. diethyl ether, tetrahydrofuran, acetonitrile, propionitrile, benzene, toluene, methylene chloride, or a mixture of these solvents, etc.), the compound (one of the second intermediates of the present invention) represented by structural formula (17) can be obtained.

Further, in the reaction process (i), because all hydroxyl groups of the glucosamine moiety in the compound represented by structural formula (17) are protected with benzoyl groups and the like, except the hydroxyl group at the 4-position, by introducing sialylgalactose [structural formula (13)] in the presence of the said glycosylation promotor, the resulting compound [which is included in the present inventive derivatives represented by general formula (1)] represented by structural formula (18) can be obtained. This sialylgalactose can be introduced by treating it in a reaction-inert solvent (e.g. benzene, toluene, methylene chloride, dichloroethane, diethyl ether, tetrahydrofuran, or a mixture of these solvents, etc.) at 5° C.–35° C. for 12–24 hr in the presence of an appropriate glycosylation promotor (e.g. N-iodosuccinimide/scandium trifluoromethanesulfonate, N-iodosuccinimide/tetrabutylammonium triflate, dimethyl(methylthio)sulfonium triflate (DMTST), N-iodosuccinimide/trifluoromethanesulfonic acid, silver trifluoromethanesulfonate/methylsulfenyl bromide and the like) and synthetic zeolite (molecular sieves), etc.)

Further, in the reaction process (j), by removing the benzyl group of the obtained sialyl Lewis X glycoside by reacting in a reaction-inert solvent (e.g. methanol, ethanol, n-propanol, isopropanol, ethyl acetate, methyl acetate, acetic acid or a mixture of these solvents, etc.) in the presence of a catalyst for catalytic reduction (e.g. palladium—carbon, palladium hydroxide—carbon, palladium—barium sulfate) using hydrogen donors (e.g. hydrogen gas, cyclohexene, cyclohexadiene, formic acid, ammonium formate salts, etc.) at 0° C.–50° C. for 10–120 hr, and by acetylating the generated free hydroxyl group in a basic organic solvent (e.g. pyridine, triethylamine, γ-lutidine, piperidine, N-methylmorpholine or a mixture of these solvents, etc.) using an acetylating agent (e.g. acetic anhydride, acetyl chloride, and the like) at 0° C.–60° C. for 2–40 hr, the compound represented by structural formula (19) can be obtained [which is included in the present inventive derivative represented by general formula (1)]. Finally, in the reaction process (k), byreacting the benzoyl group (Bz) and acetyl group (Ac) as protective groups of a hydroxyl group with an alkaline metal alkoxide or alkalineearthmetal alkoxide (e.g. sodium methoxide, sodium ethoxide, sodium t-butoxide, lithium methoxide, magnesium methoxide, calcium methoxide, and the like), or an alkaline metal hydroxide or alkalineearthmetal hydroxide (e.g. sodium hydroxide, lithium hydroxide, potassium hydroxide, magnesium hydroxide, calcium hydroxide, and the like) in a protic solvent (e.g. water, methanol, ethanol, n-propanol, isopropanol, n-butanol, t-butanol or a mixture of these solvents, etc.) at 0° C.–40° C. for 2–48 hr, the compound represented by structural formula (β) as 2-fluorofucosyl-α-(1→3)-N-4-t-butylbenzoylglucosamine derivative according to the present invention can be obtained. Next, the 2-fluorofucosyl-α-(1→4)-N-aroylglucosamine derivative represented by the formulas (γ) and (δ) is illustrated as follows. After synthesizing the compound represented by structural formula (21) from the compound represented by structural formula (20) referring to the method described in Carbohydrate Research, 200, 269–285 (1990), this derivative can be led to the compound represented by the said structural formula (γ) and the compound represented by the said structural formula (δ) according to the present invention.

Namely, after synthesizing the compound represented by structural formula (21) referring to the Journal of Carbohydrate Chemistry, 13, 641–654 (1994), the objective compounds of the present invention represented by the said structural formulas (γ) and (δ) can be obtained. The compound represented by structural formula (21) can be obtained by deacetylation, dephthalimidation and 2-naphthoylation of the known compound, 2-(trimethylsikyl)ethyl O-(3,4,6-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-glucopyranoside [structural formula (20)] as a starting material. Further, as shown in structural formula (22), after introduction of the benzylidene group, the compound represented by structural formula (23) can be obtained by reductive cleavage of this moiety.

Structural formula (20):

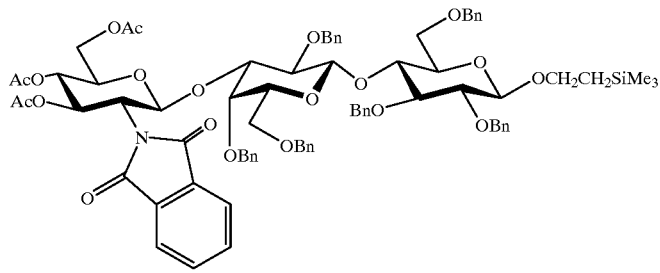

Structural formula (21):

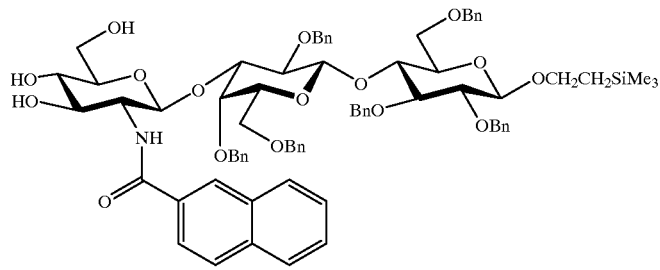

Structural formula (22):

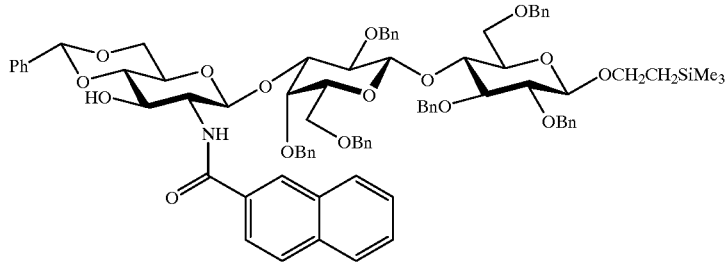

Structural formula (23):

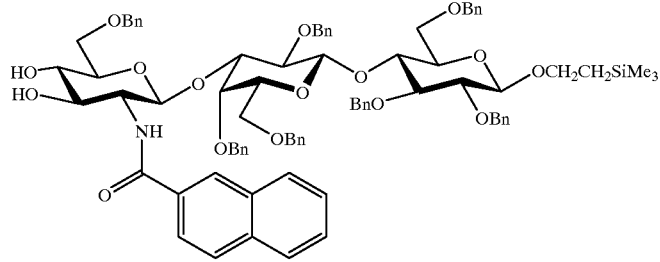

Further, in introducing the compound which becomes the sialylgalactose moiety represented by the following structural formula (13), silver trifluoromethanesulfonate/ methylsulfenyl bromide, for example, can be used.

Structural formula (13):

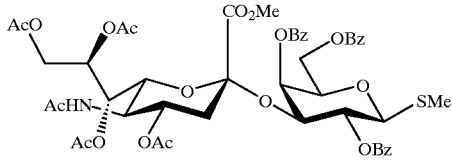

Furthermore, α-glycoside derivatives can be obtained by reaction of the only one remaining hydroxyl group with methyl 3,4-di-O-benzyl-2-deoxy-2-fluoro-1-thio-L-fucopyranoside using, for example, N-iodosuccinimide/ trifluoromethanesulfonic acid as a reaction promotor. Thus, sialyl Lewis a hexose (which corresponds to general formula (1) of the present invention) represented by the following structural formula (24) can be obtained. In addition, catalytic reduction and acetylation of the compound represented by the said structural formula (24) can lead to the derivative represented by structural formula (25) where the naphthalene moiety of the compound (24) is reduced. Finally, the 2-fluorofucosyl-N-aroylglucosamine derivative represented by structural formula (γ) which is one of the objective compounds of the present invention can be obtained by treating with sodium methoxide, sodium hydroxide and the like.

Structural formula (24):

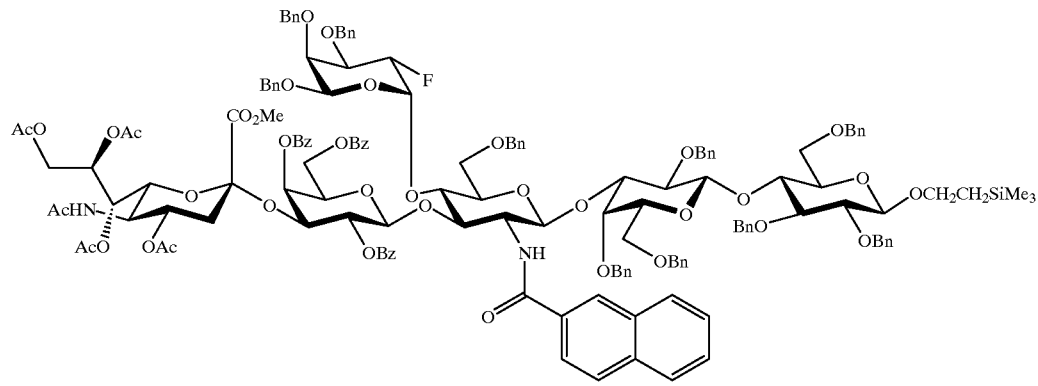

Structural formula (25):

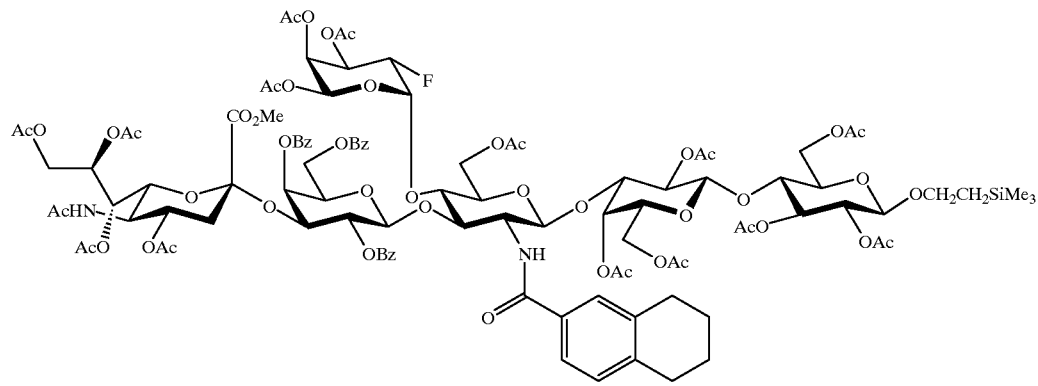

Structural formula (γ):

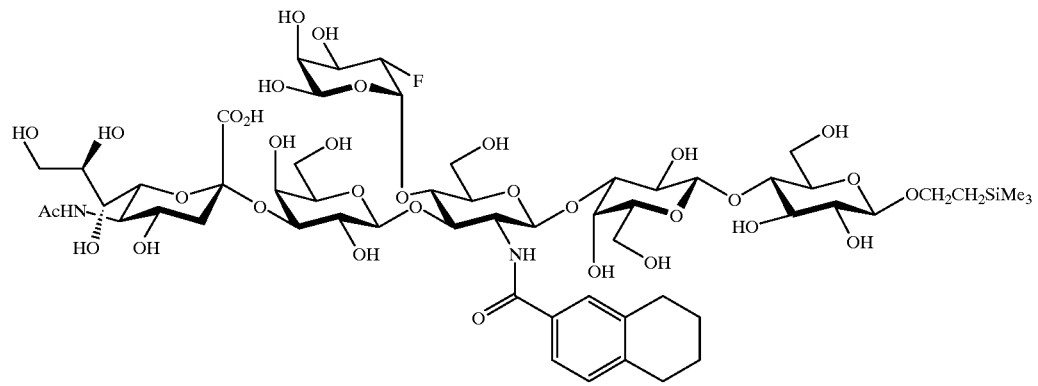

Further, the sialyl Lewis a glycoside represented by structural formula (25) can be led to sialyl Lewis a ganglioside derivatives by introducing the lipid, a so-called ceramide, referring to the method described in the Journal of Carbohydrate Chemistry, 13, 641–654 (1994). Further, starting from the compound represented by structural formula (20), after introducing a benzylidene group [structural formula (27)] into the compound represented by structural formula (26) which is obtained from deacetylation, dephthalimidation and 4-t-butylbenzoylation, by reductive cleavage of this moiety the compound represented by structural formula (28) can be obtained.

Structural formula (13):

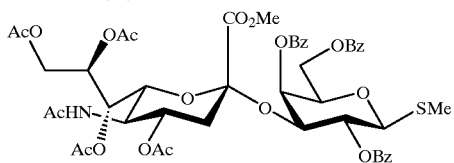

Furthermore, α-glycoside derivatives can be obtained by reaction of the only one remaining hydroxyl group with Structural formula (26):

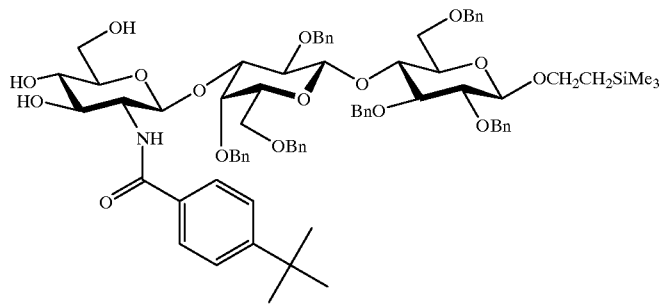

Structural formula (27):

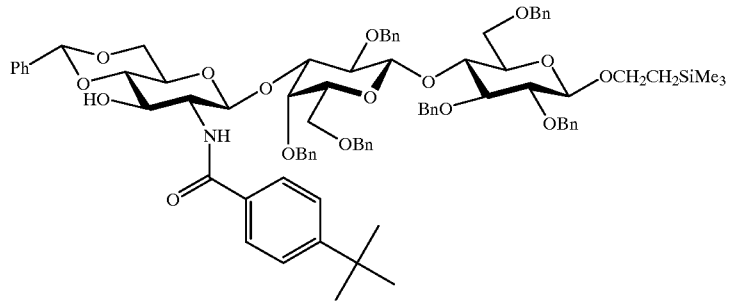

Structural formula (28):

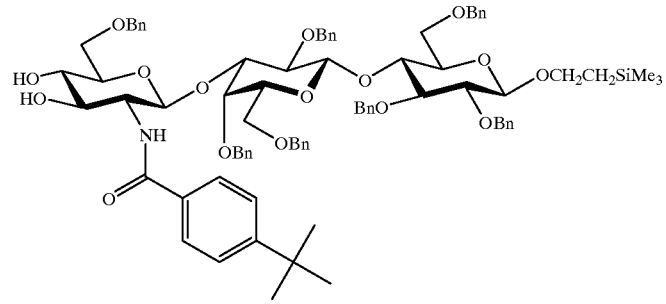

Further, in introducing the compound which becomes the sialylgalactose moiety represented by the following structural formula (13), silver trifluoromethanesulfonate/methylsulfenyl bromide, for example, can be used.

methyl 3,4-di-O-benzyl-2-deoxy-2-fluoro-1-thio-L-fucopyranoside using, for example, N-iodosuccinimide/trifluoromethanesulfonic acid as a reaction promotor. Thus, sialyl Lewis a hexose (which corresponds to general formula (1) of the present invention) represented by the following structural formula (29) can be obtained. In addition, catalytic reduction and acetylation of the compound represented by the said structural formula (29) can lead to the derivative represented by structural formula (30) where its naphthalene moiety is reduced. Finally, the 2-fluorofucosyl-N-aroylglucosamine derivative represented by structural formula (δ) which is one of the objective compounds of the present invention can be obtained by treating with sodium methoxide, sodium hydroxide and the like.

Structural formula (29):

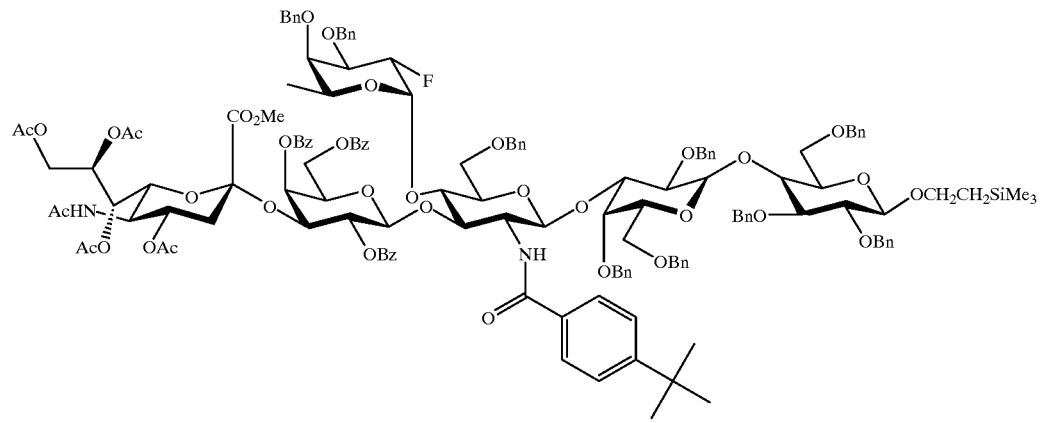

Structural formula (30):

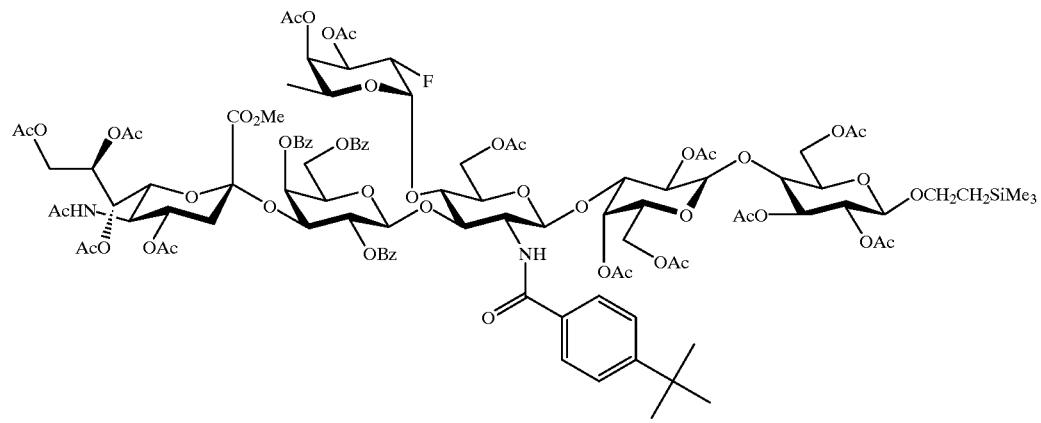

Structural formula (δ):

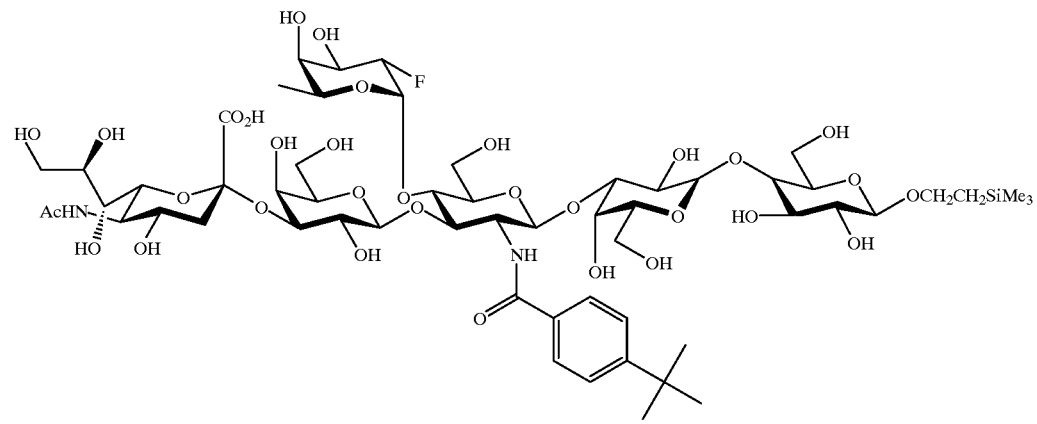

Further, the sialyl Lewis a glycoside represented by structural formula (30) can be led to sialyl Lewis a ganglioside derivatives by introducing the lipid, a so-called ceramide, referring to the method described in the Journal of Carbohydrate Chemistry, 13, 641–654 (1994).

Next, the 2-fluorofucosyl-α-(1→4)-N-tetrahydronaphthylglucosamine derivative as shown in structural formula (γ) can be prepared by the reaction process as shown in the following Reaction Schemes 5 and 6. In this reaction process, 2-(trimethylsikyl)ethyl O-(3,4,6-tri-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-glucopyranoside [structural formula (20)] can be used as a starting material. This compound is synthesized by the method described in Carbohydrate Research; 200, 269–285 (1990). The compound represented by the above structural formula (20) corresponds to the compound represented by the above structural formula (h). First, as shown in the Reaction Scheme 5, after deacetylation and dephthalimidation of this compound [structural formula (20)], this process comprises 2-naphthoylation of this compound [structural formula (21), reaction process (l)] followed by introduction of a benzylidene group [structural formula (22), reaction process (m)]. Next, performing reductive cleavage of the benzylidene group [structural formula (23), reaction process (n)], then introducing the sialylgalactose moiety represented by structural formula (13), and finally by reacting with methyl 3,4-di-O-benzyl-2-deoxy-2-fluoro-1-thio-L-fucopyranoside [reaction process (o)] using, for example, N-iodosuccinimide/trifluoromethanesulfonic acid as a reaction promotor, the sialyl Lewis a hexose [corresponding to the derivative represented by general formula (1) of the present invention] represented by structural formula (24) can be obtained.

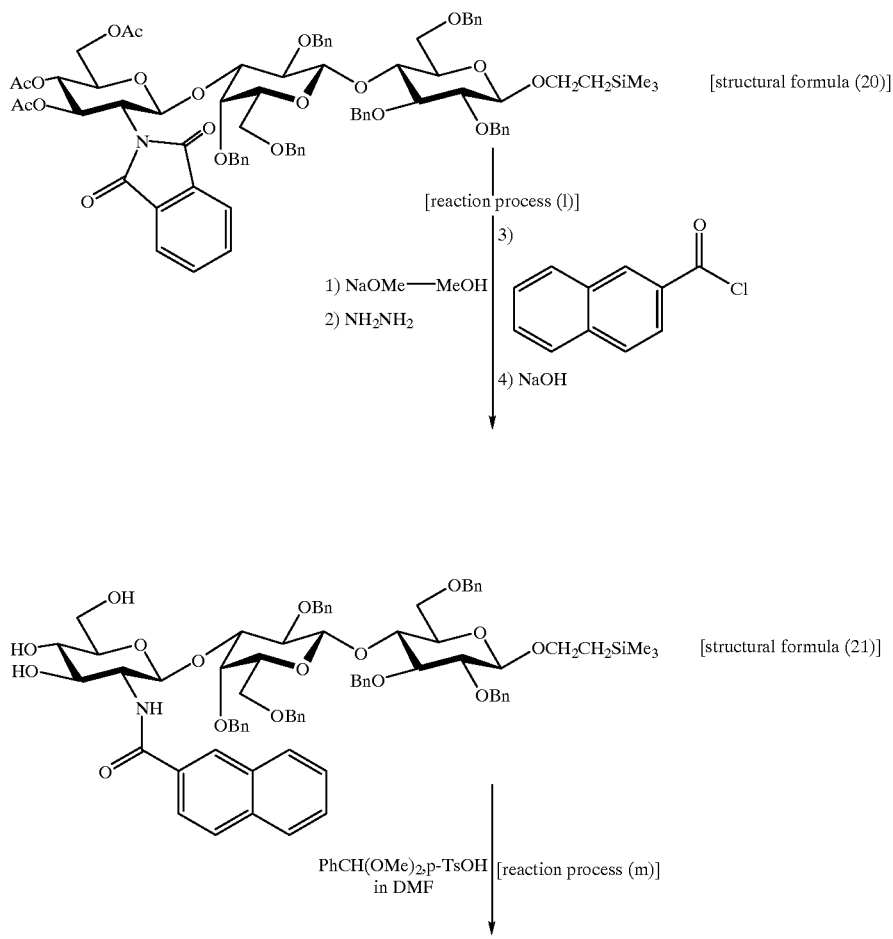

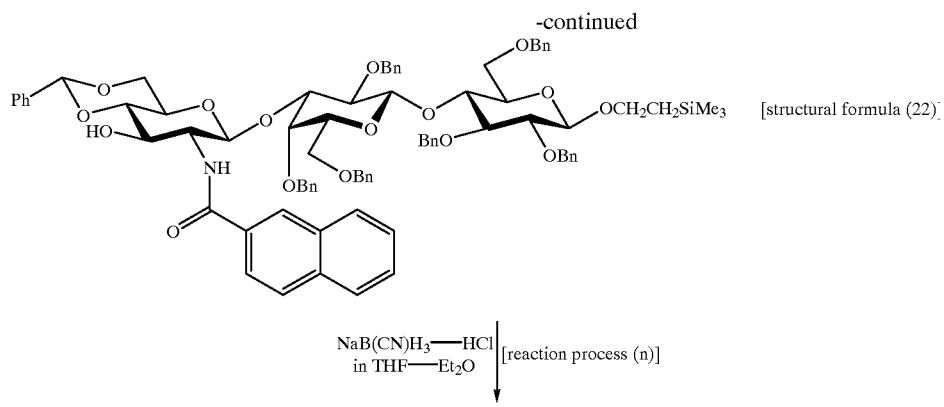

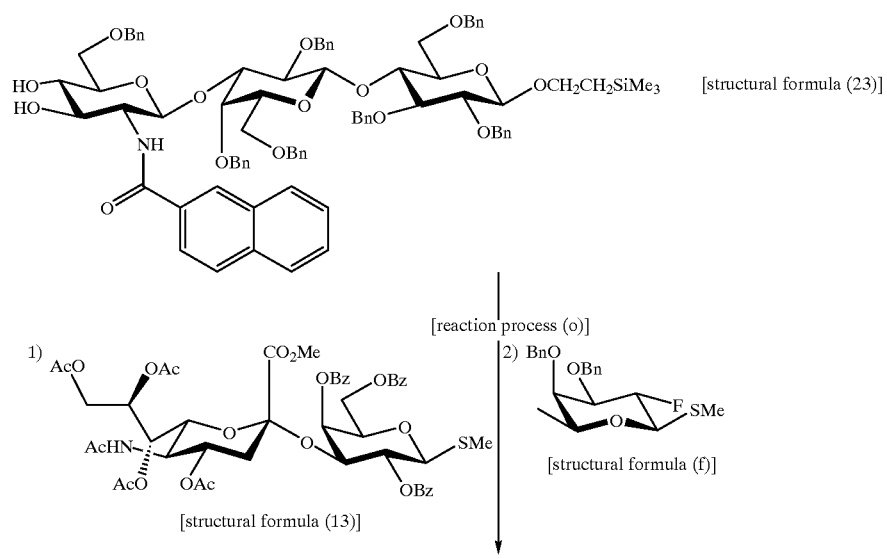

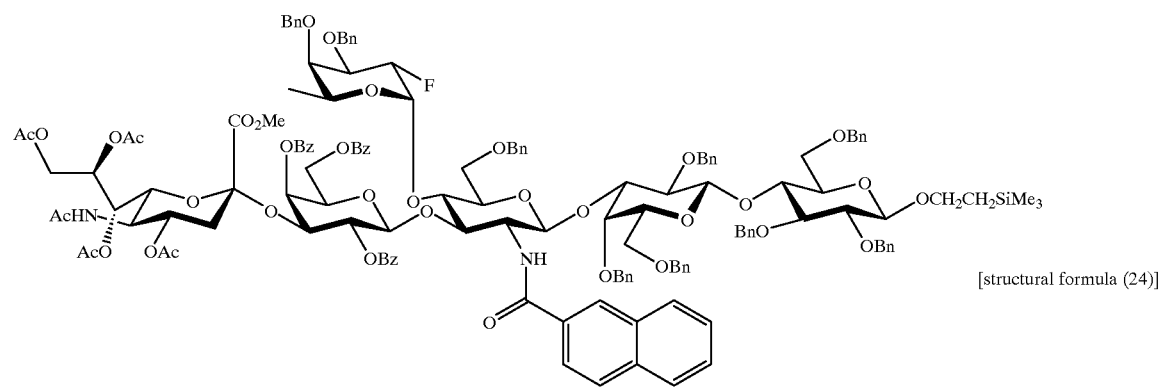

In addition, as shown in the following Reaction Scheme 6, performing catalytic reduction [reaction process (p)] of the compound represented by structural formula (24) followed by acetylation, can lead to the derivative represented by structural formula (25) where its naphthalene moiety is partially reduced. Finally, the derivative represented by structural formula (γ) which is one of the objects of the present invention, can be obtained by treating with sodium methoxide, sodium hydroxide and the like [reaction process (q)].

Reaction Scheme 6

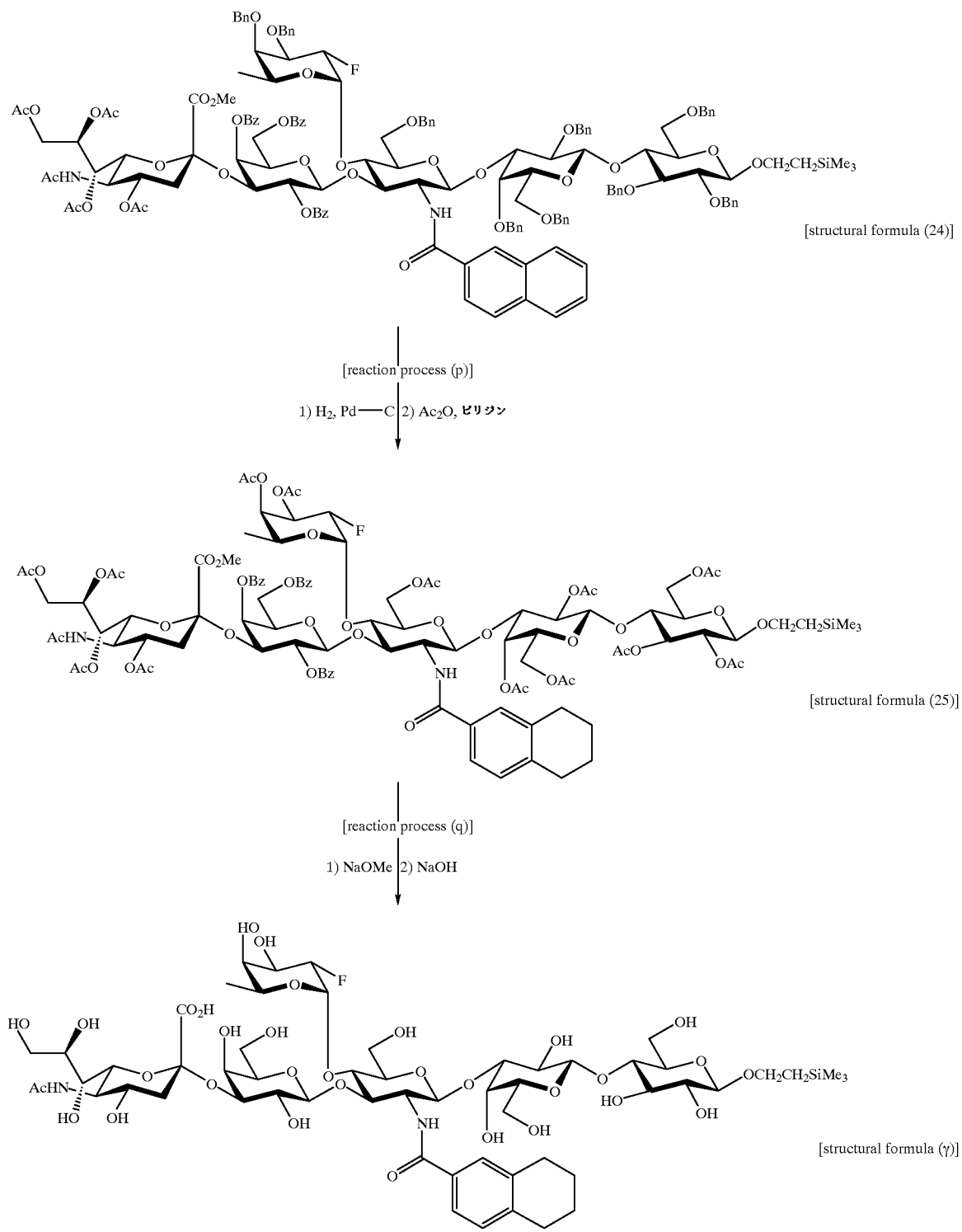

Although the naphthalene ring is reduced in the above reaction, it is possible to obtain the compound in which the naphthalene moiety is not partially reduced by appropriately modifying the substituents $R^1$ and $R^4$ in general formula (1) and also the substituents represented by general formula (B). For this purpose, the said $R^1$, $R^4$ and $R^2$ in the case of general formula (B) may be modified to ethyl-2,4,6-tri-O-acetyl-β-D-galactoside-3-oxyl group, acetyl group, and Bn, respectively, similar to the above description. Next, the Reaction Schemes 5 and 6 are illustrated in detail. In this reaction process (1), acetyl groups of 2-(trimethylsilyl) ethyl O-(3,4,6-tri-O-acetyl-2-deoxy-2-phthalimide-β-D- glucopyranosyl)-(1→3)-O-(2,4,6-tri-O-benzyl-β-D-galactopyranosyl)-(1→4)-2,3,6-tri-O-benzyl-β-D-glucopyranoside [structural formula (20)] as a starting material are removed using an alkaline metal alkoxide or alkalineearthmetal alkoxide (e.g. sodium methoxide, sodium ethoxide, sodium t-butoxide, lithium methoxide, magnesium methoxide, calcium methoxide, and the like), or an alkaline metal hydroxide or alkalineearthmetal hydroxide (e.g. sodium hydroxide, lithium hydroxide, potassium hydroxide, magnesium hydroxide, calcium hydroxide, and the like) in a protic solvent (e.g. water, methanol, ethanol, n-propanol, isopropanol, n-butanol, t-butanol or a mixture of these solvents, etc.) at 0° C.–40° C. for 2–48 hr.

Thereafter, after removing the phthalimide of the glucosamine moiety by treatment in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents) in the presence of a deprotective agent for the phthalimide (e.g. hydrazine, ethylene diamine or their mixture) at 30° C.–100° C. for 6–24 hr, without or after purification, by reacting 2-naphthoyl chloride with the above product in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents) at 5° C.–50° C. for 2–24 hr, the above product can be converted to the resulting 2-naphthoylated form represented by structural formula (21). Further, in the reaction process (m), by introducing a in benzylidene group into the hydroxyl groups at the 4- and 6-positions of the compound represented by the said structural formula (21), in the presence of benzaldehyde dimethylacetal/p-toluenesulfonic acid, benzaldehyde-anhydrous zinc chloride, benzaldehyde-conc. sulfuric acid, or the like, the compound represented by structural formula (22) can be obtained. Next, in the reaction process (n), after the compound represented by structural formula (22) is obtained by introducing the said benzylidene group, by cleaving the said benzylidene group using a reductive cleaving reagent (e.g. sodium cyanoborohydride-hydrogen chloride, borane trimethylamine complex-aluminum chloride, borane dimethylamine complex-boron trifluoride ether complex and the like) in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents), the compound represented by structural formula (23) can be obtained.

Next, in the reaction process (o), because all hydroxyl groups of the glucosamine moiety in the compound represented by structural formula (23) are protected with benzyl groups and the like except the two hydroxyl groups at the 3- and 4-positions, introducing sialylgalactose [structural formula (13)] and in turn methyl 3,4-di-O-benzyl-2-deoxy-2-fluoro-1-thio-L-fucopyranoside becomes possible. The sialyl Lewis a hexose represented by structural formula (24) (which corresponds to general formula (1) of the present invention) can be obtained by treatment in a reaction-inert solvent (e.g. benzene, toluene, methylene chloride, dichloroethane, diethyl ether, tetrahydrofuran, or a mixture of these solvents, etc.) at 5° C.–35° C. for 12–24 hr in the presence of an appropriate glycosylation promotor (e.g. N-iodosuccinimide/scandium trifluoromethanesulfonate, N-iodosuccinimide/tetrabutylammonium triflate, dimethyl (methylthio)sulfonium triflate (DMTST), N-iodosuccinimide/trifluoromethanesulfonic acid, silver trifluoromethanesulfonate/methylsulfenyl bromide and the like) and synthetic zeolite (molecular sieves), etc.

Next, in the reaction process (p), by removing the benzyl group of the obtained sialyl Lewis a glycoside by reaction in a reaction-inert solvent (e.g. methanol, ethanol, n-propanol, isopropanol, ethyl acetate, methyl acetate, acetic acid or a mixture of these solvents, etc.) in the presence of the catalysts for catalytic reduction (e.g. palladium—carbon, palladium hydroxide—carbon, palladium—barium sulfate) using a hydrogen donor (e.g. hydrogen gas, cyclohexene, cyclohexadiene, formic acid, ammonium formate salts, etc.) at 0° C.–50° C. for 10–120 hr, and by acetylating the generated free hydroxyl group in a basic organic solvent (e.g. pyridine, triethylamine, γ-lutidine, piperidine, N-methylmorpholine or a mixture of these solvents, etc.) using an acetylating agent (e.g. acetic anhydride, acetyl chloride, and the like) at 0° C.–60° C. for 2–40 hr, the compound represented by structural formula (25) can be obtained. Finally, in the reaction process (q), by reacting benzoyl (Bz) and acetyl groups (Ac) as protective groups of the hydroxyl groups with an alkaline metal alkoxide or alkalineearthmetal alkoxide (e.g. sodiummethoxide, sodium ethoxide, sodium t-butoxide, lithium methoxide, magnesium methoxide, calcium methoxide, and the like), or an alkaline metal hydroxide and alkalineearthmetal hydroxide (e.g. sodium hydroxide, lithium hydroxide, potassium hydroxide, magnesium hydroxide, calcium hydroxide, and the like) in a protic solvent (e.g. water, methanol, ethanol, n-propanol, isopropanol, n-butanol, t-butanol or a mixture of these solvents, etc.) at 0° C.–40° C. for 2–48 hr, the compound represented by structural formula (γ) as 2-fluorofucosyl-α-(1→4)-N-tetrahydronaphthylglucosamine derivative of the present invention can be obtained.

Next, the preparation method for 2-fluorofucosyl-α-(1→4)-N-4-t-butylbenzoyl-glucosamine derivative represented by the said structural formula (δ) is illustrated referring to the following Reaction Schemes 7 and 8. In this reaction process, 2-(trimethylsikyl)ethyl O-(3,4,6 -tri-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-o-benzyl-β-D-glucopyranoside [structural formula (20)] can be used as a starting material. First, as shown in the Reaction Scheme 7, after deacetylation and dephthalimidation of this compound [structural formula (20)], this Scheme comprises 4-t-butylbenzoylation of this compound [structural formula (26), reaction process (r)] followed by introduction of a benzylidene group [structural formula (27), reaction process (s)]. Next, by performing reductive cleavage of the benzylidene group [structural formula (28), reaction process (t)], then introducing the sialylgalactose moiety represented by structural formula (13) using, for example, silver trifluoromethanesulfonate/methylsulfenyl bromide as a reaction accelerator, and by reacting with methyl 3,4-di-O-benzyl-2-deoxy-2-fluoro-1-thio-L-fucopyranoside [reaction process (u)] using, for example, N-iodosuccinimide/trifluoromethanesulfonic acid, the sialyl Lewis a hexose [corresponding to the derivative represented by general formula (1) of the present invention] represented by structural formula (29) can be obtained.

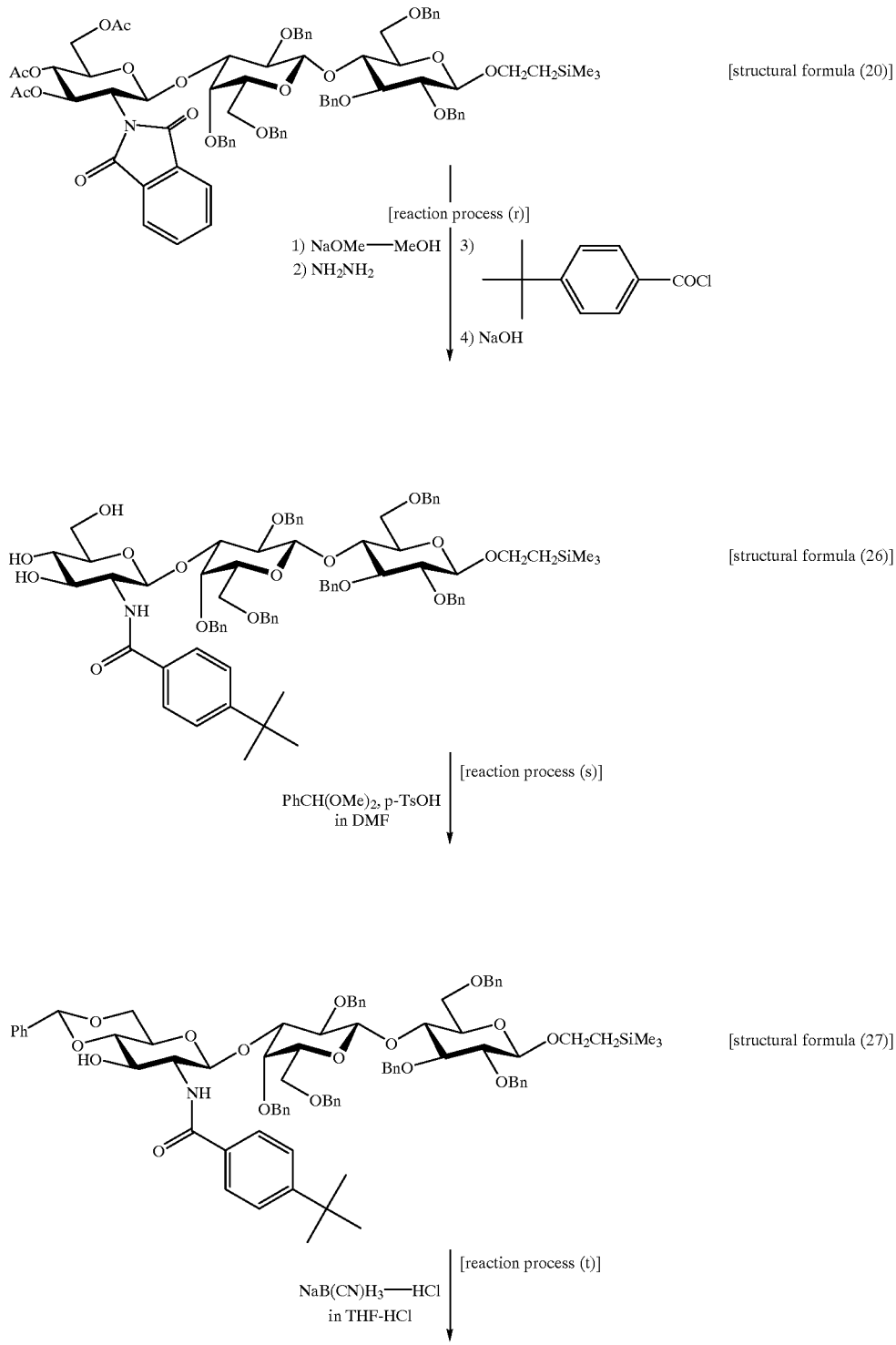

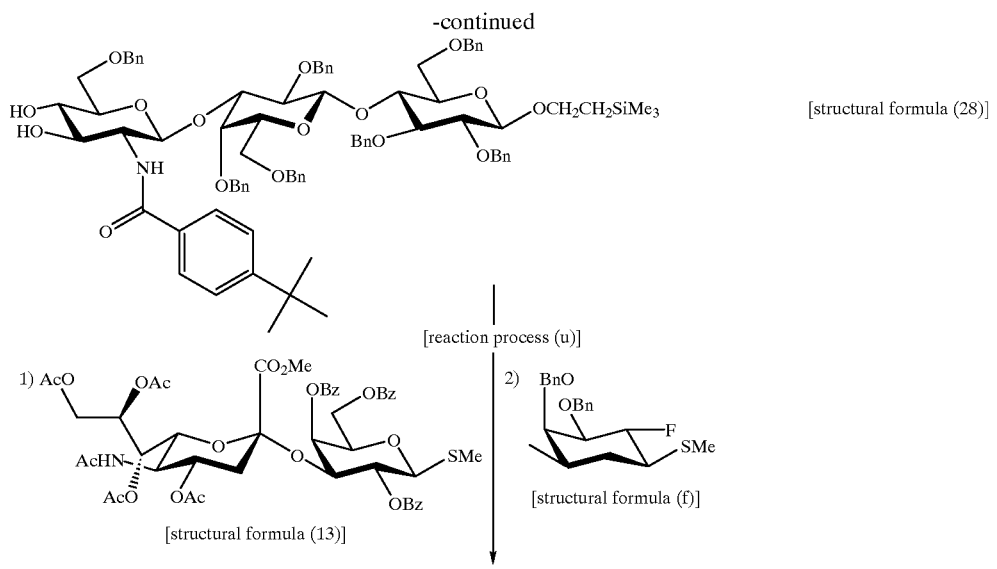

[structural formula (28)]

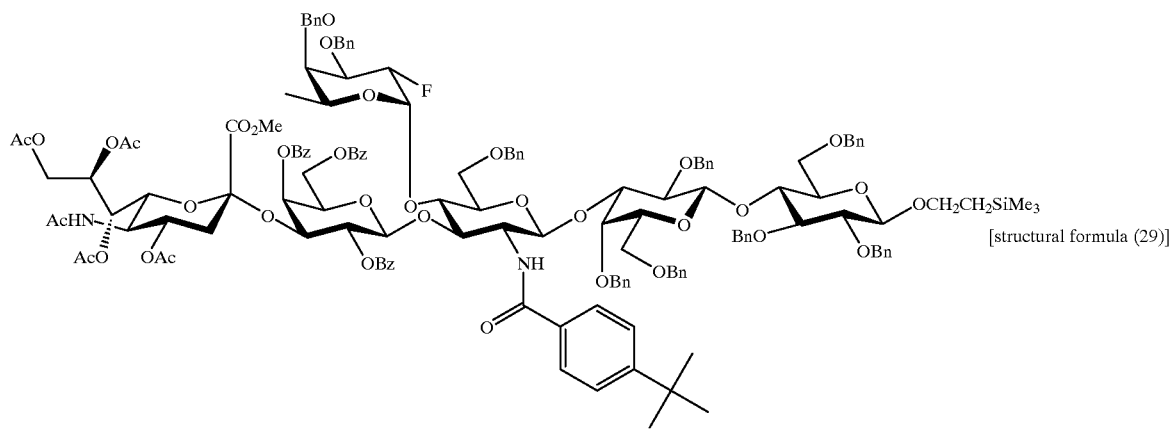

[structural formula (29)]

In addition, as shown in the following Reaction Scheme 8, catalytic reduction [reaction process (v)] of the compound represented by structural formula (29) followed by acetylation can lead to the derivative represented by structural formula (30) where its naphthalene moiety is partially reduced. Finally, the derivative represented by structural formula (δ) which is the objective compound of the present invention can be obtained by treating with sodium methoxide, sodium hydroxide and the like [reaction process (w)].

Reaction Scheme 8

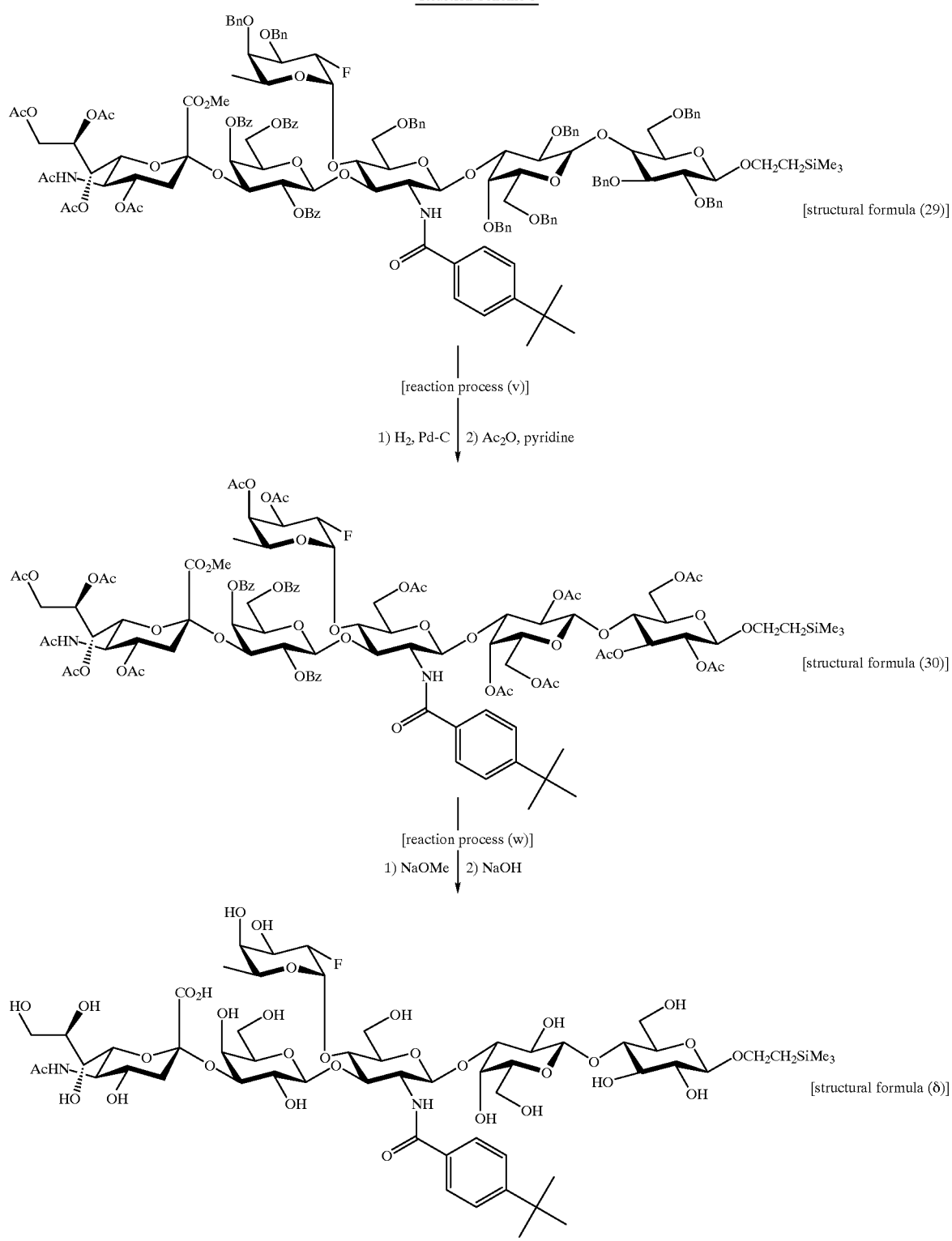

Next, Reaction Schemes 7 and 8 are further specifically illustrated. In the reaction process (r), 2-(trimethylsikyl) ethyl O-(3,4,6 -tri-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-glucopyranoside [structural formula (20)] as a starting material is deacetylated by the use of an alkaline metal alkoxide or a alkalineearthmetal alkoxide (e.g. sodium methoxide, sodium ethoxide, sodium t-butoxide, lithium methoxide, magnesium methoxide, calcium methoxide, and the like), or a alkaline metal hydroxide or alkalineearthmetal hydroxide (e.g. sodium hydroxide, lithium hydroxide, potassiumhydroxide, magnesiumhydroxide, calciumhydroxide, and the like) in a protic solvent (e.g. water, methanol, ethanol, n-propanol, isopropanol, n-butanol, t-butanol or a mixture of these solvents, etc.) at 0° C.–40° C. for 2–48 hr. Thereafter, the phthalimide of the glucosamine moiety is removed by treatment in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents) in the presence of a deprotective agent of phthalimide (e.g. hydrazine, ethylene diamine or a mixture of these) at 30° C.–100° C. for 6–24 hr. Then, without or after purification, 4-t-butylbenzoylchloride is reacted with the above product in a reaction-inert solvent (e.g. benzene, toluene, methylene chloride, dichloroethane, diethyl ether, tetrahydrofuran, dimethyl sulfoxide, dimethyl formamide, methanol, ethanol, n-propanol, isopropanol, n-butanol, isobutanol or a mixture of these solvents) at 5° C.–50° C. for 2–24 hr, and it can be converted to the resulting 4-t-butylbenzoylated form represented by structural formula (26). Further, in the reaction scheme (s), introduction of a benzylidene group into the hydroxyl groups at the 4- and 6-positions of the compound represented by the said structural formula (26), for example, in the presence of benzaldehyde dimethylacetal-p-toluenesulfonic acid, benzaldehyde-anhydrous zinc chloride or benzaldehyde-conc. sulfuric acid can lead to the compound represented by structural formula (27). Next, in the reaction process (t), after obtaining the compound represented by structural formula (27) by introducing the said benzylidene group, cleaving the said benzylidene moiety using a reductive cleaving reagent (e.g. sodium cyanoborohydride-hydrogen chloride, borane. dimethylamine complex-aluminum chloride, borane dimethylamine complex-boron trifluoride ether complex and the like) in a reaction-inert solvent (e.g. benzene, toluene, methylene chloride, dichloroethane, diethyl ether, tetrahydrofuran, dimethylsulfoxide, dimethylformamide, methanol, ethanol, n-propanol, isopropanol, n-butanol, isobutanol or a mixture of these solvents and the like) can lead to the compound represented by structural formula (28). Next, in the reaction process (u), because all hydroxyl groups of the glucosamine moiety in the compound represented by structural formula (28) are protected with benzyl groups and the like except the two hydroxyl groups at the 3- and 4-positions of the glucosamine moiety, in turn introducing sialylgalactose [structural formula (13)] and methyl 3,4-di-O-benzyl-2-deoxy-2-fluoro-1-thio-L-fucopyranoside represented by the said structural formula (f) becomes possible. In this reaction, the sialyl Lewis a hexose represented by structural formula (29) (which corresponds to general formula (1) of the present invention) can be obtained by treatment in a reaction-inert solvent (e.g. benzene, toluene, methylene chloride, dichloroethane, diethyl ether, tetrahydrofuran, or a mixture of these solvents, etc.) at 5° C.–35° C. for 12–24 hr in the presence of an appropriate glycosylation accelerator (e.g. N-iodosuccinimide/scandium trifluoromethanesulfonate, N-iodosuccinimide/tetrabutylammonium triflate, dimethyl (methylthio)sulfonium triflate (DMTST), N-iodosuccinimide/trifluoromethanesulfonic acid, silver trifluoromethanesulfonate/methylsulfenyl bromide and the like) and synthetic zeolite (molecular sieves), etc. Next, in the reaction process (v), the benzyl group of the sialyl Lewis a glycoside obtained as above, is removed by reaction in a reaction-inert solvent (e.g. methanol, ethanol, n-propanol, isopropanol, ethyl acetate, methyl acetate, acetic acid or a mixture of these solvents and the like) in the presence of a catalyst for catalytic reduction (e.g. palladium—carbon, palladium hydroxide—carbon, palladium—barium sulfate) using a hydrogen donor (e.g. hydrogen gas, cyclohexene, cyclohexadiene, formic acid, ammonium formate salts, etc.) at 0° C.–50° C. for 10–120 hr, then the liberated free hydroxyl group is acetylated in a basic organic solvent (e.g. pyridine, triethylamine, γ-lutidine, piperidine, N-methylmorpholine or a mixture of these solvents, etc.) using an acetylating agent (e.g. acetic anhydride, acetyl chloride, and the like) at 0° C.–60° C. for 2–40 hr, which can lead to the compound represented by structural formula (30). Finally, in the reaction process (w), reaction of benzoyl (Bz) and acetyl groups (Ac) as the protective groups of the hydroxyl groups with an alkaline metal alkoxide or alkalineearthmetal alkoxide (e.g. sodium methoxide, sodium ethoxide, sodium t-butoxide, lithium methoxide, magnesium methoxide, calcium methoxide, and the like), or an alkaline metal hydroxide or alkalineearthmetal hydroxide (e.g. sodium hydroxide, lithium hydroxide, potassium hydroxide, magnesium hydroxide, calcium hydroxide, and the like) in a protic solvent (e.g. water, methanol, ethanol, n-propanol, isopropanol, n-butanol, t-butanol or a mixture of these solvents, etc.) at 0° C.–40° C. for 2–48 hr can lead to the compound represented by structural formula (δ) as 2-fluorofucosyl-α-(1→4)-N-4-t-butylbenzoylglucosamine derivative according to the present invention.

INDUSTRIAL APPLICATION

The derivatives of the present invention are 2-fluorofucosyl-N-aroylglucosamine derivatives in which the hydroxyl group at the 3- or 4-position of N-aroylglucosamine is substituted with 2-fluorofucose. They are especially excellent in metabolic stability against decomposition enzymes such as fucosidase because they have the 2-fluorofucose moiety. Further, as the N-aroylglucosamine moiety has the aroyl group, their selectin-adhesive-inhibition activity is superior. For example, they can provide derivatives that are excellent in metabolic stability as well as highly selective inhibition of the adhesive process of leukocytes to selecting.

Therefore, they can suppress neutrophil (a kind of leukocyte)-dependent and selectin-dependent acute inflammation and the like, and are useful as medicinal components for the purpose of the treatment, improvement and prevention of myocardial ischemic reperfusion disorder during redisobliteration therapy such as percutaneous transluminal coronary angioplasty (PTCA), acute respiratory distress syndrome (ARDS), inflammation, or thrombus formation accompanied with inflammnation, multiple sclerosis, bronchial asthma, rheumatism, autoimmune disease, chronic diseases such as allergic disease, diabetes, ophthalmopathy, psoriasis, and cancer. Further, it is possible to prepare the present inventive derivatives with good reproductivity and in high yields according to the method for preparation of the present inventive derivatives. Furthermore, the present inventive intermediates of the derivatives are useful synthetic intermediates of the derivatives and their preparation methods, and it is possible to obtain the intermediates of the present inventive derivatives with good reproductivity and in high yields according to the preparation method of the present inventive intermediates.

EXAMPLES

Figure 1:
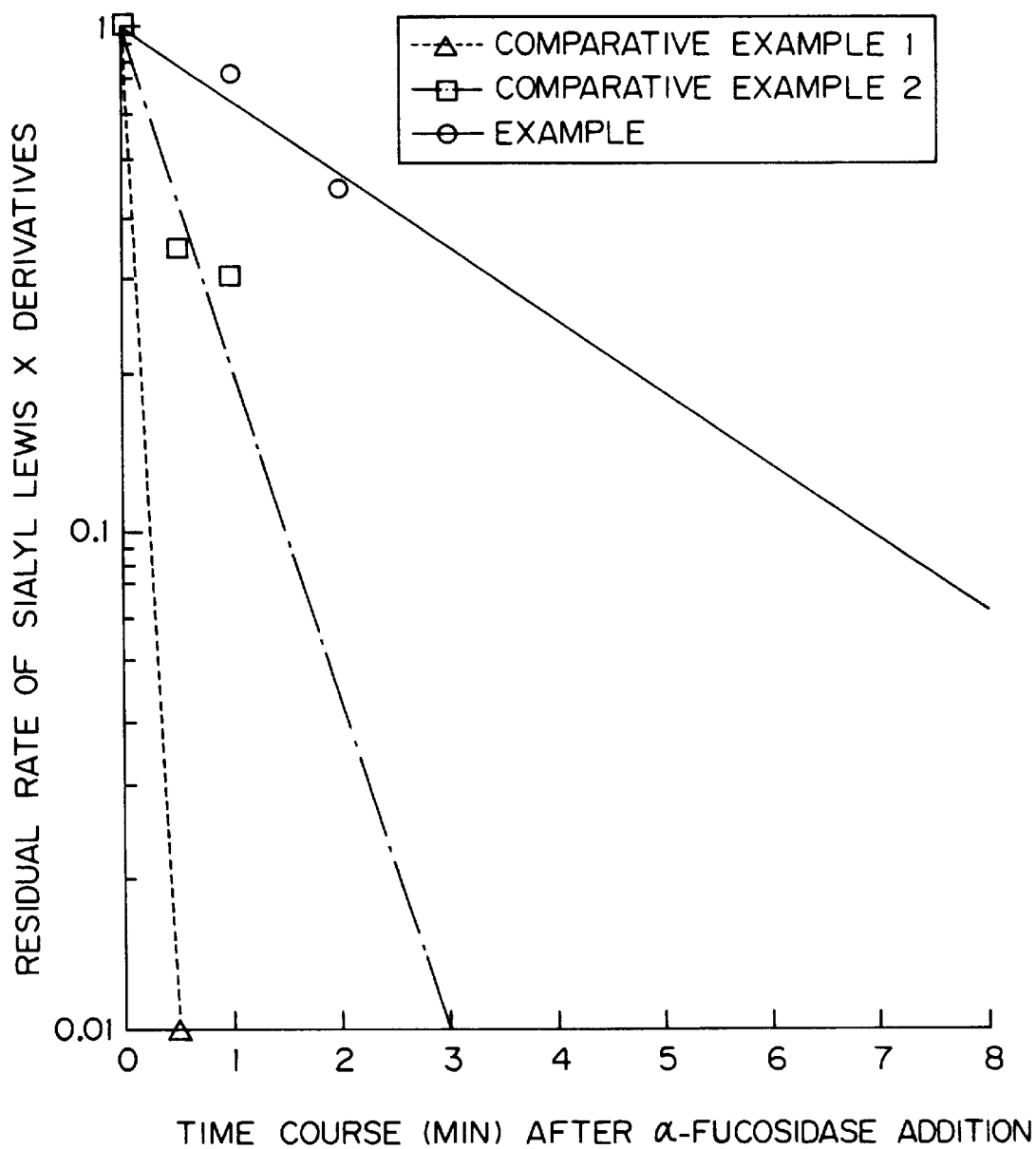
FIG. 1 is a graph showing the remnant ratio of the sialyl Lewis X derivatives at each time course after the addition of α-fucosidase.

The following examples are given to further illustrate the present invention. However, it should be understood that the present invention is not limited by the following examples.

Reference Example

Object: synthesis of 2-(trimethylsilyl)ethyl O-(4,6-O-benzylidene-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-glucopyranoside [said structural formula (e): hereinafter, abbreviated to compound (e)].

0.515 g (0.368 mmol) of 2-(trimethylsilyl)ethyl O-(3,4,6-tri-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-glucopyranoside was dissolved in 2.2 mL of anhydrous methanol, and 16 mg (0.296 m mol)of sodium methoxide was added under an argon atmosphere, and the mixture was stirred at room temperature for 2 hr. The reaction solution obtained was directly neutralized through a column of Amberlite IR120B (H$^+$) (eluent:methanol). Subsequently, the residual which was obtained by concentration of the combined eluates under reduced pressure was dissolved in 4.7 mL of anhydrous dimethyl formamide, then, 0.35 mL (2.33 mmol) of benzaldehyde dimethylacetal and 9 mg (0.047 mmol) of p-toluenesulfonic acid monohydrate were added, and the mixture was stirred at room temperature for 16 hr. The reaction solution obtained was passed through a layer of Amberlite IRA-410 (OH$^-$) (eluent:methanol). Further, after concentrating the combined eluants under reduced pressure, the residual was purified through silica gel flash chromatography (eluent; hexane:ethyl acetate=2:1) to give 259 mg (53% yield) of 2-(trimethylsikyl)ethyl O-(4,6-O-benzylidene-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-glucopyranoside [above compound (e)].

The analytical results of this compound are as follows:

$C_{80}H_{87}NO_{17}Si$ (mol. wt. 1362.7)

IR$^{KBr}_{max}$ cm$^{-1}$: 3475 (OH), 1715 (imide), 1090 (ether), 860, 840 (Me$_3$Si), 735, and 700 (Ph)

$^1$H-NMR (CDCl$_3$; TMS):δ7.6–6.8 (m, 39H, Phthal+7Ph), 5.59 (s, 1H, PhCH), and 0.98 (m, 2H, CH$_2$SiMe$_3$)

MS: m/z Found 1362.5821 (M+H); Calcd. 1362.5850 for $C_{80}H_{87}NO_{17}Si$

Example 1

Object: synthesis of 2-(trimethylsilyl)ethyl-O-(3,4-di-O-benzyl-2-deoxy-2-fluoro-α-L-fucopyranosyl)-(1→3)-O-(4,6-O-benzylidene-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-glucopyranoside [said structural formula (10): hereinafter, abbreviated to compound (10)] 3.5 mg (0.075 mmol) of methyl 3,4-di-O-benzyl-2-deoxy-2-fluoro-1-thio-β-L-fucopyranose represented by said structural formula (f) and 75 mg (0.055 mmol) of compound (e) obtained in the said Reference Example were dissolved in 2.3 mL of anhydrous benzene and 0.4 g of activated molecular sieves (pore size 4 Å) was added under an argon atmosphere. After stirring at room temperature for 16 hr and cooling up to about 7° C., 120 mg (0.465 mmol) of dimethyl(methylthio)sulfonium triflate (DMTST) was added and stirred at the same temperature for 2 hr. After cooling the reaction mixture down to 4° C., 1.2 mL of methanol and then 0.4 mL of triethylamine were added, and stirred at the same temperature for 30 min. Then the insoluble portion was separated by suction filtration and washed with dichloromethane. After washing the combined filtrate and the washings with water, the solution was dried with sodium sulfate and concentrated under reduced pressure. The residual was submitted to flash chromatography (eluent; n-hexane:ethyl acetate=4:1) to give 75 mg (80.6% yield) of the said compound (10).

The analytical results of this compound are as follows:

$C_{100}H_{108}NO_{20}FSi$ (mol. wt. 1691.1)

$[α]_D^{23}$=−41.6° (c 1.025, chloroform)

IR$^{KBr}_{max}$ cm$^{-1}$: 3470 (NH), 1715 (imide), 1100 (ether), 860, 835 (Me$_3$Si), 735, and 700 (Ph)

$^1$H-NMR (CDCl$_3$; TMS):δ7.8–6.8 (m, 49H, Phthal+9Ph), 5.57 (s, 1H, PhCH), 4.89 (d, 1H, J$_{1,2}$=4.1 Hz, H-1, fucose moiety), 0.98 (m, 2H, CH$_2$SiMe$_3$), and 0.79 (d, 3H, J$_{5,6}$=6.5 Hz, H-6, fucose moiety)

$^{19}$F-NMR (CDCl$_3$; CFCl$_3$):δ−207 (ddd, J$_{F, 3H}$=9.4 Hz, J$_{F, 1H}$=3.3 Hz, 2-F)

MS: m/z Found 1690.7296 (M+H); Calcd. 1690.7308 for

Example 2

Object: synthesis of 2-(trimethylsilyl)ethyl O-(3,4-di-O-benzyl-2-deoxy-2-fluoro-α-L-fucopyranosyl)-(1→3)-O-(4,6-O-benzylidene-2-deoxy-2-naphthamide-β-D-glucopyranosyl)-(1→3)-O-(2,4,6-tri-O-benzyl-β-D-galactopyranosyl)-(1→4)-2,3,6-tri-O-benzyl-β-glucopyranoside [said structural formula (11): heareinafter, abbreviated to compound (11)]

285 mg (0.169 mmol) of the compound (10) obtained in Example 1 was dissolved in 26 mL of n-butanol under an argon atmosphere followed by adding 8.8 mL of ethylene diamine, and stirred at 82° C. for 20 hr. After concentrating under a reduced pressure at below 60° C., 48 mL of pyridine, 750 mg (3.93 mmol) of 2-naphthoyl chloride and a further 25 mg (0.205 mmol) of N,N-dimethylaminopyridine were added to the residual, and the mixture was stirred at room temperature for 12 hr under an argon atmosphere. Then the reaction mixture was cooled down to 0° C. followed by adding 9 mL of methanol, and stirred at the same temperature for 2 hr. After concentrating under a reduced pressure again, the residual was purified by flash chromatography (eluent; n-hexane:ethyl acetate=5:2) to give 236 mg (81.7% yield) of the said compound (11).

The analytical results of this compound are as follows.

$C_{103}H_{112}NO_{19}FSi$ (mol. wt. 1715.1)

$[α]_D^{23}$=−41.2° (c 1.04, chloroform)

IR$^{KBr}_{max}$ cm$^{-1}$: 3415 (NH), 1685, 1520 (amide), 1095 (ether), 860, 835 (Me$_3$Si), 735, and 695 (Ph)

$^1$H-NMR (CDCl$_3$; TMS): δ8.0–6.8 (m, 52H, 2-Naphth+9Ph), 5.49 (s, 1H, PhCH), 5.05 (d, 1H, J$_{1,2}$=3.8 Hz, H-1, fucosemoiety), 0.90 (m, 2H, CH$_2$SiMe$_3$), and 0.73 (d, J$_{5,6}$=6.4 Hz, H-6, fucose moiety)

$^{19}$F-NMR (CDCl$_3$; CFCl$_3$):δ−207 (br ddd, J$_{F, 2H}$=50 Hz, J$_{F, 3H}$=8.9 Hz, 2-F)

MS: m/z Found 1714.7660 (M+H); Calcd. 1714.7686 for $C_{103}H_{112}NO_{19}FSi$

Example 3

Object: synthesis of 2-(trimethylsilyl)ethyl O-(3,4 -di-O-benzyl-2-deoxy-2-fluoro-α-L-fucopyranosyl)-(1→3)-O-(6-O-benzyl-2-deoxy-2-naphthamide-β-D-glucopyranosyl)-

(1→3)-O-(2,4,6-tri-O-benzyl-β-D-galactopyranosyl)-(1→4)-2,3,6-tri-O-benzyl-β-glucopyranoside [said structural formula(12): hereinafter, abbreviated to compound (12)]. 46 mg (0.0268 mmol) of compound (11) obtained in Example 2 was dissolved in 1.2 mL of anhydrous tetrahydrofuran, and 180 mg of activated molecular sieves (pore size 4 Å) was added under an argon atmosphere. After the mixture was stirred at room temperature for 1 hr, 140 mg (2.22 mmol) of sodium cyanoborohydride was added at the same temperature followed by cooling down to 0° C., and 2.8 mL (2.8 mmol) of 1 M-hydrogenchloride-ether solution was dropped under an argon atmosphere. After raising the reaction temperature up to room temperature, stirring for 15 min, adding 5 mL of dichloromethane and 1 mL of water, the insoluble portion was separated by filtration, and then washed with dichloromethane. The combined filtrate and washings were washed with 2 M-aqueous hydrochloric acid, 5% aqueous sodium bicarbonate and satd. brine, and dried with sodium sulfate. After concentrating under a reduced pressure, the residual was submitted to flash chromatography (eluent; n-hexane:ethyl acetate=2:1) to give 23 mg (50.0% yield) of said compound (12).

The analytical results of this compound are as follows:

$C_{103}H_{114}NO_{19}FSi$ (mol. wt. 1717.1)

$[\alpha]_D^{23}$=−19.0° (c 0.51, chloroform)

$IR^{KBr}_{max}$ cm$^{-1}$: 3700–3200 (OH, NH), 1670, 1495 (amide), 1070 (ether), 860, 840 (Me$_3$Si), 735, and 695 (Ph)

$^1$H-NMR (CDCl$_3$; TMS): δ8.1–6.8 (m, 52H, 2-Naphth+9Ph), 5.81 (d, 1H, J=8.9 Hz, OH), 1.16 (d, 3H, $J_{5,6}$=6.5 Hz, H-6, fucose moiety), and 0.97 (m, 2H, CH$_2$SiMe$_3$)

$^{19}$F-NMR (CDCl$_3$; CFCl$_3$):δ207 (ddd, $J_{F,\,2H}$=51 Hz, $J_{F,\,3H}$=8.9 Hz, $J_{F,\,1H}$=2.8 Hz, 2-F)

MS: m/z Found 1716.7817 (M+H); Calcd. 1716.7661 for $C_{103}H_{114}NO_{19}FSi$

Example 4

Object: synthesis of 2-(trimethylsilyl)ethyl O-(methyl-5-acetamide-4,7,8,9-tetra-O-acetyl-3,5-dideoxy-D-glycero-α-D-galacto-2-nunolopyranosylonate)-(2→3)-O-(2,4,6 -tri-O-benzoyl-O-D-galactopyranosyl-(1→4)-O-[(3,4-di-O-benzyl-2-deoxy-2-fluoro-α-L-fucopyranosyl)-(1→3)]-O-(6-O-benzyl-2-deoxy-2-naphthamide-β-D-glucopyranosyl)-(1→3)-O-(2,4,6-tri-O-benzyl-β-D-galactopyranosyl)-(1→4)-2,3,6-tri-O-benzyl-β-glucopyranoside [said structural formula (14): hereinafter abbreviated to compound (14)]

82.3 mg (0.048 mmol) of compound (12) obtained in Example 3 and O-(methyl-5-acetamide-4,7,8,9-tetra-O-acetyl-3,5-dideoxy-D-glycero-α-D-galacto-2-nunolopyranosylonate)-(2→3)-O-(2,4,6-tri-O-benzoyl-1-thio-β-D-galactopyranoside [said structural formula (13)=said structural formula (g)] were dissolved in 3.6 mL of anhydrous dichloromethane and 500 mg of activated molecular sieves (pore size 4 Å) was added under an argon atmosphere. After stirring at room temperature for 2.5 hr, 72 mg (0.28 mmol) of dimethyl(methylthio)sulfonium triflate (DMTST) was added and stirred at the same temperature for 20 hr under an argon atmosphere. The reaction mixture was cooled in ice, then 0.4 mL of methanol and 0.2 mL of trimethylamine were added, and stirred at the same temperature for 30 min. After diluting with dichloromethane, filtration and washing, the combined filtrate and the washings were washed with water. Further, the solution was dried with sodium sulfate and concentrated under a reduced pressure. The residual obtained was submitted to flash chromatography (eluent; n-hexane:ethyl acetate=1:3) to give 72.7 mg (56.9% yield) of said compound (14).

The analytical results of this compound are as follows:

$C_{150}H_{163}N_2O_{39}FSi$ (mol. wt. 2665.0) $[\alpha]_D^{23}$=−12.9° (c 0.52, chloroform)

$IR^{KBr}_{max}$ cm$^{-1}$: 3400 (NH), 1740, 1260 (ester), 1690, 1500 (amide), 1070 (ether), 860, 805 (Me$_3$Si), 735, and 715 (Ph)

$^1$H-NMR (CDCl$_3$; TMS): δ8.3–7.0 (m, 67H, 2-Naphth+12Ph), 5.6 7 (m, 1H, H-8, sialic acid moiety), 5.56 (dd, 1H, $J_{1,2}$=8.3 Hz, $J_{2,3}$=9.6 Hz, H-2, galactose moiety), 5. 35 (br. d, 1H, $J_{3,4}$=$J_{4,5}$=3.5 Hz, H-2, galactose moiety), 5.28 (dd, 1H, $J_{7,8}$=9.6 Hz, $J_{6,7}$=2.6 Hz, H-7, sialic acid moiety), 3.81 (s, 3H, OCH$_3$), 2.51 (dd, 1H, $J_{3e,3a}$=12.5 Hz, $J_{3e,4}$=4.5 Hz, H-3e, sialic acid moiety), 2.18, 2.00, 1.97, 1.84 (4s, 12H, 4AcO), 1.56 (s, 3H, AcN), 1.11 (d, 3H, $J_{5,6}$=6.4 Hz, H-6, sialic acid moiety), and 1.01 (m, 2H, Me$_3$SiCH$_2$ CH$_2$O)

$^{19}$F-NMR (CDCl$_3$; CFCl$_3$): δ−208 (br ddd, $J_{F,\,2H}$=49 Hz, $J_{F,\,3H}$=7.50 Hz, 2-F).

MS: m/z Found 2665.0698 (M+H); Calcd. 2665.0736 for $C_{150}H_{163}N_2O_{39}FSi$ Example 5

Object: synthesis of 2-(trimethylsilyl)ethyl O-(methyl-5-acetamide-4,7,8,9-tetra-O-acetyl-3,5-dideoxy-D-glycero-α-D-galacto-2-nunolopyranosylonate)-(2→3)-O-(2,4,6-tri-O-benzoyl-β-D-galactopyranosyl)-(1→4)-O-[(3,4-di-O-acetyl-2-deoxy-2-fluoro-α-L-fucopyranosyl-(1→3)3)]-O-[6-O-acetyl-2-deoxy-2-(5,6,7,8-tetrahydronaphthamide-β-D-glucopyranosyl)-(1→3)-O-(2,4,6-tri-O-acetyl-β-D-galactopyranosyl)-(1→4)-2,3,6-tri-O-acetyl-β-D-glucopyranoside [said structural formula (15): hereinafter, abbreviated to compound (15)]. 25 mg (0.0093 mmol) of the compound (14) obtained in Example 4 was dissolved in 4.2 mL of ethanol and 1.3 mL of acetic acid, and the mixture was hydrogenated in hydrogen at atmospheric pressure in the presence of 28 mg 10% palladium—carbon warming at 45° C. for 4 days. After filtrating this, the solvent was concentrated under a reduced pressure, 4 mL of pyridine and 2 mL of acetic anhydride were added to the residual obtained, and stirred at room temperature for 20 hr. After the solution was concentrated under a reduced pressure, the residual obtained was submitted to flash chromatography (eluent; n-hexane:ethyl acetate=1:6) to give 12 mg (57.2% yield) of said compound (15).

The analytical results of this compound are as follows:

$C_{105}H_{131}N_2O_{48}FSi$ (mol. wt. 2236.2)

$[\alpha]_D^{23}$=−20.0° (c 0.43, chloroform)

$IR^{KBr}_{max}$ cm$^{-1}$: 3380 (NH), 1750,1230 (ester), 1700, 1540 (amide), 1070 (ether), 860, 840 (Me$_3$Si), and 720 (Ph)

$^1$H-NMR (CDCl$_3$; TMS): δ8.3–7.0 (m, 18H, 4HNaph+3Ph), 5.66 (m, 1H, H-8, sialic acid moiety), 4.46 (d, 1H, $J_{1,2}$=7.9 Hz, H-1, glucose moiety), 3.80 (s, 3H, OCH$_3$), 2.83(br s, 4H, tetrahydronaphthalene moiety), 2.41 (dd, 1H, $J_{3a,3e}$=12.6 Hz, $J_{3e,4}$=4.5 Hz, H-3e, sialic acid moiety), 2.14, 2.13, 2.09, 2.09, 2.08, 2.07, 2.05, 2.02, 2.01, 1.98, 1.91, 1.90 (13 s, 39H, 13AcO), 1.56 (s, 3H, AcN), 1.08 (d, 3H, $J_{5,6}$=6.5 Hz, H-6, fucose moiety), and 0.89 (m, 2H, Me$_3$SiCH$_2$)

$^{19}$F-NMR (CDCl$_3$; CFCl$_3$):δ−208 (br dd, $J_{F,\,2H}$=50 Hz, $J_{F,\,3H}$=9.9 Hz, 2-F)

MS: m/z Found 2236.7736 (M+H); Calcd. 2236.7709 for $C_{105}H_{131}N_2O_{48}FSi$

Example 6

Object: synthesis of 2-(trimethylsilyl)ethyl O-(5-acetamide-3,5-dideoxy-D-glycero-α-D-galacto-2-nunolopyranosylonic acid)-(2→3)-O-β-D-galactopyranosyl-(1→4)-O-[(2-deoxy-2-fluoro-α-L-fucopyranosyl)-(1→3)]-O-[(2-deoxy-2-(5,6,7,8-tetrahydronaphthamide-β-D-glucopyranosyl)-(1→3)-(O-β-D-galactopyranosyl)-(1→4)-β-D-glucopyranoside [said structural formula (α): hereinafter, abbreviated to compound (α)]. 12 mg (0.0053 mmol) of the compound (15) obtained in Example 5 was dissolved in 1.0 mL of anhydrous methanol, then 10 mg (0.19 mmol) of sodium methoxide was added at room temperature under an argon atmosphere, and stirred at 40° C. for 21 hr. After cooling at room temperature, 0.8 mL of water was added to the reaction mixture and stirred for 8 hr. Then the solution was passed through an Amberlite IR120 (H$^+$) layer (eluent:methanol), and the residual concentrated under a reduced pressure was submitted to gel filtration column chromatography (eluent:methanol) using SephadexLH20 (15 g) to give 6.2 mg (85.0% yield) of compound (α).

The analytical results of this compound are as follows:

$C_{57}H_{91}N_2O_{32}FSi$ (mol. wt. 1363.4)

$[\alpha]_D^{23} = -30.0°$ (c 0.50, methanol)

IR$^{KBr}_{max}$ cm$^{-1}$: 3700–3200 (OH, NH), 2930, 2850 (methyl, methylene), 1740 (carboxylic acid), 1635, 1555 (amide), and 1070 (ether)

$^1$H-NMR (CD$_3$OD; TMS): δ7.6–7.0 (m, 3H, 4HNaph), 5.26 (d, 1H, H-8, $J_{1,2}$=3.8 Hz, H-1, fucose moiety), 2.88 (dd, 1H, $J_{3a,3e}$=12.7 Hz, $J_{3e,4}$=2.5 Hz, H-3e, sialic acid moiety), 2.80 (br s, 4H, tetrahydronaphthalene moiety), 2.02 (s, 3H, AcN), 1.17 (d, 3H, $J_{5,6}$=6.5 Hz, H-6, fucose moiety), and 1.00 (m, 2H, Me$_3$SiCH$_2$)

$^{19}$F-NMR (CD$_3$OD; CFCl$_3$):δ–163 (br dd, $J_{F,2H}$=50 Hz, $J_{F,3H}$=10.8 Hz, 2-F)

MS: m/z Found 1363.5837 (M+H); Calcd. 1363.5392 for $C_{57}H_{91}N_2O_{32}FSi$

Example 7

Object: synthesis of 2-(trimethylsilyl)ethyl O-(3,4-di-O-benzyl-2-deoxy-2-fluoro-α-L-fucopyranosyl)-(1→3)-O-[4,6-O-benzylidene-2-deoxy-2-(4-t-butylbenzamide-β-D-glucopyranosyl)]-(1→3)-O-(2,4,6-tri-O-benzyl-β-D-galactopyranosyl)-(1→4)-2,3,6-tri-O-benzyl-β-glucopyranoside [said structural formula (16): hereinafter, abbreviated to compound (16)].

291 mg (0.172 mmol) of the compound (10) obtained in Example 1 was dissolved in 24 mL of n-butanol under an argon atmosphere, then 6 mL of ethylenediamine was added, stirred and heated at 8° C. for 20 hr. Then 48 mL of pyridine, 0.8 mL (4.19 mmol) of 4-t-butylbenzoylchloride and 30 mg (0.246 mmol) of N,N-dimethylaminopyridine were added to the residual obtained after concentrating below 60° C. under a reduced pressure, and then stirred at room temperature under an argon atmosphere for 16 hr. After cooling down to 0° C., 9 mL of methanol was added and stirred at room temperature for 3 hr. After concentration under a reduced pressure again, the residue obtained was purified by flash chromatography (eluent; n-hexane:ethyl acetate=3:1) to give 280 mg (94.6% yield) of compound (16).

The analytical results of this compound are as follows:

$C_{103}H_{118}NO_{19}FSi$ (mol. wt. 1715.1) $[\alpha]_D^{23}$=–39.1° (c 0.97, chloroform)

$^1$H-NMR (CDCl$_3$; TMS): δ7.6–6.8 (m, 49H, t-BuBz+ 9Ph), 5.56 (s, 1H, PhCH), 5.07 (d, 1H, $J_{1,2}$=3.8 Hz, H-1, fucose moiety), 1.25 (s, 9H, t-Bu), 1.00 (m, 2H, CH$_2$SiMe$_3$), and 0.79 (d, $J_{5,6}$=6.4 Hz, H-6, fucose moiety)

$^{19}$F-NMR (CDCl$_3$; CFCl$_3$):δ–207 (ddd, $J_{F,2H}$=50 Hz, $J_{F,3H}$=9.4 Hz, $J_{F,1H}$=2.7 Hz, 2-F)

MS: m/z Found 1721.8163 (M+H); Calcd. 1721.8177 for $C_{103}H_{118}NO_{19}FSi$

Example 8

Object: synthesis of 2-(trimethylsilyl)ethyl O-(3,4-di-O-benzyl-2-deoxy-2-fluoro-α-L-fucopyranosyl)-(1→3)-O-[6-O-benzyl-2-deoxy-2-(4-t-butylbenzamide-β-D-glucopyranosyl)-(1→3)-O-(2,4,6-tri-O-benzyl-β-D-galactopyranosyl)-(1→4)-2,3,6-tri-O-benzyl-β-glucopyranoside [said structural formula (17): hereinafter, abbreviated to compound (17)]. 214 mg (0.124 mmol) of compound (16) obtained in Example 7 was dissolved in 10 mL of anhydrous tetrahydrofuran, and 900 mg of activated molecular sieves (pore size 4 Å) was added under an argon atmosphere. After the mixture was stirred at room temperature for 1 hr, 700 mg (11.1 mmol) of sodium cyanoborohydride was added at the same temperature, cooled down to 0° C., then 13 mL (13 mmol) of 1 M-hydrogenchloride-ether solution was dropped under an argon atmosphere. After raising the reaction temperature up to room temperature, this mixture was stirred for 20 min, followed by adding 20 mL of dichloromethane and 15 ml of water, then the insoluble portion was separated by filtration, and washed with dichloromethane. The combined filtrate and washings were washed with 2 M-aqueous hydrochloric acid, 5% aqueous sodium bicarbonate and satd. brine, and dried with sodium sulfate.

After concentrating under a reduced pressure, the residual was submitted to flash chromatography (eluent; n-hexane:ethyl acetate=2:1) to give 186 mg (86.8% yield) of said compound (17).

The analytical results of this compound are as follows:

$C_{103}H_{120}NO_{19}FSi$ (mol. wt. 1723.1)

$[\alpha]_D^{23}$=–14.2° (c 1.05, chloroform)

IR$^{KBr}_{max}$ cm$^{-1}$: 3430 (OH, NH), 1675, 1495 (amide), 1070 (ether), 860, 840 (Me$_3$Si), 735, and 700 (Ph)

$^1$H-NMR (CDCl$_3$; TMS): δ8.1–6.8 (m, 49H, t-BuBz+ 9Ph), 5.71 (d, 1H, J=8.8 Hz, OH), 5.05 (d, $J_{1,2}$=3.7 Hz, H-1, fucose moiety), 1.29 (s, 9H, t-Bu), 1.17 (d, 3H, $J_{5,6}$=6.5 Hz, H-6, fucose moiety), and 1.00 (m, 2H, CH$_2$SiMe$_3$)

$^{19}$F-NMR (CDCl$_3$; CFCl$_3$):δ–207 (ddd, $J_{F,2H}$=51 Hz, $J_{F,3H}$=8.9 Hz, $J_{F,1H}$=2.8 Hz, 2-F)

MS: m/z Found 1723.8320 (M+H); Calcd. 1723.8343 for $C_{103}H_{120}NO_{19}FSi$

Example 9

Object: synthesis of 2-(trimethylsiiyl)ethyl O-(methyl-5-acetamide-4,7,8,9-tetra-O-acetyl-3,5-dideoxy-D-glycero-α-D-galacto-2-nunolopyranosylonate)-(2→3)-O-(2,4,6-tri-O-benzoyl-β-D-galactopyranosyl)-(1→4)-O-[(3,4-di-O-benzyl-2-deoxy-2-fluoro-α-L-fucopyranosyl)-(1→3)]-O-[6-O-benzyl-2-deoxy-2-(4-t-butylbenzamide)-β-D-glucopyranosyl]-(1→3)-O-(2,4,6-tri-O-benzyl-β-D-galactopyranosyl)-(1→4)-2,3,6-tri-O-benzyl-β-glucopyranoside [said structural formula (18): hereinafter, abbreviated to compound (18)].

196 mg (0.114 mmol) of compound (17) obtained in Example 8 and methyl-O-(methyl-5-acetamide-4,7,8,9- tetra-O-acetyl-3,5-dideoxy-D-glycero-α-D-galacto-2-nunolopyranosylonate)-(2→3)-O-(2,4,6-tri-O-benzoyl-1-thio-β-D-galactopyranoside [said structural formula (13)] were dissolved in 6 mL of anhydrous dichloromethane and 500 mg of activated molecular sieves (pore size 4 Å) was added under an argon atmosphere. After stirring at room temperature for 12 hr, 165 mg (0.639 mmol) of dimethyl (methylthio)sulfonium triflate (DMTST) was added and stirred at the same temperature for 24 hr. The reaction mixture was cooled in ice, then 0.6 mL of methanol and 0.3 mL of trimethylamine were added, and stirred at the same temperature for 30 min. After diluting with dichloromethane, filtration and washing, the combined filtrate and the washings were washed with aq. sodium carbonate and satd. brine. The solution was dried with sodium sulfate and concentrated under a reduced pressure. The residual obtained was submitted to flash chromatography (eluent; n-hexane:ethyl acetate=1:3) to give 141 mg (46.4% yield) of the said compound (18).

The analytical results of this compound are as follows:

$C_{150}H_{169}N_2O_{39}FSi$ (mol. wt. 2671.0)

$[\alpha]_D^{23}$=−16.3°(c 0.895, chloroform)

$IR^{KBr}_{max}$ cm$^{-1}$: 3400 (NH), 1740, 1270 (ester), 1670, 1500 (amide), 1100 (ether), 860, 840 (Me$_3$Si), 735, and 715 (Ph)

$^1$H-NMR (CDCl$_3$; TMS): δ8.3–6.8 (m, 64H, t-BuBz+12 Ph), 5.70 (m, 1H, H-8, sialic acid moiety), 5.51 (dd, 1H, $J_{1,2}$=8.1 Hz, $J_{2,3}$=9.8 Hz, H-2, galactose moiety), 5.39 (br d, 1H, $J_{3,4}$=$J_{4,5}$=3.8 Hz, H-2, galactose moiety), 5.26 (dd, 1H, $J_{7,8}$=9.6 Hz, $J_{6,7}$=2.6 Hz, H-7, sialic acid moiety), 3.81 (s, 3H, OCH$_3$), 2.47 (dd, 1H, $J_{3e,3a}$=12.8 Hz, $J_{3e,4}$=4.5 Hz, H-3e, sialic acid moiety), 2.17, 1.98, 1.95, 1.83 (4s, 12H, 4AcO), 1.56 (s, 3H, AcN), 1.25 (s, 9H, t-Bu), 1.14 (d, 3H, $J_{5,6}$=6.4 Hz, H-6, sialic acid moiety), and 1.02 (m, 2H, Me$_3$SiCH$_2$ CH$_2$O)

$^{19}$F-NMR (CDCl$_3$; CFCl$_3$):δ−208 (br dd, $J_{F,2H}$=50 Hz, $J_{F,3H}$=7.1 Hz, 2-F)

MS: m/z Found 2671.1168 (M+H); Calcd. 2671.1107 for $C_{150}H_{169}N_2O_{39}FSi$ Example 10

Object: synthesis of 2-(trimethylsilyl)ethyl O-(methyl-5-acetamide-4,7,8,9-tetra-O-acetyl-3,5-dideoxy-D-glycero-α-D-galacto-2-nunolopyranosylonate)-(2→3)-O-(2,4,6-tri-O-benzoyl-β-D-galactopyranosyl)-(1→4)-O-[(3,4-di-O-acetyl-2-deoxy-2-fluoro-α-L-fucopyranosyl)-(1→3)]-O-[6-O-acetyl-2-deoxy-2-(4-t-butylbenzamide)-β-D-glucopyranosyl]-(1→3)-O-(2,4,6-tri-O-acetyl-β-D-galactopyranosyl)-(1→4)-2, 3,6-tri-O-acetyl-β-D-glucopyranoside [said structural formula (19): hereinafter, abbreviated to compound (19)]. 138 mg (0.0516 mmol) of compound (18) obtained in Example 9 was dissolved in 18.3 mL of ethanol and 6.7 mL of acetic acid, and the mixture was catalytically hydrogenated by hydrogen at atmospheric pressure in the presence of 140 mg of 10% palladium—carbon warming at 45° C. for 4 days. After filtrating this, the solvent was concentrated under a reduced pressure, and 6 mL of pyridine and 4 mL of acetic anhydride were added to the residual obtained and stirred at room temperature for 13 hr. After the solution was concentrated under a reduced pressure, the residual obtained was submitted to flash chromatography (eluent; n-hexane:ethyl acetate=1:6) to give 95.5 mg (82.7% yield) of said compound (19).

The analytical results of this compound are as follows:

$C_{105}H_{133}N_2O_{48}FSi$ (mol. wt. 2238.2)

$[\alpha]_D^{24}$=−23.4°(c 0.88, chloroform)

$IR^{KBr}_{max}$ cm$^{-1}$: 3400 (NH), 1750,1230 (ester), 1670, 1535 (amide), 1070 (ether), 860, 840 (Me$_3$Si), and 715 (Ph)

$^1$H-NMR (CDCl$_3$; TMS): δ8.3–7.3 (m, 19H, t-BuBz+ 3Ph), 5.68 (m, 1H, H-8, sialic acid moiety), 4.42 (d, 1H, $J_{1,2}$=7.9 Hz, H-1, glucose moiety), 3.80 (s, 3H, OCH$_3$), 2.42 (dd, 1H, $J_{3a,3e}$=12.6 Hz, $J_{3e,4}$=4.5 Hz, H-3e, sialic acid moiety), 2.14, 2.10, 2.10, 2.09, 2.08, 2.06, 2.02, 2.01, 1.99, 1.92, 1.91, 1.79 (13 s, 39H, 13AcO), 1.58 (s, 3H, AcN), 1.34 (s, 9H, t-Bu), 1.09 (d, 3H, $J_{5,6}$=6.5 Hz, H-6, fucose moiety), and 0.89 (m, 2H, Me$_3$SiCH$_2$)

$^{19}$F-NMR (CDCl$_3$; CFCl$_3$):δ−208 (br dd, $J_{F,2H}$=50 Hz, $J_{F,3H}$=9.4 Hz, 2-F).

MS: m/z Found 2238.7893 (M+H); Calcd. 2238.7841 for $C_{105}H_{133}N_2O_{48}FSi$ Example 11

Object: synthesis of 2-(trimethylsilyl)ethyl O-(5-acetamide-3,5-dideoxy-D-glycero-α-D-galacto-2-nunolopyranosylonic acid)-(2→3)-O-β-D-galactopyranosyl-(1→4)-O-[(2-deoxy-2-fluoro-α-L-fucopyranosyl)-(1→3)]-O-[(2-deoxy-2-(4-t-butylbenzamide)-β-D-glucopyranosyl)]-(1→3)-(O-β-D-galactopyranosyl)-(1→4)-β-D-glucopyranoside [the said structural formula (β): hereinafter, abbreviated to compound (β)]. 95.5 mg (0.0426 mmol) of compound (19) obtained in Example 10 was dissolved in 6.5 mL of anhydrous methanol, then 40 mg (0.74 mmol) of sodium methoxide was added at room temperature under an argon atmosphere, and stirred at 40° C. for 24 hr.

After cooling at room temperature, 0.9 mL of water was added to the reaction mixture and stirred for 8 hr. Then the solution was passed through an Amberlite IR120 (H$^+$) layer (eluent:methanol), and the residual concentrated under a reduced pressure was submitted to gel filtration column chromatography (eluent:methanol) using SephadexLH20 (25 g) to give 56.2 mg (96.6%) of compound (β).

The analytical results of this compound are as follows:

$C_{57}H_{97}N_2O_{32}FSi$ (mol. wt. 1365.4)

$[\alpha]_D^{23}$=−30.4°(c 0.50, methanol)

$IR^{KBr}_{max}$ cm$^{-1}$: 3700–3200 (OH, NH), 2950 (methyl), 1740 (carboxylic acid), 1630, 1550 (amide), and 1070 (ether)

$^1$H-NMR (CD$_3$ OD; TMS): δ7.8–7.4 (dd, 4H, t-BuBz), 5.26 (d, 1H, H-8, $J_{1,2}$=4.0 Hz, H-1, fucose moiety), 4.27 (d, 1H, $J_{1,2}$=7.8 Hz, H-1, glucose moiety), 2.88 (dd, 1H, $J_{3a,3e}$=12.7 Hz, $J_{3e,4}$=2.9 Hz, H-3e, sialic acid moiety), 2.01 (s, 3H, AcN), 1.35 (s, 9H, t-Bu), 1.16 (d, 3H, $J_{5,6}$=6.5 Hz, H-6, fucose moiety), and 1.00 (m, 2H, Me$_3$SiCH$_2$)

$^{19}$F-NMR (CD$_3$OD; CFCl$_3$):δ−162 (br dd, $J_{F,2H}$=51 Hz, $J_{F,3H}$=10.8 Hz, 2-F).

MS: m/z Found 1365.5543 (M+H); Calcd. 1365.5560 for $C_{57}H_{97}N_2O_{32}Fsi$

Found 1387.5363 (M+Na); Calcd. 1387.5384

Evaluation of Metabolic Stability

The metabolic stability of various sialyl Lewis X derivatives to α-fucosidase was assayed. The various sialyl Lewis X derivatives which were used in Example [(2F-Fuc-t-Bu)

SLcXOSE], Comparative Example 1 (SLeX Ganglioside), and Comparative Example 2 [(2F-Fuc) SLeX Ganglioside] are shown in the following structural formulas. Herein, the compound used in the present Example is the compound represented by said structural formula (β) obtained in said Example 11.

Example [Structural formula (β)]:

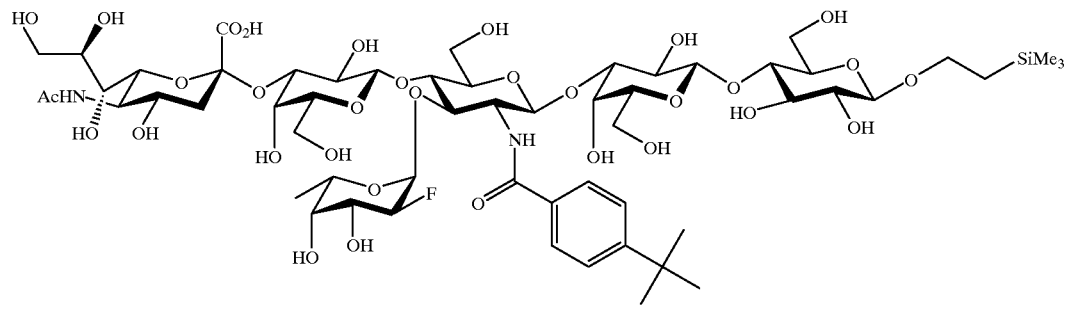

Comparative Example 1:

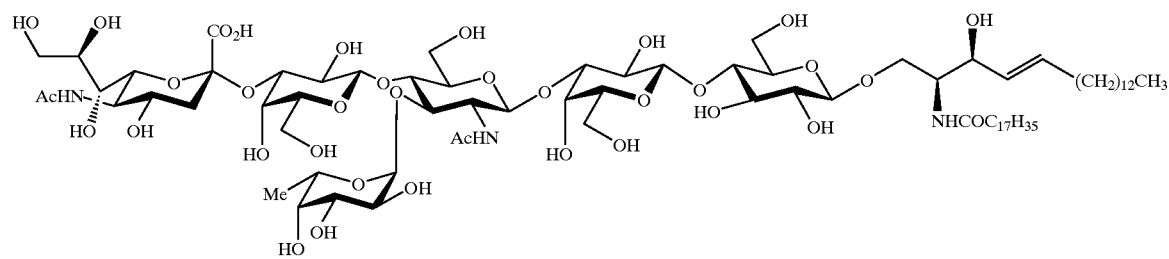

Comparative Example 2:

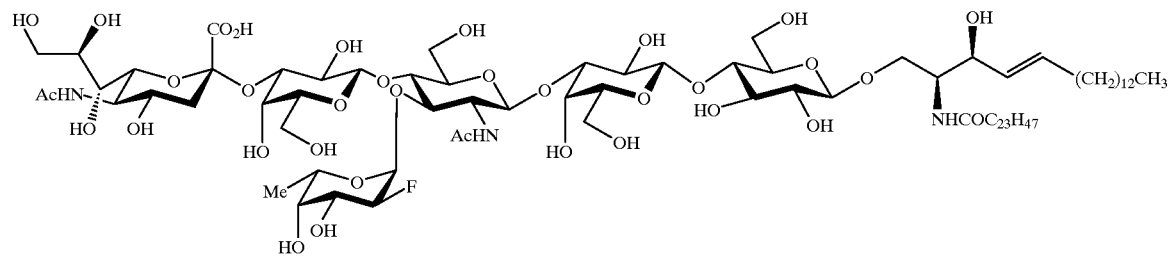

After 30 mmol of each sialyl Lewis X derivative was dissolved in 0.1 mL of dist. water, 0.1 mL of ammonium sulfate suspension of α-fucosidase (made by Wako Chemicals: 2 units or more/mg protein) was added to this solution at 28° C., then the reaction solution was charged on a silica gel TLC plate 5715 (made by Merck Company) at every reaction time course. After developing up to 2 cm using developing solvents (n-butanol:acetic acid:water=8:5:4), this was soaked in an aqueous solution of molybdenum phosphate/phosphoric acid/sulfuric acid mixture, and heated to color. The Rf values (moving ratio) on the TLC plate of products decomposed by α-fucosidase and each sialyl Lewis X derivative (substrate) were as follows.

Comparative Example 1 substrate (SleX Ganglioside): Rf=0.75, decomposed products: Rf=0.20

Comparative Example 2 substrate [(2F-Fuc) SleX Ganglioside]: Rf=0.75, decomposed products: Rf=0.20

Example substrate [(2-Fuc-t-bu) SLcXOSE]: Rf=0.70, decomposed products: Rf=0.20

Namely, it was found that the Rf of the decomposed products all showed the same value (0.20). Further, it was confirmed from the mass spectrum that each sialyl Lewis X derivative is decomposed by α-fucosidase, and the corresponding derivatives from which the fucose moiety was removed were produced as respective decomposed products. Further, as shown in following Table 1, the residual rates of the individual sialyl Lewis X derivatives were calculated from each spot area (hereinafter, sometimes referred to merely as the area) after each reaction time course as follows. Herein, each area was measured using a densitometer (software: VILBER LOURMAT BIOID V 6.31a): Residual rate of sialyl Lewis X derivative=(substrate area)/ (total area of substrate area plus decomposed product area). The following Table 1 shows the obtained spot areas of individual sialyl Lewis X derivatives for each time.

Further, FIG. 1 shows the graphed residual rates of the individual sialyl Lewis X derivatives obtained from these spot areas.

TABLE 1

| TimeCourse (min) | Spot Area (cm²) | | |
|---|---|---|---|
| | Comparative Example 1 | Comparative Example 2 | Example |
| 0 | 1.0 | 1.0 | 1.0 |
| 0.5 | 0.0* | 0.36 | — |
| 1.0 | — | 0.30 | 0.73 |
| 2.0 | — | — | 0.44 |

Here, * indicates that the color on the TLC completely disappeared.

From FIG. 1, it is clear that the compounds in the present Example are excellent in stability against α-fucosidase. The natural type sialyl Lewis X ganglioside (Comparative Example 1: SLeX Ganglioside) shows rapid decomposition by α-fucosidase, while the sialyl Lewis X ganglioside (comparative Example 2: (2F-Fuc) SLeX Ganglioside) in which the hydroxy group at 2-position of fucose is substituted with a fluorine atom exhibits a weak resistance to decomposition by α-fucosidase, and is better in metabolic stability.

It has been found that the compound of the present Example [structural formula (β):(2F-Fuc-t-Bu) SLcXOSE] is strongly resistant to decomposition reaction by α-fucosidase. This is because the compound of the present Example is not easily decomposed by α-fucosidase compared with other derivatives, and is excellent in metabolic stability. From this result, it is expected to be capable of retaining sufficient selectin-adhesive-inhibition activity.

What is claimed is:

1. 2-Fluorofucosyl-N-aroylglucosamine derivatives represented by the following general formula (1):

General formula (1):

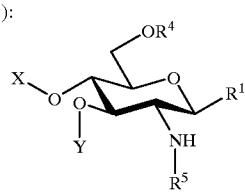

wherein X and Y in said general formula (1) are groups represented by following general formulas (A) or (B), if X is general formula (A), Y is general formula (B), and if X is general formula (B), Y is general formula (A)

General formula (A):

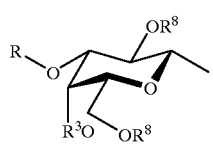

General formula (B):

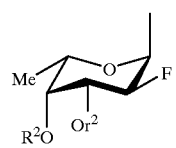

herein, in said general formula (A), R is a hydrogen atom, a protective group of the hydroxyl group, phosphate residue, sulfate residue, or a sialyl group represented by the following general formula (a), General formula (a):

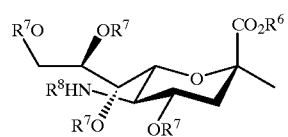

wherein $R^6$ in the above general formula (a) shows a hydrogen atom, sodium atom or C1–10 alkyl group; $R^7$ shows a hydrogen atom, C1–10 alkanoyl group or C7–15 aroyl group; $R^8$ shows an acetyl group, hydroxyacetyl group or C1–10 alkanoyloxyacetyl group), further, in the above general formula (1), $R^1$ is a hydrogen atom, hydroxyl group, C1–10 alkanoyloxy group having no substituent or having one or more substituents, C7–15 aroyloxy group, arylthio group having no substituent or having one or more substituents, C1–18 alkoxy group, branched long chain alkoxy group, arylmethoxy group having no substituent or having one or more substituents, or 2-trisilylethoxy group having C1–4 alkyl group or phenyl group, or a group represented by following general formulas (b) or (c), General formula (b):

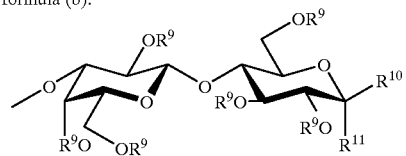

General formula (c):

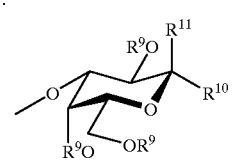

wherein $R^9$ in the above general formulas (b) and (c) shows a hydrogen atom, C1–10 alkanoyl group, C7–15 aroyl group or phenylmethoxy group having no substituent or having substituents; $R^{10}$ shows a hydrogen atom, hydroxyl group, 2-trisilylethoxy group having C1–4 alkyl group or phenyl group, C1–30 alkoxy group, or a group represented by following general formula (d); and $R^{11}$ shows a hydrogen atom or —O—C(=NH)CCl₃, General formula (d):

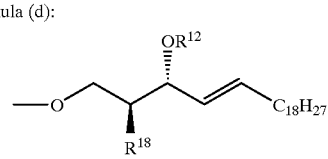

wherein $R^{12}$ in the above general formula (d) shows a hydrogen atom or benzoyl group; $R^{13}$ shows an azide, amine or sphingosine represented by NHCO $R^{14}$ ($R^{14}$ is a C15–25 alkyl group); $R^{11}$ shows a hydrogen atom or —O—C(=NH)CCl$_3$, and in the above general formula (1), (A) and (B), $R^2$, $R^3$ and $R^4$ are a hydrogen atom, C1–10 alkanoyl group, C7–15 aroyl group, or phenylmethyl group having no substituent or having substituents (wherein at least two of $R^2$, $R^3$ and $R^4$ may be the same or different from each other) and $R_5$ shows an aroyl group having no substituent or having substituents.

2. The 2-fluorofucosyl-N-aroylglucosamine derivatives as claimed in claim 1 represented by the following general formula (2):

General formula (2):

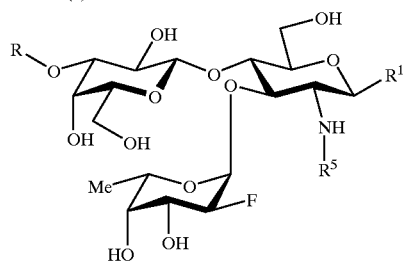

(wherein R, $R^1$ and $R^5$ in said general formula (2) are the same as described above).

3. The 2-fluorofucosyl-N-aroylglucosamine derivatives as claimed in claim 1 represented by the following general formula (3):

General formula (3):

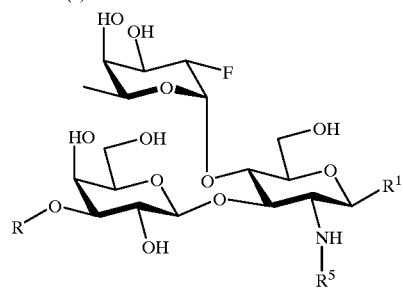

(wherein R, $R^1$ and $R^5$ in said general formula (3) are the same as described above).

4. The 2-fluorofucosyl-N-aroylglucosamine derivatives as claimed in claim 1 represented by the following structural formula (α):

Structural formula (α):

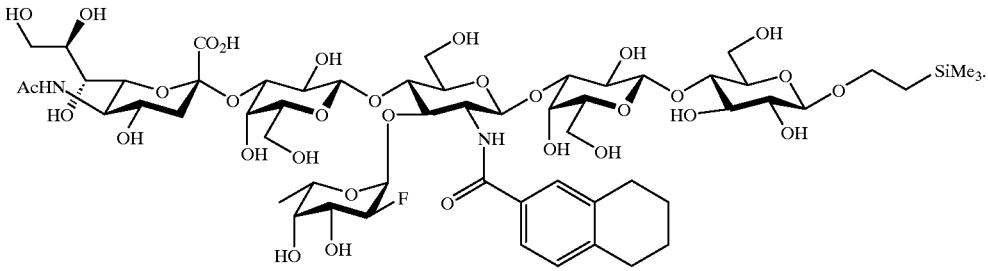

5. The 2-fluorofucosyl-N-aroylglucosamine derivatives as claimed in claim 1 represented by the following structural of formula (β):

Structural formula (β):

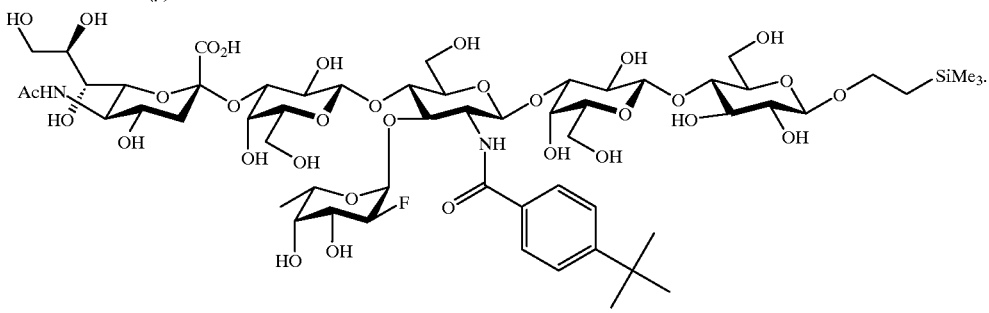

6. The 2-fluorofucosyl-N-aroylglucosamine derivatives as claimed in claim 1 represented by the following structural formula (γ):

Structural formula (γ):

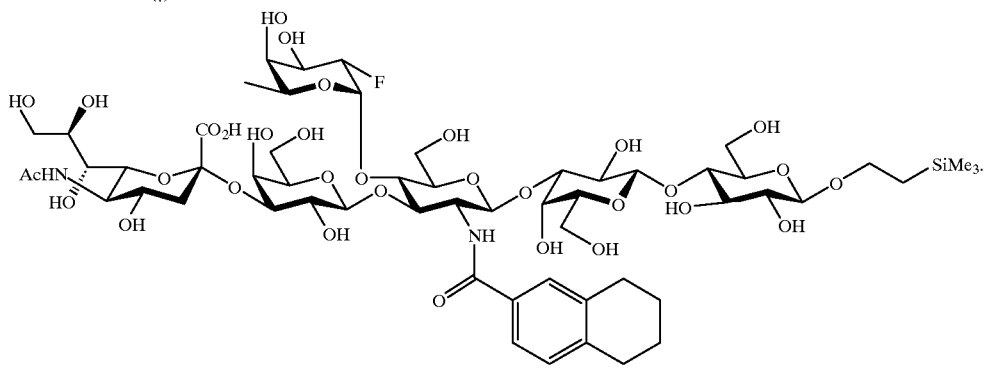

7. The 2-fluorofucosyl-N-aroylglucosamine derivatives as claimed in claim 1 represented by the following structural formula (δ):

Structural formula (δ):

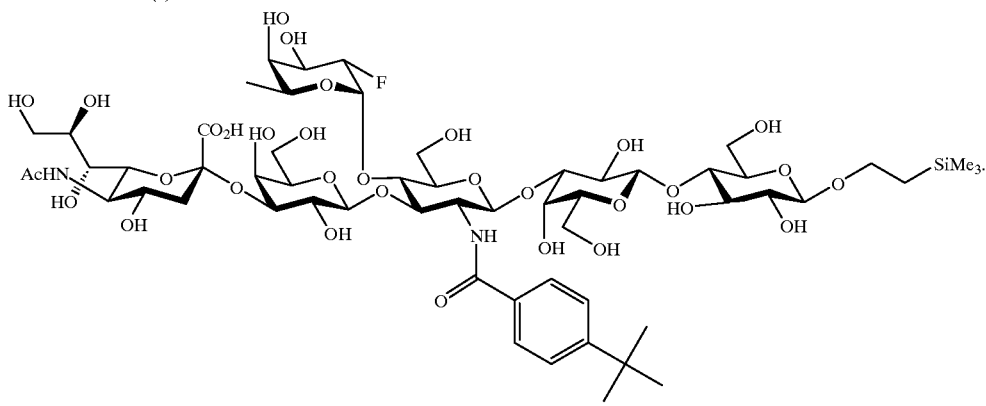

8. A method for preparing the 2-fluorofucosyl-N-aroylglucosamine derivatives wherein a compound represented by the following general formulas (A') and (B') and an aroylglucosamine derivative represented by the following general formula (C') are used when preparing the 2-fluorofucosyl-N-aroylglucosamine derivatives represented by said general formula (1), General formula (A'):

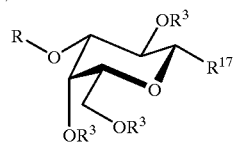

General formula (B'):

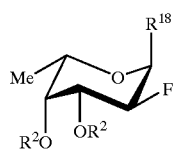

-continued

General formula (C'):

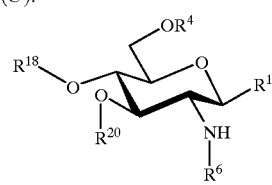

(wherein R, $R^1$, $R^2$, $R^3$, $R^4$ and $R^5$ in said general formulas (A'), (B') and (C') are the same as described above; $R^{17}$, $R^{18}$, $R^{19}$ and $R^{20}$ are reactive groups, respectively; and $R^{17}$ shows reactivity with $R^{19}$ or $R^{20}$; and $R^{18}$ shows reactivity with $R^{19}$ or $R^{20}$).

9. The method for preparing the 2-fluorofucosyl-N-aroylglucosamine derivative as claimed in claim 8 comprises processes of: synthesizing an intermediate of the 2-fluorofucosyl-N-aroylglucosamine derivative through reaction of the aroylglucosamine derivative of said general formula (C') with 2-fluorofucose of said general formula (B'); reacting said intermediate with a galactose derivative of said general formula (A'); and hydrogenation, when preparing the 2-fluorofucosyl-N-aroylglucosamine derivatives represented by said general formula (2).

10. The method for preparing the 2-fluorofucosyl-N-aroylglucosamine derivatives as claimed in claim 8 comprises processes of: synthesizing an intermediate of the 2-fluorofucosyl-N-aroylglucosamine derivative through reaction of the aroylglucosamine derivative of said general formula (C') with a galactose derivative of said general formula (A'); reacting said intermediate with 2-fluorofucose of said general formula (B'); and hydrogenation, when preparing the 2-fluorofucosyl-N-aroylglucosamine derivatives represented by said general formula (3).

11. The method for preparing the 2-fluorofucosyl-N-aroylglucosamine derivatives as claimed in claim 8 comprises processes through: reacting 2-(trimethylsiiyl)ethyl O-(4,6-O-benzylidene-2-deoxy-2-phthalimide-β-D-glucopyranosyl)-(1→3)-O-(2,4,6-tri-o-benzyl-β-D-galactopyranosyl)-(1→4)-2,3,6-tri-O-benzyl-β-D-glucopyranoside represented by the following structural formula (e) with methyl 3,4-di-O-benzyl-2-deoxy-2-fluoro-1-thio-L-fucopyranoside represented by the following structural formula (f); introducing a 2-naphthamide group as a substituent instead of said phthalimide group; cleaving said benzylidene group; reacting the obtained intermediate of 2-fluorofucosyl-N-aroylglucosamine derivative with a sialylgalactose derivative represented by the following structural formula (g) to introduce as a substituent into said cleavage site; hydrogenation reduction; acetylation; and hydrolysis, when preparing the 2-fluorofucosyl-N-aroylglucosamine derivatives represented by said structural formula (α), glucopyranoside represented by said structural formula (e) with methyl 3,4-di-O-benzyl-2-deoxy-2-fluoro-1-thio-L-fucopyranoside represented by said structural formula (f); introducing a 4-t-butylbenzamide group as a substituent instead of said phthalimide group; cleaving said benzylidene group; reacting the obtained intermediate of 2-fluorofucosyl-N-aroylglucosamine derivative with a sialylgalactose derivative represented by said structural formula (g) to introduce as a substituent into said cleavage site; hydrogenation reduction; acetylation; and hydrolysis, when preparing the 2-fluorofucosyl-N-aroylglucosamine derivative represented by said structural formula (β).

13. The method for preparing the 2-fluorofucosyl-N-aroylglucosamine derivatives as claimed in claim 8 comprises processes through: introducing a 2-naphthamide group as a substituent instead of said phthalimide group in 2-(trimethylsilyl)ethyl O-(3,4,6-tri-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-glucopyranoside represented by the following structural formula (h); converting said O-acetyl groups into hydroxyl groups by hydrolysis; forming a benzylidene group by dehydrating condensation to said hydroxyl groups; cleaving the benzylidene group; reacting the obtained intermediate of 2-fluorofucosyl-N-aroylglucosamine derivative with a sialylgalactose derivative represented by said structural formula (g) to introduce as a substituent into said cleavage site; reacting methyl 3,4-di-O-benzyl-2-deoxy-2-fluoro-1-thio-L-fucopyranoside represented by said structural formula (f); hydrogenation reduction; acetylation; and hydrolysis, when preparing the 2-fluorofucosyl-N-aroylglucosamine derivatives represented by said structural formula (γ), Structural formula (e):

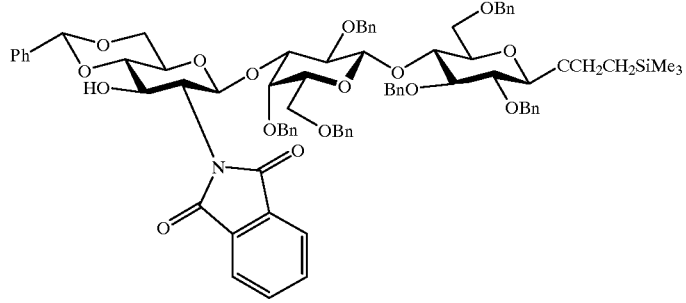

Structural formula (f):

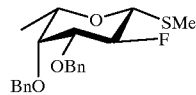

Structural formula (g):

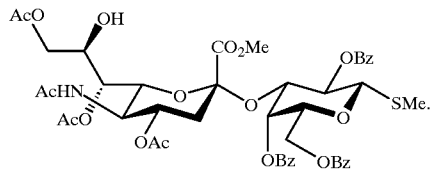

12. The method for preparing the 2-fluorofucosyl-N-aroylglucosamine derivatives as claimed in claim 8 comprises processes through: reacting 2-(trimethylsilyl)ethyl O-(4,6-O-benzylidene-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-

Structural formula (h):

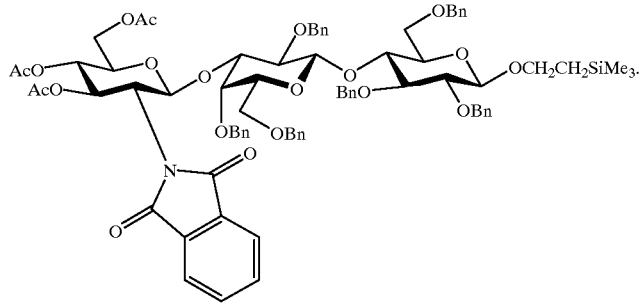

14. The method for preparing the 2-fluorofucosyl-N-aroylglucosamine derivatives as claimed in claim 8 comprises processes through: introducing a 4-t-butylbenzamide group as a substituent instead of said phthalimide group in 2-(trimethylsilyl)ethyl O-(3,4,6-tri-O-acetyl-2-deoxy-2-phthalimide-β-D-glucopyranosyl)-(1→3)-O-(2,4,6-tri-O-benzyl-β-D-galactopyranosyl)-(1→4)-2,3,6-tri-O-benzyl-β-D-glucopyranoside represented by said structural formula (h); converting said O-acetyl groups into hydroxyl groups by hydrolysis; forming a benzylidene group by dehydrating condensation to said hydroxyl groups; cleaving the benzylidene group; reacting the obtained intermediate of 2-fluorofucosyl-N-aroylglucosamine derivative with a sialylgalactose derivative represented by said structural formula (g) to introduce as a substituent into said cleavage site; reacting methyl 3,4-di-O-benzyl-2-deoxy-2-fluoro-1-thio-L-fucopyranoside represented by said structural formula (f); hydrogenation reduction; acetylation; and hydrolysis, when preparing the 2-fluorofucosyl-N-aroylglucosamine derivatives represented by said structural formula (δ).

15. Intermediates of 2-fluorofucosyl-N-aroylglucosamine derivatives represented by the following general formula (4), General formula (4):

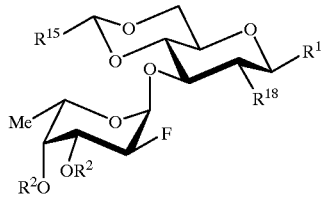

(wherein $R^{15}$ shows a phenyl group having no substituent or having substituents; and $R^{16}$ shows an aroyl group having no substituent or having substituents).

16. The intermediates of the 2-fluorofucosyl-N-aroylglucosamine derivatives as claimed in claim 15 wherein said $R^{16}$ is one group selected from the groups consisting of a phthalimide ring group, a 2-naphthoylamide group and a 4-t-butylbenzoylamide group.

17. The intermediates of the 2-fluorofucosyl-N-aroylglucosamine derivatives represented by the following general formula (5):

General formula (5):

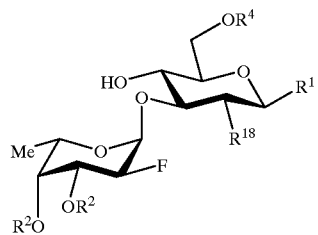

(wherein $R^{16}$ is the same as claimed in claim 15).

18. The intermediates of the 2-fluorofucosyl-N-aroylglucosamine derivatives as claimed in claim 17 wherein said $R^{16}$ is one group selected from the groups consisting of a phthalimide ring group, a 2-naphthoylamide group and a 4-t-butylbenzoylamide group.

19. The method for preparing the intermediates of 2-fluorofucosyl-N-aroylglucosamine derivatives comprises reaction of the aroylglucosamine derivative represented by the following general formula (i) with the compound represented by general formula (B'), when preparing the intermediates of 2-fluorofucosyl-N-aroylglucosamine derivatives represented by general formula (4), General formula (i):

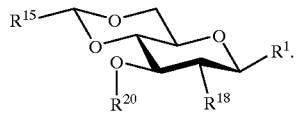

20. The method for preparing the intermediates of 2-fluorofucosyl-N-aroylglucosamine derivatives as claimed in claim 19 wherein said $R^{16}$ in said general formula (i) is one group selected from the groups consisting of a phthalimide ring group, a 2-naphthoylamide group and a 4-t-butylbenzoylamide group.

21. The method for preparing the intermediates of 2-fluorofucosyl-N-aroylglucosamine derivatives comprises cleavage of a benzylidene ring group in the intermediates of 2-fluorofucosyl-N-aroylglucosamine derivatives represented by said general formula (4) as claimed in claim 15, when preparing the intermediates of 2-fluorofucosyl-N-aroylglucosamine derivatives represented by general formula (5).

22. The method for preparing the intermediates of 2-fluorofucosyl-N-aroylglucosamine derivatives as claimed in claim 21 wherein said $R^{16}$ in said general formula (5) is one group selected from the groups consisting of a phthalimide ring group, a 2-naphthoylamide group and a 4-t-butylbenzoylamide group.

* * * * *